United States Patent
Greiwe

(10) Patent No.: US 11,369,479 B2
(45) Date of Patent: *Jun. 28, 2022

(54) HUMERAL HEAD IMPLANT SYSTEM

(71) Applicant: Howmedica Osteonics Corp., Mahwah, NJ (US)

(72) Inventor: Raymond Michael Greiwe, Edgewood, KY (US)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/492,803

(22) Filed: Oct. 4, 2021

(65) Prior Publication Data

US 2022/0023056 A1    Jan. 27, 2022

Related U.S. Application Data

(63) Continuation of application No. 16/531,885, filed on Aug. 5, 2019, now Pat. No. 11,160,660, which is a
(Continued)

(51) Int. Cl.
| | |
|---|---|
| *A61F 2/40* | (2006.01) |
| *A61B 17/02* | (2006.01) |
(Continued)

(52) U.S. Cl.
CPC .......... *A61F 2/4014* (2013.01); *A61B 17/025* (2013.01); *A61B 17/15* (2013.01);
(Continued)

(58) Field of Classification Search
CPC ..... A61F 2/4014; A61F 2/4003; A61F 2/4612
See application file for complete search history.

(56) References Cited

U.S. PATENT DOCUMENTS

| | | |
|---|---|---|
| 4,310,931 A | 1/1982 | Muller |
| 4,934,352 A | 6/1990 | Sullivan, Jr. |

(Continued)

FOREIGN PATENT DOCUMENTS

| | | |
|---|---|---|
| DE | 102008010478 A1 | 8/2009 |
| EP | 1402854 A2 | 3/2004 |

(Continued)

OTHER PUBLICATIONS

Extended European Search Report for Application No. EP17844446.9 dated Jun. 25, 2020.
(Continued)

*Primary Examiner* — Brian A Dukert
(74) *Attorney, Agent, or Firm* — Lerner, David, Littenberg, Krumholz & Mentlik, LLP

(57) ABSTRACT

A humeral head implant system includes a head component including a first articulating surface, a second bottom surface extending from the first spherical articulating surface, a first cavity extending a first distance into the head component from the second bottom surface, and a second cavity extending into the head component along a cavity axis. The head component defines a head axis extending through a center of the first articulating surface parallel to the cavity axis. A base component defines a slot extending from a first width to a second width. An insert component includes an insert body, a first engagement feature, and a slot engagement feature. The first engagement feature is received in the second cavity along the cavity axis. The insert body has an insert thickness less than the first distance, and the slot engagement feature slides into the slot in a direction transverse to the cavity axis.

12 Claims, 69 Drawing Sheets

Related U.S. Application Data continuation of application No. 15/686,099, filed on Aug. 24, 2017, now Pat. No. 10,368,999.

(60) Provisional application No. 62/531,721, filed on Jul. 12, 2017, provisional application No. 62/469,425, filed on Mar. 9, 2017, provisional application No. 62/463,448, filed on Feb. 24, 2017, provisional application No. 62/419,905, filed on Nov. 9, 2016, provisional application No. 62/378,963, filed on Aug. 24, 2016.

(51) Int. Cl.
| | | |
|---|---|---|
| *A61B 17/15* | (2006.01) | |
| *A61B 17/88* | (2006.01) | |
| *A61B 17/16* | (2006.01) | |
| *A61F 2/46* | (2006.01) | |
| *A61F 2/30* | (2006.01) | |
| *A61B 17/17* | (2006.01) | |

(52) U.S. Cl.
CPC ...... *A61B 17/1684* (2013.01); *A61B 17/8866* (2013.01); *A61F 2/4003* (2013.01); *A61F 2/4612* (2013.01); *A61B 17/1778* (2016.11); *A61F 2002/30329* (2013.01); *A61F 2002/30332* (2013.01); *A61F 2002/30367* (2013.01); *A61F 2002/30387* (2013.01); *A61F 2002/30535* (2013.01); *A61F 2002/30555* (2013.01); *A61F 2002/30878* (2013.01); *A61F 2002/30884* (2013.01)

(56) References Cited

U.S. PATENT DOCUMENTS

| | | | |
|---|---|---|---|
| 5,314,479 | A | 5/1994 | Rockwood, Jr. et al. |
| 5,330,536 | A * | 7/1994 | Tager ................ A61F 2/3662 623/23.33 |
| 5,358,526 | A * | 10/1994 | Tornier ............... A61F 2/4014 623/19.14 |
| 5,437,677 | A | 8/1995 | Shearer et al. |
| 5,910,171 | A | 6/1999 | Kummer et al. |
| 6,187,012 | B1 | 2/2001 | Masini |
| 6,197,062 | B1 | 3/2001 | Fenlin |
| 6,197,063 | B1 | 3/2001 | Dews |
| 6,436,147 | B1 | 8/2002 | Zweymuller |
| 6,530,957 | B1 | 3/2003 | Jack |
| 6,626,946 | B1 | 9/2003 | Walch et al. |
| 6,673,114 | B2 | 1/2004 | Hartdegen et al. |
| 6,676,705 | B1 | 1/2004 | Wolf |
| 6,719,799 | B1 | 4/2004 | Kropf |
| 6,736,851 | B2 | 5/2004 | Maroney et al. |
| 6,749,637 | B1 | 6/2004 | Bahler |
| 6,899,736 | B1 | 5/2005 | Rauscher et al. |
| 6,942,699 | B2 | 9/2005 | Stone et al. |
| 7,175,663 | B1 | 2/2007 | Stone |
| 7,189,261 | B2 | 3/2007 | Dews et al. |
| 7,431,736 | B2 | 10/2008 | Maroney et al. |
| 7,621,961 | B2 | 11/2009 | Stone |
| 7,758,650 | B2 | 7/2010 | Dews et al. |
| 7,819,923 | B2 | 10/2010 | Stone et al. |
| 8,052,758 | B1 | 11/2011 | Winslow |
| 8,062,376 | B2 | 11/2011 | Shultz et al. |
| 8,070,820 | B2 | 12/2011 | Winslow et al. |
| 8,236,059 | B2 | 8/2012 | Stone et al. |
| 8,246,687 | B2 | 8/2012 | Katrana et al. |
| 8,647,387 | B2 | 2/2014 | Winslow |
| 8,702,804 | B2 | 4/2014 | Smith et al. |
| 8,734,457 | B2 | 5/2014 | Bailey et al. |
| 8,771,362 | B2 | 7/2014 | Isch et al. |
| 8,795,379 | B2 | 8/2014 | Smith et al. |
| 8,876,908 | B2 | 11/2014 | Katrana et al. |
| 8,906,103 | B2 | 12/2014 | Stone et al. |
| 8,968,415 | B2 | 3/2015 | Meridew et al. |
| 9,241,803 | B2 | 1/2016 | Stone et al. |
| 9,283,083 | B2 | 3/2016 | Winslow et al. |
| 9,326,862 | B2 | 5/2016 | Smith et al. |
| 9,408,704 | B2 | 8/2016 | Metzger |
| 9,498,344 | B2 | 11/2016 | Hodorek et al. |
| 9,556,162 | B2 | 2/2017 | Isch |
| 9,693,880 | B2 | 6/2017 | Olson et al. |
| 10,022,229 | B2 | 7/2018 | Cappelletti |
| 10,070,967 | B2 | 9/2018 | Chavarria et al. |
| 10,226,349 | B2 | 3/2019 | Sperling et al. |
| 10,368,998 | B2 | 8/2019 | Chavarria et al. |
| 10,368,999 | B2 | 8/2019 | Greiwe |
| 10,390,972 | B2 | 8/2019 | Rao |
| 10,433,969 | B2 | 10/2019 | Humphrey |
| 11,197,764 | B2 | 12/2021 | Mutchler et al. |
| 2001/0011193 | A1 * | 8/2001 | Nogarin ................ A61F 2/40 623/19.14 |
| 2002/0156534 | A1 | 10/2002 | Grusin et al. |
| 2003/0028253 | A1 | 2/2003 | Stone et al. |
| 2003/0097183 | A1 | 5/2003 | Rauscher et al. |
| 2004/0064190 | A1 | 4/2004 | Ball et al. |
| 2005/0033443 | A1 | 2/2005 | Blatter et al. |
| 2005/0071014 | A1 | 3/2005 | Barnett et al. |
| 2006/0020344 | A1 | 1/2006 | Shultz et al. |
| 2006/0069445 | A1 | 3/2006 | Ondrla et al. |
| 2007/0050040 | A1 | 3/2007 | Guederian et al. |
| 2007/0118230 | A1 | 5/2007 | Callaway et al. |
| 2007/0162140 | A1 | 7/2007 | McDevitt |
| 2007/0173945 | A1 | 7/2007 | Wiley et al. |
| 2007/0179624 | A1 | 8/2007 | Stone et al. |
| 2007/0225821 | A1 | 9/2007 | Reubelt et al. |
| 2008/0228281 | A1 | 9/2008 | Forrer et al. |
| 2009/0281630 | A1 | 11/2009 | Delince et al. |
| 2011/0060417 | A1 | 3/2011 | Simmen et al. |
| 2012/0143204 | A1 | 6/2012 | Blaylock et al. |
| 2012/0232667 | A1 | 9/2012 | Katrana et al. |
| 2013/0090736 | A1 | 4/2013 | Katrana et al. |
| 2013/0197652 | A1 | 8/2013 | Ekelund et al. |
| 2014/0277518 | A1 | 9/2014 | Iannotti |
| 2015/0265411 | A1 | 9/2015 | Deransart et al. |
| 2016/0213480 | A1 | 7/2016 | Stone et al. |
| 2016/0262902 | A1 | 9/2016 | Winslow et al. |
| 2016/0324648 | A1 | 11/2016 | Hodorek et al. |
| 2016/0361173 | A1 | 12/2016 | Reubelt et al. |
| 2017/0049573 | A1 | 2/2017 | Hodorek et al. |
| 2017/0056187 | A1 | 3/2017 | Humphrey et al. |
| 2018/0271667 | A1 | 9/2018 | Kemp et al. |
| 2018/0280152 | A1 | 10/2018 | Mutchler et al. |
| 2018/0368982 | A1 | 12/2018 | Ball |
| 2019/0274835 | A1 | 9/2019 | Wiley et al. |
| 2021/0228372 | A1 | 7/2021 | Knox et al. |

FOREIGN PATENT DOCUMENTS

| | | | |
|---|---|---|---|
| EP | 1415621 | A2 | 5/2004 |
| EP | 1782765 | A1 | 5/2007 |
| EP | 2564814 | A1 | 3/2013 |
| EP | 2604225 | A1 | 6/2013 |
| FR | 2652498 | A1 | 4/1991 |
| FR | 2773469 | A1 | 7/1999 |
| WO | 9309733 | A1 | 5/1993 |
| WO | 9617553 | A1 | 6/1996 |
| WO | 2003005933 | A2 | 1/2003 |
| WO | 2008000928 | A2 | 1/2008 |
| WO | 2013064569 | A1 | 5/2013 |
| WO | 2014067961 | A1 | 5/2014 |
| WO | 2018183484 | A1 | 10/2018 |
| WO | 2019079104 | A2 | 4/2019 |
| WO | 2020072465 | A2 | 4/2020 |

OTHER PUBLICATIONS

International Search Report and Written Opinion for PCT/US2017/048491 dated Dec. 5, 2017.

Partial Supplementary European Search Report including the Provisional Opinion for Application No. EP 17844446.9 dated Mar. 24, 2020, 15 pages.

(56) References Cited

OTHER PUBLICATIONS

Web site: Innomed orthopedic instruments, 'Shoulder instruments', Jul. 1, 2016 <http://www.innomed.net/shoulder_rets_standard.htm> Accessed Mar. 29, 2018.
International Search Report and Written Opinion for PCT/US2018/024824 dated Jul. 10, 2018. 12 pages.

* cited by examiner

DETAIL L

DETAIL N

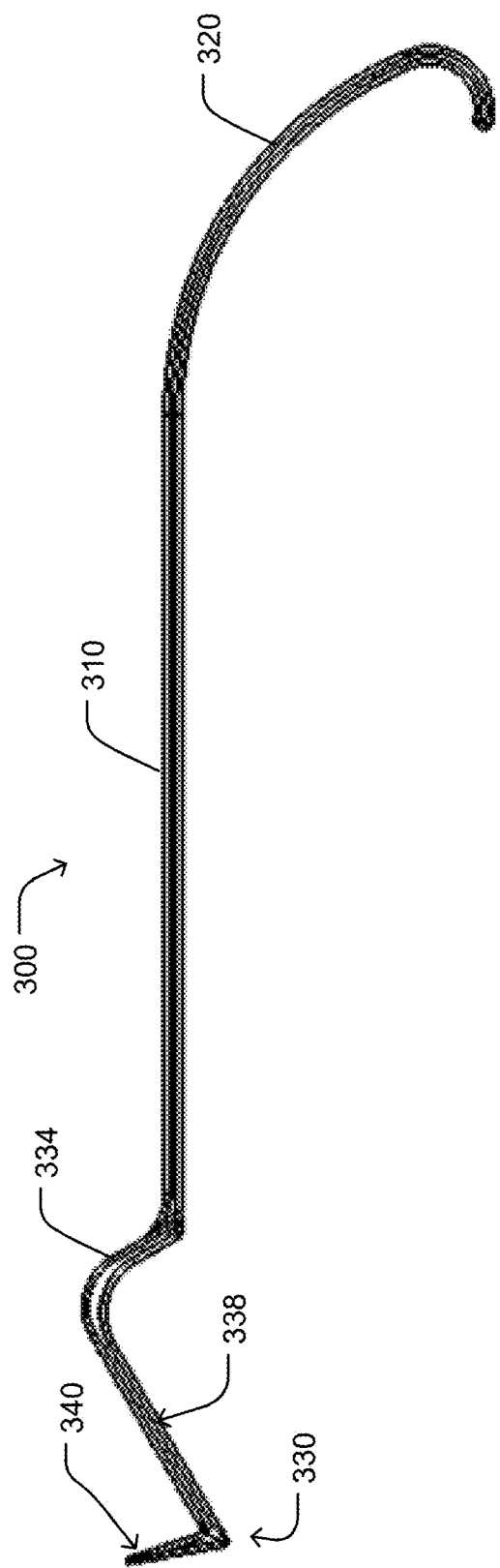
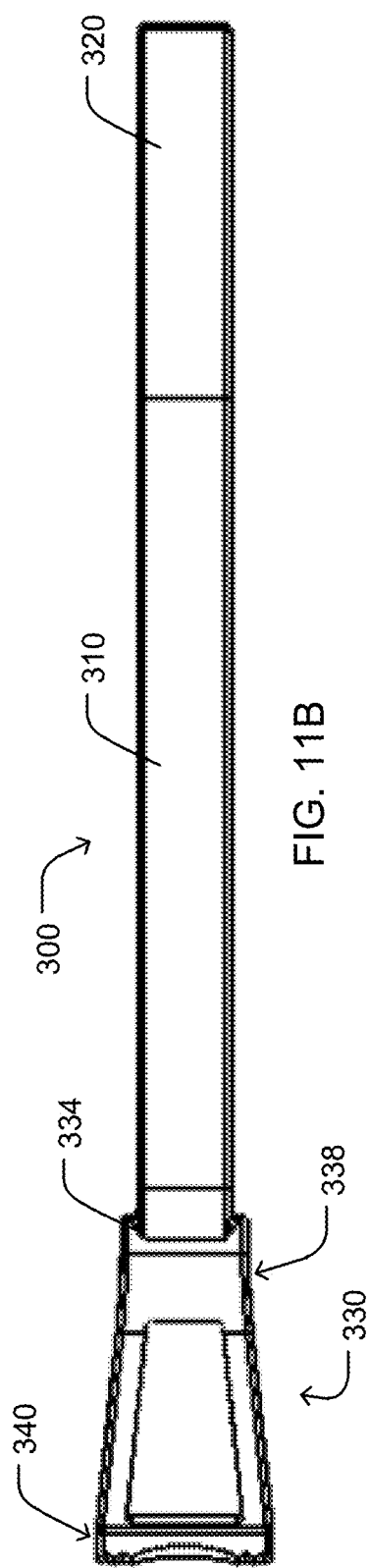
FIG. 11A
FIG. 11B

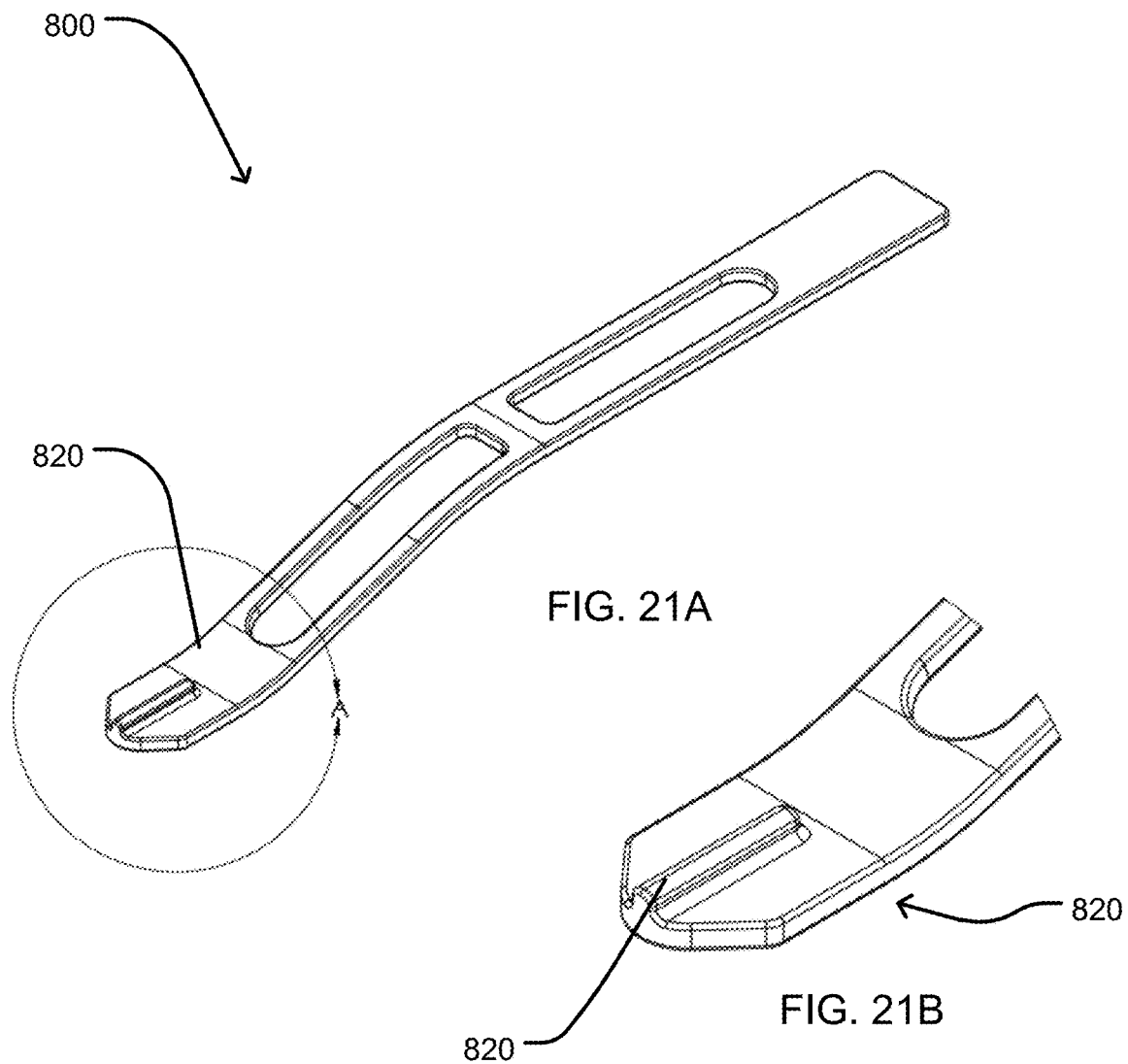

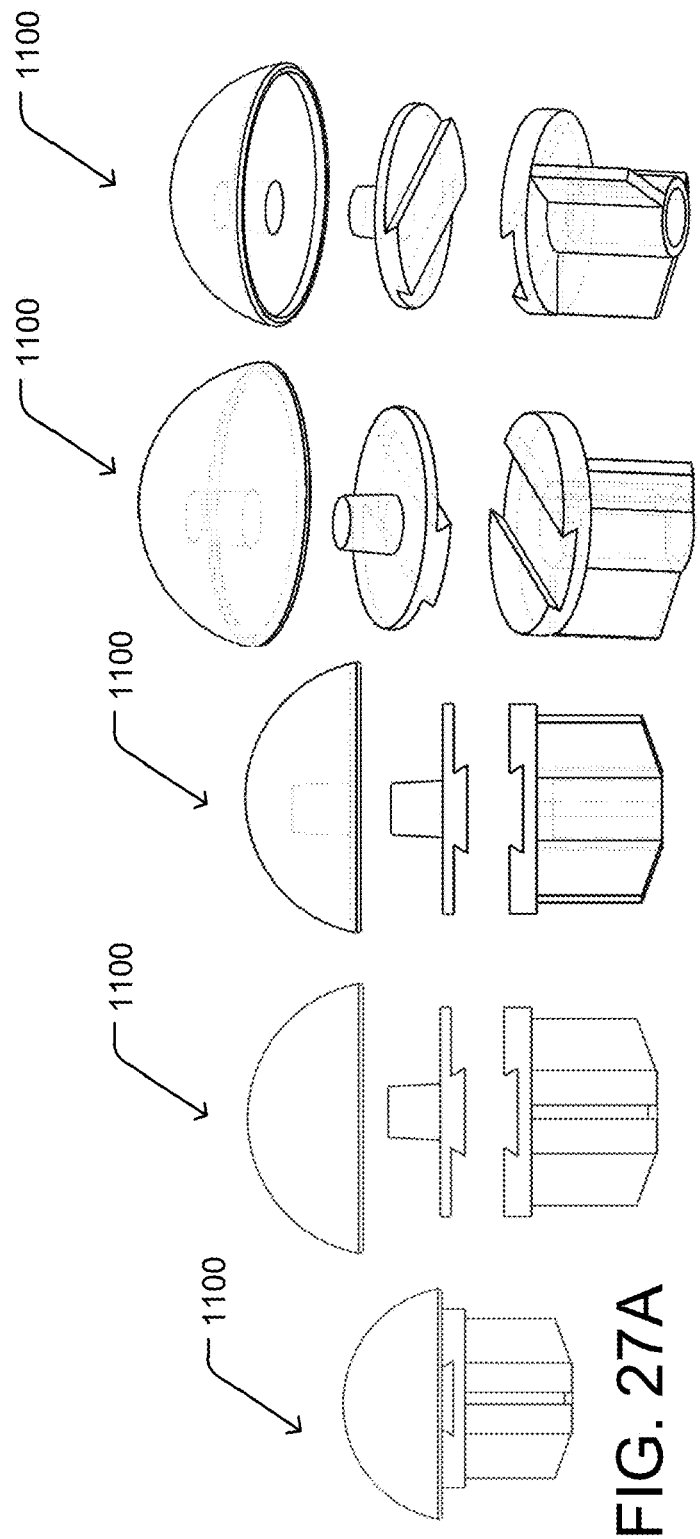

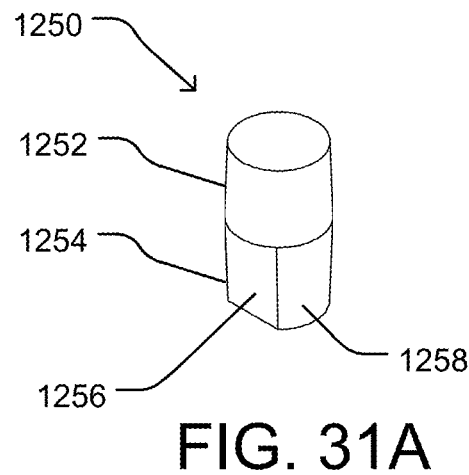
FIG. 31A
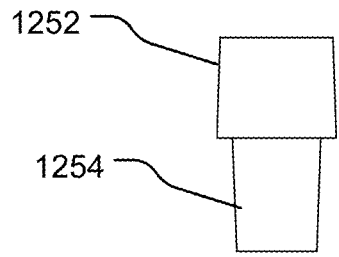
FIG. 31B
FIG. 31C
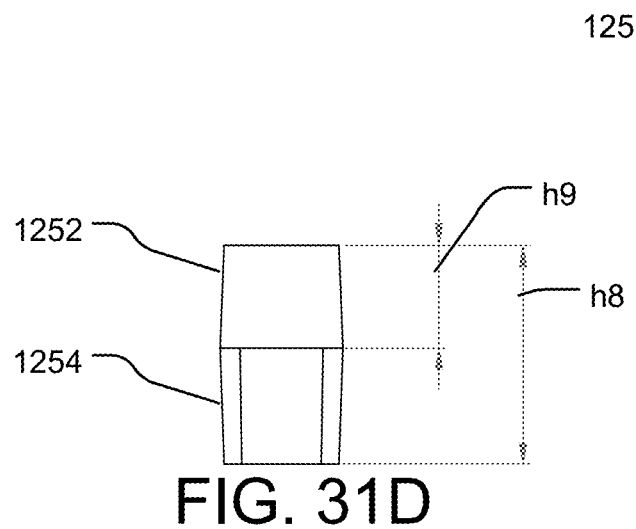
FIG. 31D
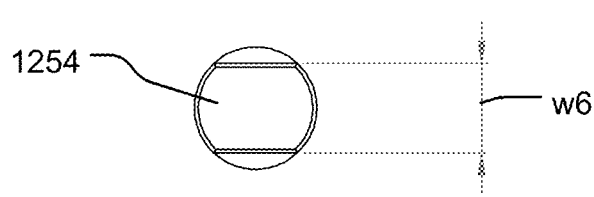
FIG. 31E

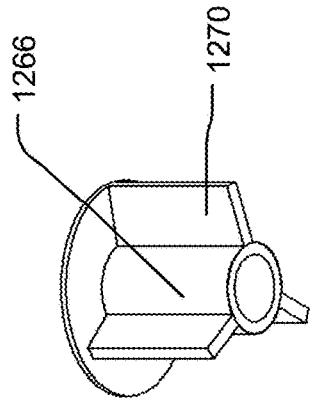
FIG. 32B
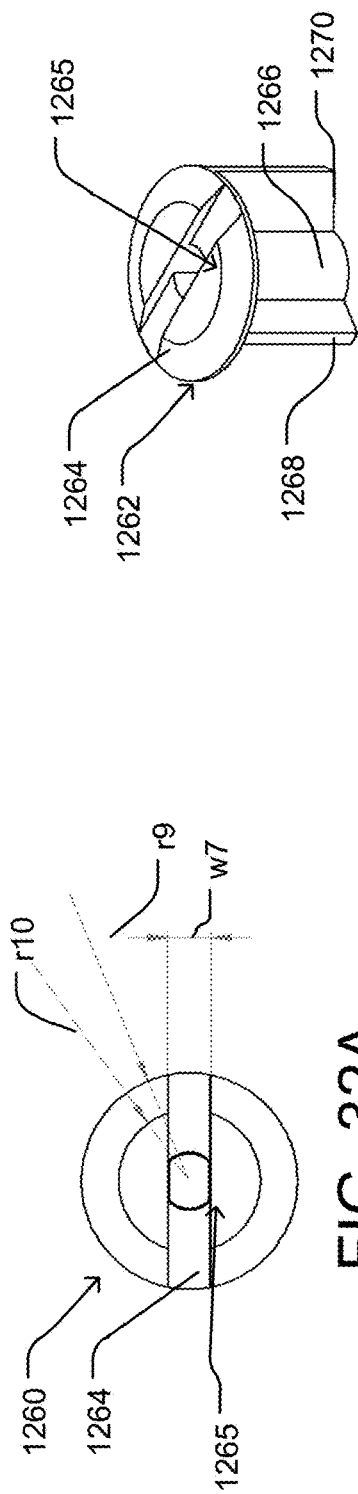
FIG. 32A
FIG. 32C
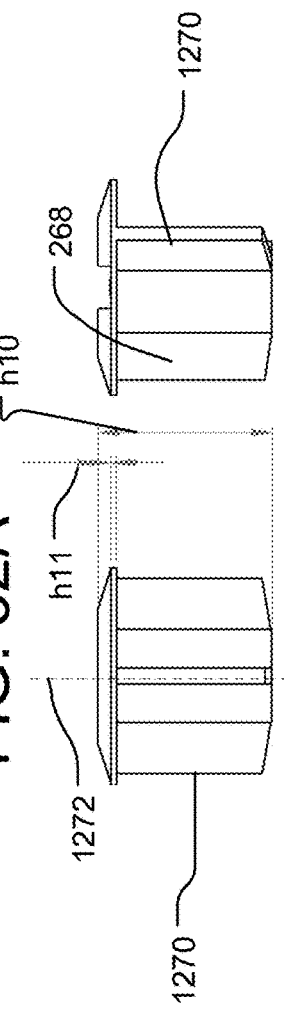
FIG. 32D
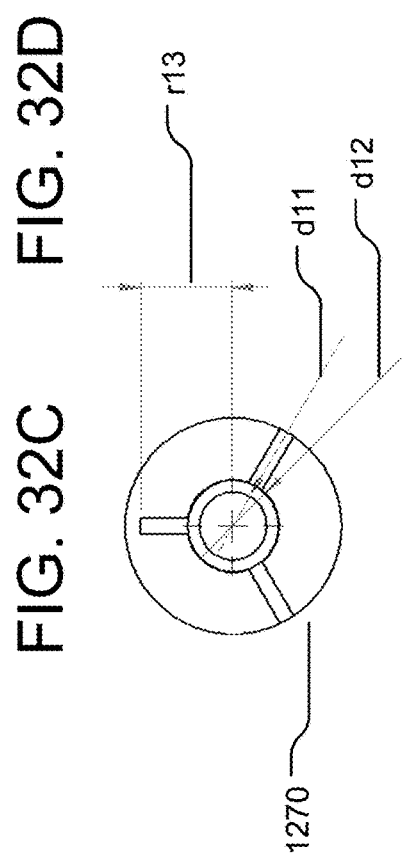
FIG. 32F
FIG. 32E

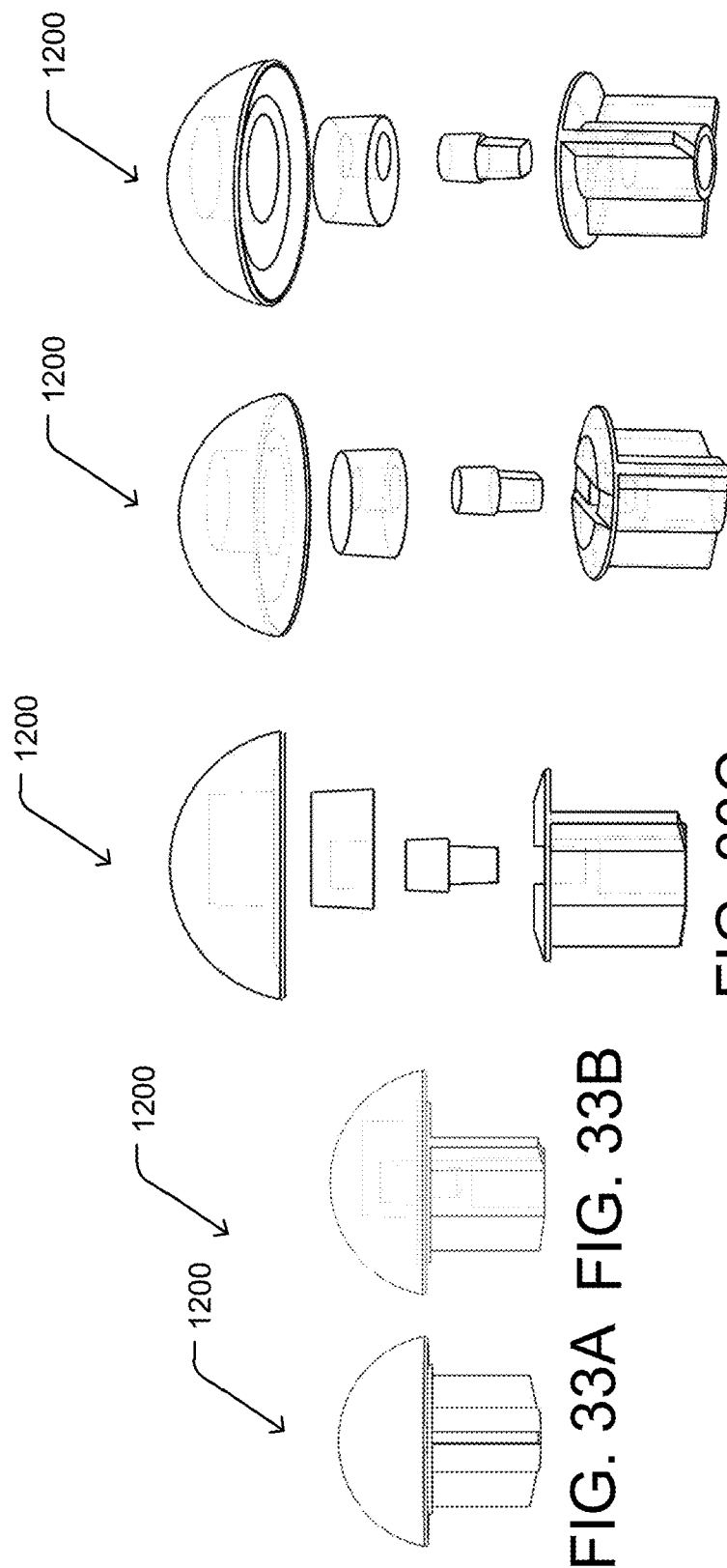

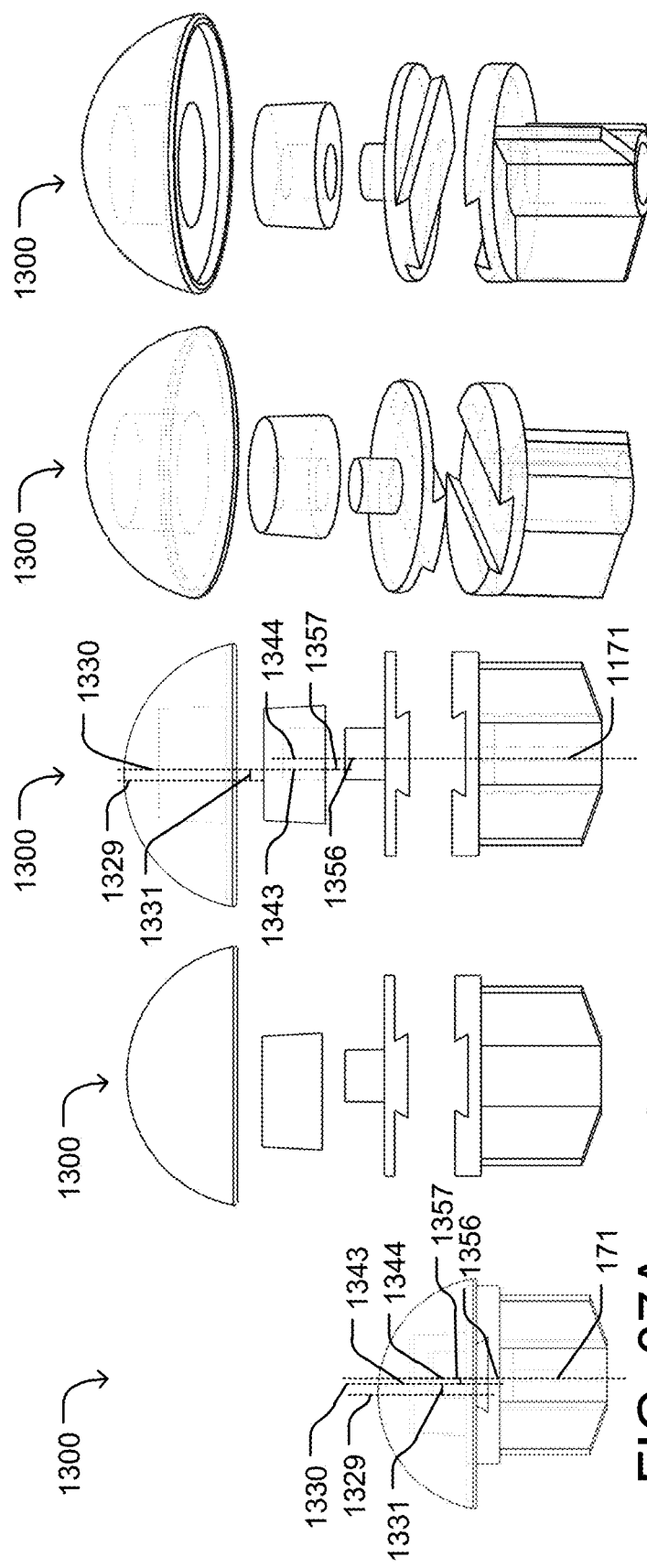

HUMERAL HEAD IMPLANT SYSTEM

CROSS-REFERENCE TO RELATED APPLICATIONS

The present application is a continuation of U.S. patent application Ser. No. 16/531,885, filed on Aug. 5, 2019, which is a continuation of U.S. Pat. No. 10,368,999, filed Aug. 24, 2017, which claims the benefit of and priority to U.S. Provisional Application No. 62/378,963, titled "ROTATOR CUFF SPARING DEVICES AND METHODS," filed Aug. 24, 2016, U.S. Provisional Application No. 62/419,905, titled "HUMERAL HEAD IMPLANT SYSTEM," filed Nov. 9, 2016, U.S. Provisional Application No. 62/469,425, titled "HUMERAL HEAD IMPLANT SYSTEM," filed Mar. 9, 2017, U.S. Provisional Application No. 62/463,448, titled "METHOD OF PERFORMING POSTERIOR ROTATOR CUFF SPARING TOTAL SHOULDER ARTHROPLASTY," filed Feb. 24, 2017, and U.S. Provisional Application No. 62/531,721, titled "METHOD OF PERFORMING POSTERIOR ROTATOR CUFF SPARING TOTAL SHOULDER ARTHROPLASTY," filed Jul. 12, 2017, the disclosures of which are incorporated herein in their entireties for all purposes.

BACKGROUND

The present disclosure relates to apparatuses, systems, and methods for shoulder surgery, more particularly to rotator cuff sparing devices and methods used during total shoulder arthroplasty.

Each year, many patients suffer from arthritis of the shoulder. Shoulder arthritis may arise from trauma, osteoarthritis, or secondary to other arthritic processes such as rheumatoid arthritis. Shoulder arthroplasty has become an advantageous surgery for patients that suffer from shoulder pain. One of the drawbacks of the surgery is the need to take down the rotator cuff so that the procedure may be performed. Shoulder arthroplasty has been performed traditionally from an anterior approach where the rotator cuff is removed and reattached at the end of the case. Shoulder replacement has traditionally shown good outcomes, but recovery may take up to 6-12 months. One of the major complications of total shoulder arthroplasty is rotator cuff failure and the pain and instability associated with this issue. Additionally, a technical issue related to the surgery is the difficulty associated with exposure of the shoulder socket which, due to the arthritic process, may be directed posteriorly. Existing systems may be insufficient to address such concerns because of difficulties associated with effectively introducing and positioning implant components for shoulder arthroplasty.

SUMMARY

According to an aspect of the present disclosure, a humeral head implant system includes a head component, a base component, and an insert component. The head component includes a first spherical articulating surface configured to articulate in a shoulder cavity, a second bottom surface extending from a rim of the first spherical articulating surface, a first cavity extending a first distance into the head component from the second bottom surface, and a second cavity extending a second distance into the head component from the first cavity along a cavity axis. The head component defines a head axis extending through a center of the first spherical articulating surface, the head axis spaced from and parallel to the cavity axis. The base component defines a slot extending from a first slot width at a third surface of the base component to a second slot width within the base component, the second slot width greater than the first slot width. The insert component includes an insert body, a first engagement feature extending from the insert body, and a slot engagement feature extending from an opposite side of the insert body as the first engagement feature. The first engagement feature is configured to be received in the second cavity along the cavity axis to engage the insert component to the head component. The insert body has an insert thickness less than the first distance of the first cavity, and the slot engagement feature is configured slide into the slot of the base component in a direction transverse to the cavity axis while the insert component is engaged to the head component.

According to another aspect of the present disclosure, a humeral head implant system includes a head component, a base component, a first insert component, and a second insert component. The head component includes a first spherical articulating surface configured to articulate in a shoulder cavity, a second bottom surface extending from a rim of the first spherical articulating surface, a first cavity extending into the head component from the second bottom surface, and a second cavity extending into the head component from the first cavity. The head component defines a head axis extending through a center of the first spherical articulating surface, the head axis spaced from and parallel to the cavity axis. The base component defines a slot extending into the base component, the slot including a slot surface and a slot cavity extending further into the base component than the slot surface. The first insert component is sized to be received within the second cavity of the head component, the first insert defining a third cavity having an insert axis configured to be spaced from and parallel to the cavity axis when the first insert component is received within the second cavity. The second insert component includes a first region sized to be received in the third cavity of the first insert component and a second region sized to be received within the slot cavity of the base component.

BRIEF DESCRIPTION OF THE DRAWINGS

FIG. 11A is a side view of an embodiment of the glenoid retractor device of FIG. 9.

FIG. 11B is a front view of an embodiment of the glenoid retractor device of FIG. 9.

FIG. 21A is a perspective view of an embodiment of a retractor device.

FIG. 21B is a detailed perspective view of a tip portion of the retractor device of FIG. 21A.

FIGS. 27A-27E illustrate various configurations of the humeral head implant system of FIG. 23.

FIG. 31A is a perspective view of an embodiment of an insert component of a humeral head implant system.

FIG. 31B is a side view of the insert component of FIG. 31A.

FIG. 31C is a top view of the insert component of FIG. 31A.

FIG. 31D is a side view of the insert component of FIG. 31A.

FIG. 31E is a bottom view of the insert component of FIG. 31A.

FIG. 32A is a top view of an embodiment of a base component of a humeral head implant system.

FIG. 32B is a top perspective view of the base component of FIG. 32A.

FIG. 32C is a first side view of the base component of FIG. 32A.

FIG. 32D is a second side view of the base component of FIG. 32A and FIG. 32E is a bottom view of the base component of FIG. 32A.

FIG. 32F is a bottom perspective view of the base component of FIG. 32A.

FIGS. 33A-33E illustrate various configurations of the humeral head implant system of FIG. 29.

FIGS. 37A-37E illustrate various configurations of the humeral head implant system of FIG. 34.

DETAILED DESCRIPTION

Figure 1:
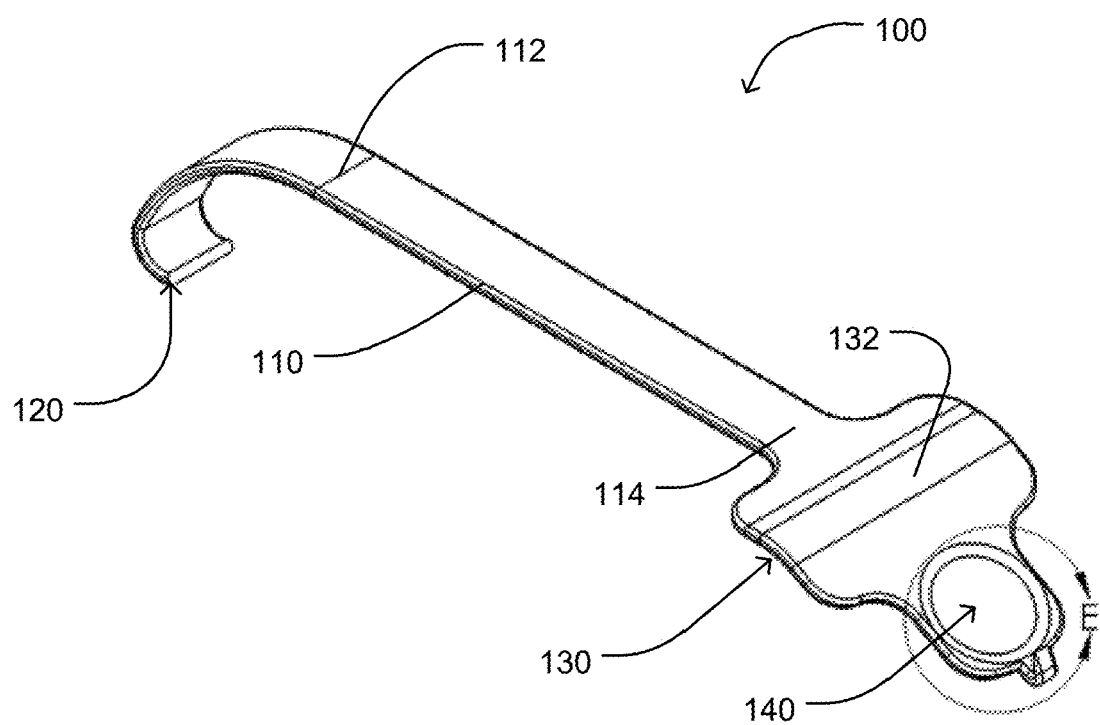
FIG. 1 is an isometric view of an embodiment of a humeral head retractor device.

The following detailed description and the appended drawings describe and illustrate various shoulder arthroplasty retractor systems, methods, and components. The description and drawings are provided to enable one of skill in the art to make and use one or more systems and/or components, and/or practice one or more methods. They are not intended to limit the scope of the claims in any manner.

The use of "e.g." "etc.," "for instance," "in example," and "or" and grammatically related terms indicates non-exclusive alternatives without limitation, unless otherwise noted. The use of "optionally" and grammatically related terms means that the subsequently described element, event, feature, or circumstance may or may not be present/occur, and that the description includes instances where said element, event, feature, or circumstance occurs and instances where it does not. The use of "attached" and "coupled" and grammatically related terms refers to the fixed, releasable, or integrated association of two or more elements and/or devices with or without one or more other elements in between. Thus, the term "attached" or "coupled" and grammatically related terms include releasably attaching or fixedly attaching two or more elements and/or devices in the presence or absence of one or more other elements in between. As used herein, the terms "proximal" and "distal" are used to describe opposing axial ends of the particular elements or features being described in relation to anatomical placement.

In existing solutions, shoulder arthroplasty can result in long recovery times due to how the rotator cuff is removed in order to perform the procedure. The present disclosure relates to devices, systems, and methods for improving shoulder arthroplasty while preventing damage to the rotator cuff, such as by using instruments that can position the humerus and glenoid at an accessible orientation for implant installation without cutting the rotator cuff. The present disclosure also relates to devices, systems, and methods for improving shoulder arthroplasty while preventing damage to the rotator cuff, such as by using humeral head implant systems that can be manipulated and implanted more easily and with less impact on the anatomy of the patient.

A. Rotator Cuff Sparing Devices and Methods

In some embodiments, retractor devices are used to position the humerus and glenoid at an accessible orientation for implant installation. The retractor devices are also used to block anatomical structures from impeding the view of the humeral head and glenoid cup during implant preparation and installation. The retractor devices have angled shaft and grip bodies that avoid anatomy and enable orientation to torque creating lift, pull, and push forces on the anatomy. The retractor devices have teeth or other engagement structures to grip bone and maximize contact area with retractor surfaces to provide improved torque at the patient orientation angles. Additionally, the retractor devices have specific offset distances for matching humerus and glenoid structures to allow torsion on hard bone surfaces for achieving implant preparation view and access.

Figure 2:
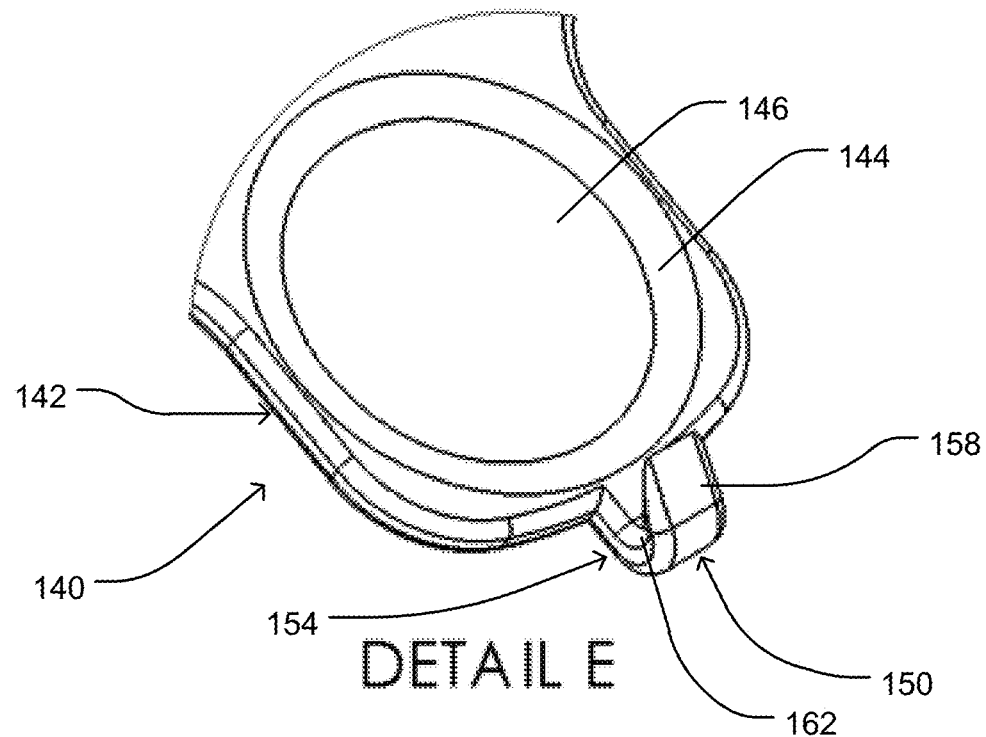
FIG. 2 is a detail view of an embodiment of a grip feature of the humeral head retractor device of FIG. 1.
Figure 3:
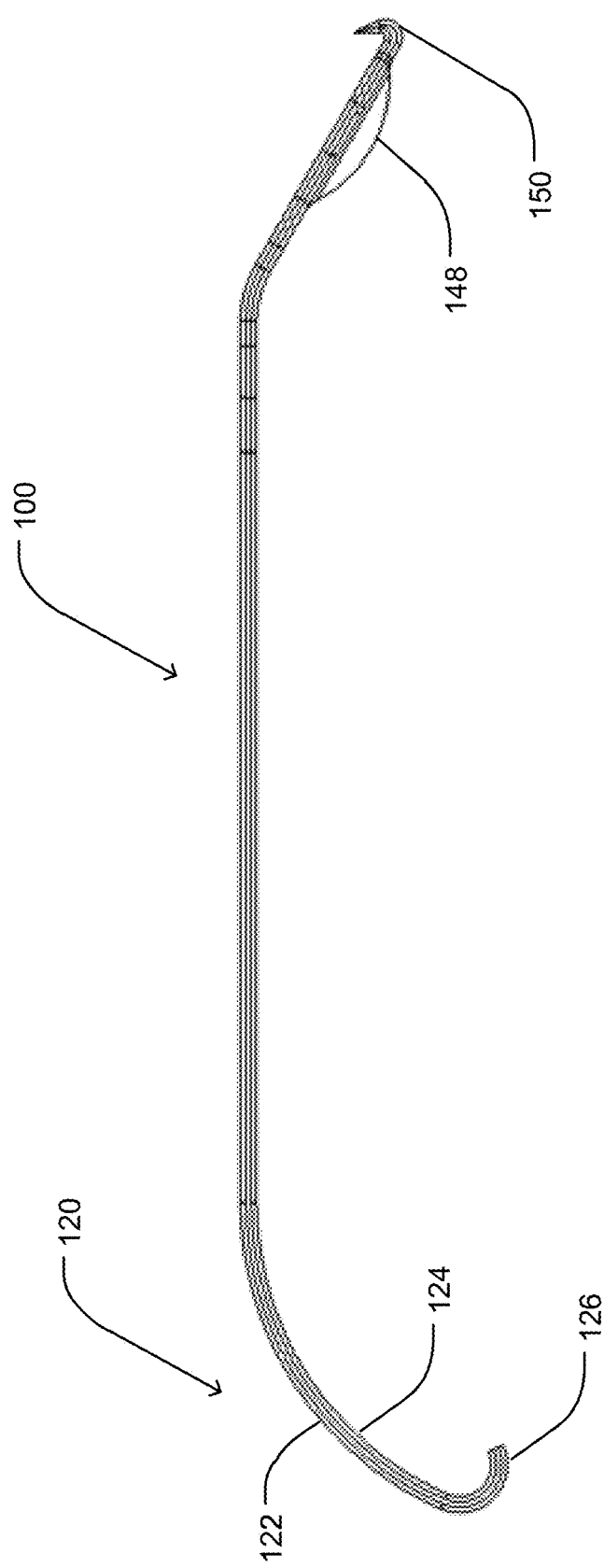
FIG. 3 is a side view of an embodiment of the humeral head retractor device of FIG. 1.

Referring now to FIGS. 1-3, a humeral head retractor device 100 is illustrated in accordance with one embodiment. The humeral head retractor can be configured to lift and retract the humeral head to expose bone structures in and around the humeral head for shoulder arthroplasty procedures. The humeral head retractor device 100 includes a body 110 extending from a first body end 112 to a second body end 114, a handle 120 extending from the first body end 112, a plate 130 extending from the second body end 114, and a retractor 140 extending from an opposite end of the plate 130 from the second body end 114.

The body 110 can define a length from the first body end 112 to the second body end 114. The length can be approximately 8 inches. The length can be selected based on factors including control of manipulation of the retractor 140 (e.g., control over the retractor 140 may increase as the length decreases) and/or a force required to be applied by the retractor surface 140 to retract a humeral head (e.g., the force that can be applied increases as a function of the length).

The handle 120 includes a first handle surface 122 and a second handle surface 124 opposite the first handle surface 122. In some embodiments, the handle 120 includes a handle end 126. The handle end 126 is shown to define an arc length of at least ninety degrees (e.g., relative to a longitudinal axis of the handle 120). The first handle surface 122, second handle surface 124 and/or the handle end 126 can provide surface(s) for receiving tools, or a hand of a user, for manipulating the humeral head retractor device 100. For example, the second handle surface 124 can receive a force applied against the second handle surface 124, and in response, the retractor surface 124 can be translated in a direction corresponding to the force applied against the second handle surface 124. In some embodiments, an arc length defined from the first end 112 to a terminal end of the handle end 126 is at least one-hundred twenty (120) degrees, such that a hand or manipulation device can be supported along the second handle surface 124 and used to manipulate the humeral head retractor device 100.

The plate 130 connects the body 110 to the retractor surface 150. As shown in FIG. 1, the plate 130 has a greater width than the body 110 (e.g., the plate 130 extends past the body 110 on either side of the body 110 in a direction transverse to a longitudinal axis of the body 110). As such, the plate 130 can have a plate surface 132 that is wider than the body 110, such that manipulation of the humeral head retractor device 100 applies force via the plate surface 132 to move tissue in a vicinity of the head of the humerus.

The retractor 140 is configured to engage and manipulate the head of the humerus. The retractor 140 can include a retractor surface 142 that extends from the plate 130. The retractor surface 142 can be shaped to engage the head of the humerus. For example, the retractor surface can include a first engagement surface 144 and a second engagement surface 146. The first engagement surface 144 and second engagement surface 146 extend away from (e.g., curve away from, provide an indent in the retractor surface 142, etc.) a plane defined by the retractor surface 142, terminating in an outer engagement surface 148 as shown in FIG. 3. When manipulated, the retractor 140 can be slid underneath the humeral head to engage (e.g., hook, attach to, secure, etc.) an opposite side of the head (e.g., opposite relative to a direction from which the retractor 140 is moved towards the humeral head), such as to pull the humeral head into position. The first engagement surface 144 and second engagement surface 146 can be configured to receive the humeral head (e.g., a volume of the humeral head fits into the space defined by the first engagement surface 144 and second engagement surface 146).

In some embodiments, the first engagement surface 144 and/or the second engagement surface 146 define a dimension (for example, a diameter) corresponding to a corresponding dimension (for example, a diameter) of the head of the humerus. For example, the diameter defined by the first engagement surface 144 can be within a threshold tolerance (e.g., 1%, 5%, 10%, 20%) of the diameter of the head of the humerus. In some embodiments, a plane defined by the second engagement surface 146 is oriented at an angle relative to the first engagement surface 144 (e.g., oriented at an obtuse angle), which may provide multiple engagement features in a single device such that the humeral head retractor device 100 can be used to manipulate heterogeneously shaped humeral heads.

The retractor 140 includes a retractor engagement feature 150. The retractor engagement feature 150 is configured to engage the head of the humerus. In some embodiments, the retractor engagement feature 150 is configured to engage (e.g., grip, hook, restrict motion of, apply force against, etc.) the humeral head. For example, as the humeral head is received in the retractor surface 142, the retractor engagement feature 150 can be positioned on a backside surface of the humeral head (e.g., the retractor engagement feature 150 can engage the humeral head at a greater distance from the retractor surface 142 relative to a retractor device that does not include engagement surfaces 144, 146 as shown in FIG. 2). In some embodiments, the plate surface 132 of the plate 130 provides increased surface area to retract and protect the deltoid muscle.

The retractor engagement feature 150 extends from the retractor 140 on an opposite side of the retractor from the plate 130. The retractor engagement feature 150 can include a first retractor portion 154 that extends from the retractor surface 142. The first retractor portion can define a width that is less than a width of the retractor surface 142 (e.g., less than half a width of the retractor surface 142), which may provide greater precision in manipulating the retractor engagement feature 150 relative to manipulation of other components of the humeral head retractor device 100. The retractor engagement feature 150 can include a second retractor portion 158 that extends from the first retractor portion 154. The second retractor portion 158 can be oriented at an angle relative to the first retractor portion 154 (e.g., an angle of approximately 90 degrees), such that together the first retractor portion 154 and the second retractor portion 148 define a curved (e.g., hook-shaped) component for engaging the humeral head. The first retractor portion 154 and second retractor portion 158 can define an inner engagement surface 162 which contacts and engages (e.g., frictionally engages) the humeral head.

Figure 4:
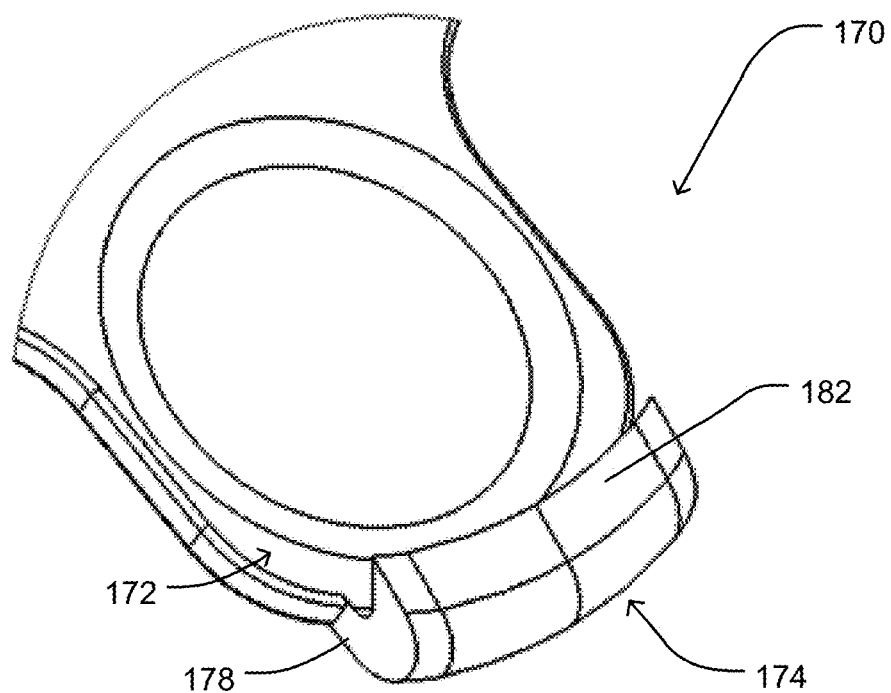
FIG. 4 is a detail view of an embodiment of a grip feature of the humeral head retractor device of FIG. 1.

Referring now to FIG. 4, a retractor 170 of a humeral head retractor device 100 is shown in accordance with one embodiment. The retractor 170 can be similar to the retractor 140, with the exception of features relating to the retractor engagement feature as described below.

The retractor 170 includes a retractor engagement feature 174. The retractor engagement feature 174 includes a first retractor portion 178 extending from a retractor surface 172 of the retractor 170 and a second retractor portion 182 extending from the first retractor portion 178, the second retractor portion 182 being oriented at an angle relative to the first retractor portion 178 (e.g., an angle of approximately ninety degrees). Relative to the retractor engagement feature 150 of FIGS. 1-3, the first retractor portion 178 and second retractor portion 182 define a greater width (e.g., a width that is between 50% and 100% of a width of the retractor surface 172). The relatively greater width may enable a user to more easily separate the humeral head from nearby tissue, such as by increasing surface area of the retractor engagement feature 174 (e.g., the greater surface area may facilitate retracting and protecting a deltoid muscle).

Figure 5:
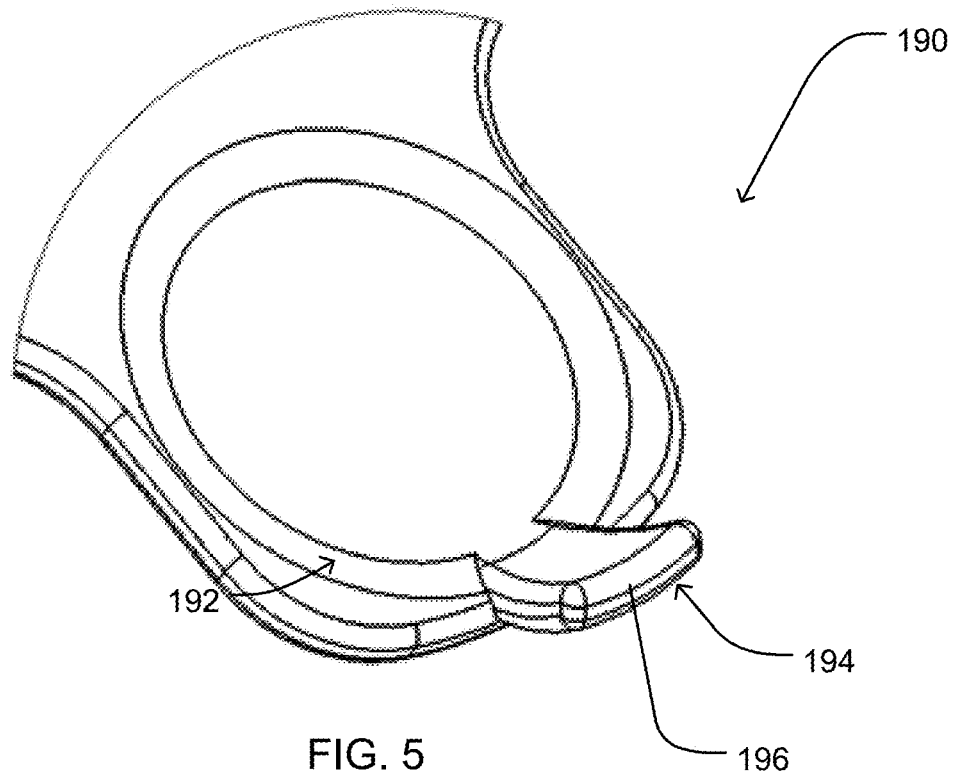
FIG. 5 is a detail view of an embodiment of a grip feature of the humeral head retractor device of FIG. 1.

Referring now to FIG. 5, a retractor 190 of a humeral head retractor device 100 is shown in accordance with one embodiment. The retractor 190 can be similar to the retractors 140, 170, with the exception of features relating to the retractor engagement feature as described below.

The retractor 190 includes a retractor engagement feature 194. The retractor engagement feature 194 defines a width that is less than a width of a retractor surface 192 of the retractor 190 (e.g., less than one half of the width of the retractor surface 192). The retractor engagement feature 194 does not curve or hook as much as the retractor engagement feature 150 or the retractor engagement feature 174. For example, the retractor engagement feature 194 can have a curvature such that an angle defined by a point at which the retractor engagement feature 194 intersects the retractor surface 192, a terminal end 196 of the retractor engagement feature 194, and another point along the retractor engagement feature 194 is greater than ninety degrees. The terminal end 196 can be relatively blunt (e.g., have a greater depth in a direction transverse to the curvature direction) as compared to ends of the retractor engagement features 150, 174, so that for poor quality bone, the retractor 190 does not hook into the bone and cause excessive compression that could damage the surface of the bone during exposure.

Figure 6:
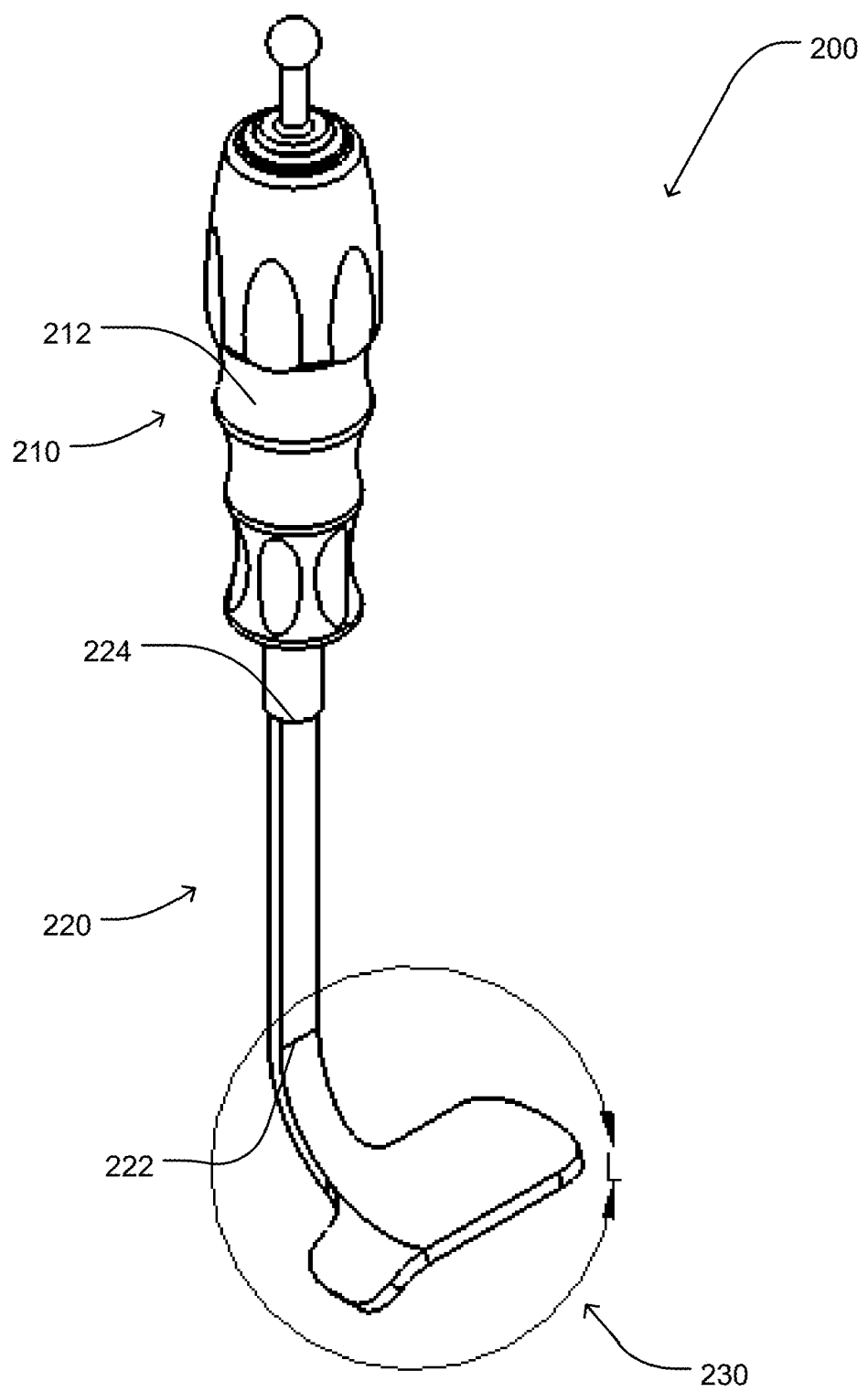
FIG. 6 is an isometric view of an embodiment of a humerus lift device.
Figure 7:
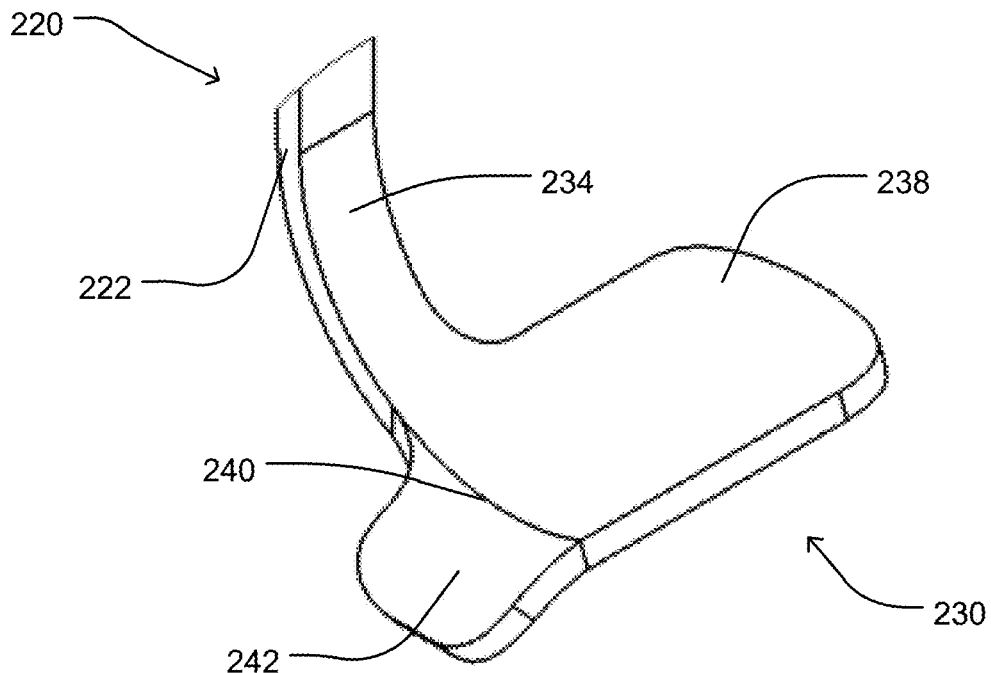
FIG. 7 is a detail view of an embodiment of an attachment feature of the humerus lift device of FIG. 6.

Referring now to FIGS. 6-8, a humerus lift device 200 is shown in accordance with one embodiment. The humerus lift device 200 is configured to lift and support the humerus, such as by following a contour of the humerus to slide underneath the humerus. In some embodiments, the humerus lift device 200 (or components thereof) defines a contoured profile matching a contour of the humerus, such that the humerus lift device 200 may be inserted in a low-profile orientation offset from the humerus. The humerus lift device 200 can be configured to make contact with a transition from the humeral head to a shaft adjacent to the humeral head, which can assist with exposure and prevent fracture when the humeral head is osteomized.

As shown in FIG. 6, the humerus lift device 200 includes a handle 210. The handle 210 can define a cylindrical shape with grip members 212 that allow the handle 210 (and thus the humerus lift device 200) to be both rotated and translated as the handle 210 is manipulated. The humerus lift device 200 includes a body 220 extending from a first end 222 to a second end 224. The handle 210 extends from the second end 224 of the body 220. The humerus lift device includes a lift member 230 that extends from the first end 222 of the body 220. In some embodiments, the handle 210 is configured to couple (e.g., mate, engage, attach to) a universal hospital bed lift/traction system, to allow for pulling the humerus at a desired height and angle for optimum orientation.

In some embodiments, the lift member 230 is configured to follow a contour of a bone (e.g., the humerus), such that manipulation of the humerus lift device 200 allows for manipulation (e.g., lifting, supporting, etc.) of the humerus by the lift member 230. The lift member 230 can include an extension 234 extending from the body 220 at the first end 222. The extension 234 can have a curved shape (e.g., the extension 234 can define a curvature less than or equal to ninety degrees). The lift member 230 can include a first lift portion 238 that extends from the extension 234 in a direction transverse to a longitudinal axis of the body 220. For example, the first lift portion 238 can be positioned in a plane that is transverse to a longitudinal axis of the body 220.

Figure 8A:
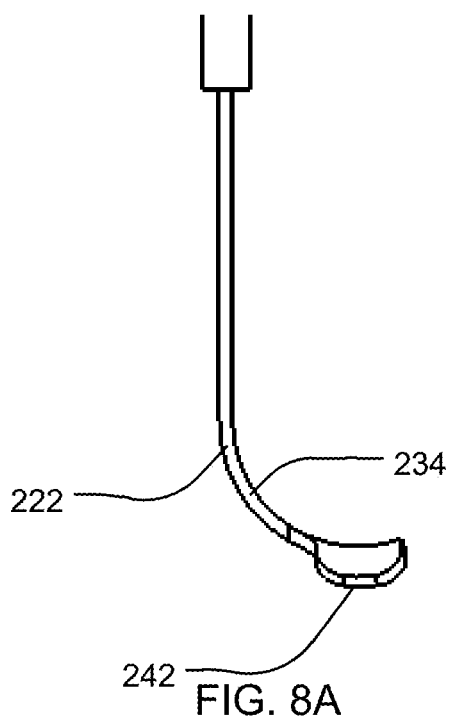
FIG. 8A is a side view of an embodiment of the attachment feature of FIG. 7.

As shown in FIG. 8A, the first lift portion 238 can have a curvature shaped to match a curvature of the humerus. For example, the first lift portion 238 can have a radius of curvature in a direction outwards from the extension 234 that is within a threshold or tolerance of a curvature of the humerus (e.g., within 1%, within 5%, within 10%). As the humerus lift device 200 is manipulated to be slid along the humerus, the first lift portion 238 can thus conform to the humerus, guiding the movement of the humerus lift device 200.

Figure 8B:
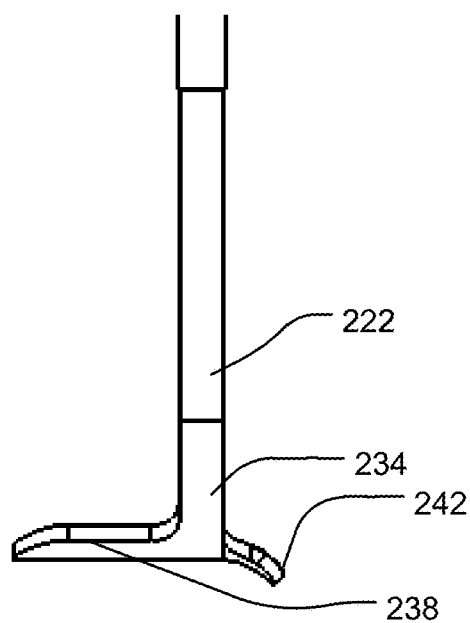
FIG. 8B is a front view of an embodiment of the attachment feature of FIG. 7.

The lift member 230 can include a second lift portion 242. The second lift portion 242 extends from a first end 240 of the first lift portion 238. The second lift portion 242 can be tilted relative to the first lift portion 238. For example, the second lift portion 242 (or a longitudinal axis thereof) can be located in a plane that is at an angle relative to a plane (or a longitudinal axis thereof) that the first lift portion 238 is located in. As shown in FIGS. 7, 8A, and 8B, the angle can be obtuse (e.g., greater than 90 degrees and less than 180 degrees; greater than 120 degrees and less than 180 degrees; greater than 150 degrees and less than 180 degrees).

The angle at which the second lift portion 242 is oriented relative to the first lift portion 238 can be selected such that the second lift portion 242 maintains a low profile, yet also makes contact at the transition from the humerus to prevent fracture of the humerus. For example, the second lift portion 242 can be oriented at an angle relative to the first lift portion 238 such that when the first lift portion 238 contacts the humerus, the second lift portion 242 is positioned away from the humerus less than a threshold distance while the first lift portion 238 contacts and is slid along the humerus so that the second lift portion 242 does not damage or interfere with tissue in the vicinity of the humerus. The threshold distance can be defined as the shortest distance from a distal end of the second lift portion 242 to the humerus, and can be a function of a thickness of the first lift portion 238 (e.g., less than 10 times the thickness of the first lift portion 238, less than 5 times the thickness of the first lift portion).

In some embodiments, such as shown in FIG. 8A, the second lift portion 242 has a curvature. The curvature can be shaped to match a curvature of the humerus. The curvature of the second lift portion 242 may be similar to the curvature of the first lift portion.

Figure 9:
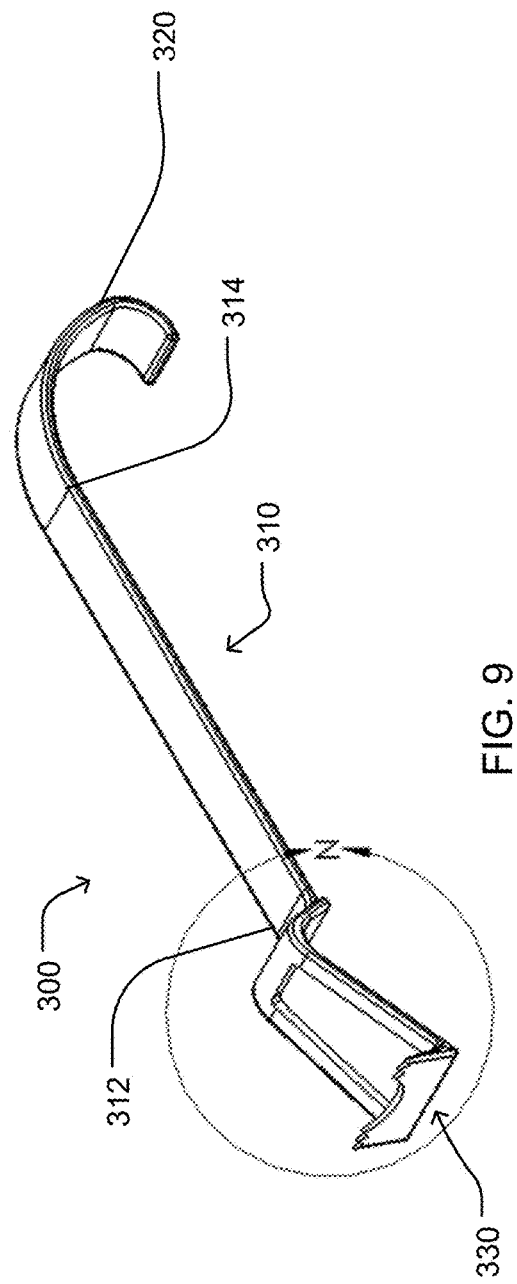
FIG. 9 is an isometric view of an embodiment of a glenoid retractor device.
Figure 10:
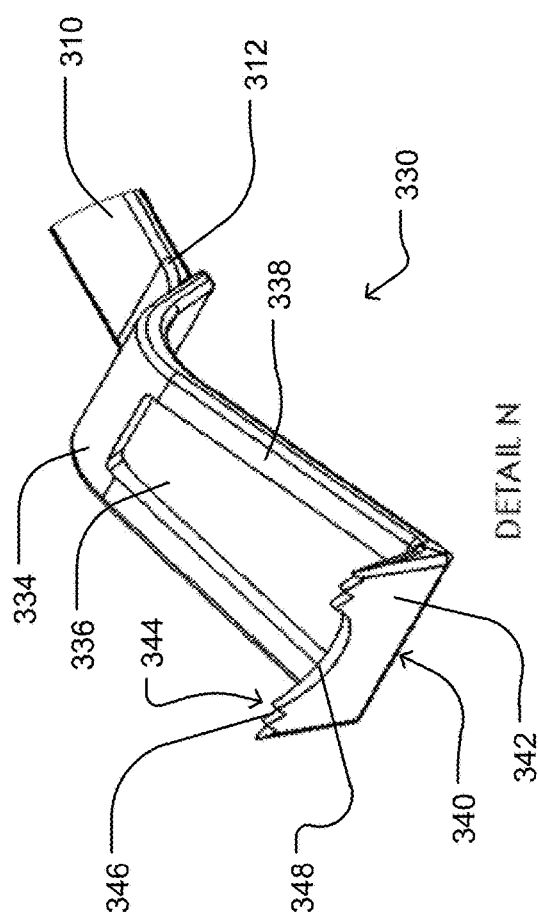
FIG. 10 is a detail view of an embodiment of an attachment feature of the glenoid retractor device of FIG. 9.

Referring now to FIGS. 9-11, a glenoid retractor device 300 is shown in accordance with one embodiment. The glenoid retractor device 300 can be configured to attach underneath a glenoid cavity with adequate offset to avoid interfering the glenoid when lifting for exposure.

The glenoid retractor device 300 include a body 310 that extends from a first end 312 to a second end 314. The glenoid retractor device 300 can include a handle 320 that extends from the second end 314 of the body 310. The handle 320 can be similar in structure and function to the handle 120 of the humeral head retractor device 100, such as by providing surfaces for forces applied against the handle 120 to cause the glenoid retractor device 300 to be manipulated.

The glenoid retractor device 300 can include a lift surface 330 extending from the first end 312 of the body 310. The lift surface 330 can be configured to engage a portion of a subject in or around a glenoid cavity. The lift surface 330 can include a first surface portion 334 extending from the first end 312 of the body 310. The first surface portion 334 can be shaped to curve away from the body 310 (e.g., such that the first surface portion 334 is oriented in a plane transverse to the body 310).

The lift surface 330 can include a second surface portion 338. The second surface portion 338 can be shaped to curve away from the first surface portion 334 (e.g., such that the second surface portion 338 is oriented in a plane transverse to the first surface portion 334). The second surface portion 338 can define an opening 336, allowing for visibility through the second surface portion 338 and/or instruments to be passed through the second surface portion 338.

The second surface portion 338 can define a first width at a first end adjacent to the first surface portion 334, and a second width opposite the first end, such that the width of the second surface portion 338 increases from the first end to the second end. In some embodiments, by increasing the width of the second surface portion 338 from the first end to the second end, components of the glenoid retractor device 300 that extend from the first end (e.g., the first surface portion 334, the body 310, the handle 320) can be shaped with a relatively lesser width, allowing for a low profile, while components extending from the second end (e.g., an attachment feature 340 as described herein) can be shaped with a relatively greater width, allowing for a greater surface area for manipulating bones in and around the glenoid.

The glenoid retractor device 300 can include an attachment feature 340. The attachment feature 340 can be configured to attach underneath a glenoid cavity. The attachment feature 340 can include an attachment member 342 that extends from the second surface portion 338. The attachment member 342 can extend transverse to the second surface portion 338 (e.g., at an angle of approximately 90 degrees, such as an angle between 60 degrees and 90 degrees). This may allow a bone to be received on the second surface portion 338 and simultaneously supported by the attachment member 342.

In some embodiments, the attachment member 342 terminates in one or more engagement features 344. For example, as shown in FIG. 10, the attachment member 342 terminates in angled members 346 (e.g., ridges, teeth), that may engage a feature of a body of a subject in or around the glenoid cavity to attach the glenoid retractor device 300. The attachment member 342 can also terminate in an attachment receiving surface 348. The attachment receiving surface 342 can be shaped to match a shape of a bone structure of the patient in or around the glenoid cavity. For example, the attachment receiving surface 348 can define a radius of curvature that matches a radius of curvature of the bone structure (e.g., the radius of curvature is within a threshold or tolerance of a curvature of the bone structure, such as being with 1%, within 5%, within 10%). The attachment receiving surface 348 can facilitate manipulation of the glenoid retractor device 300, such as by aligning the glenoid retractor device 300 to the bone structure, allowing the angled members 346 to attach in the correct location.

Figure 12:
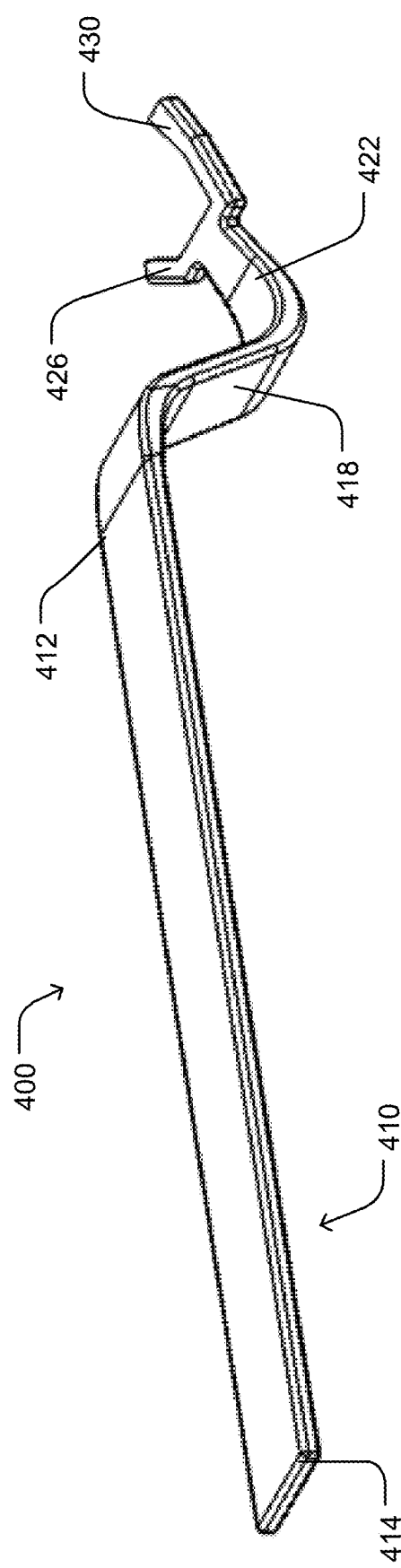
FIG. 12 is an isometric view of an embodiment of a supraglenoid tubercle retractor device.

Referring now to FIG. 12, a glenoid retractor device 400 is shown in accordance with one embodiment. The glenoid retractor device 400 can be similar to the glenoid retractor device 300, with the exception of the attachment features as described below.

As shown in FIG. 12, the glenoid retractor device 400 includes a body 410 (but does not include a handle distinct from the body 410) extending from a first end 412 to a second end 414. A first surface portion 418 extends from the first end 412 of the body 410. The first surface portion 418 can be angled relative to the body 410 such that the first surface portion 418 curves away from the body 410.

An attachment feature 422 extends from the first surface portion 418. The attachment feature 422 can be angled relative to the first surface portion 418 such that the attachment feature 422 avoids the acromion and coracoid process to increase access to bony structure underneath the glenoid cavity for additional glenoid exposure (see FIGS. 15, 16). For example, the attachment feature 422 can define an angle relative to the first surface portion of approximately 90 degrees (e.g., between 75 and 105 degrees, between 85 and 95 degrees, between 90 and 100 degrees). The attachment feature 422 includes a first attachment member 426 and a second attachment member 430. The first attachment member 426 extends a lesser distance than the second attachment member 430, such that the attachment feature 422 conforms to a shape of the glenoid when in use (e.g., see FIGS. 15, 16).

In various embodiments, devices such as the humeral head retractor device 100, the humerus lift device 200, the glenoid retractor device 300, and/or the glenoid retractor device 400 can include various angles for handles, and various grips (e.g., for coupling to a universal traction system), to enable manipulation of the devices at various angles depending on an anatomy of the patient, including features of a patient to avoid during an operation.

Figure 13:
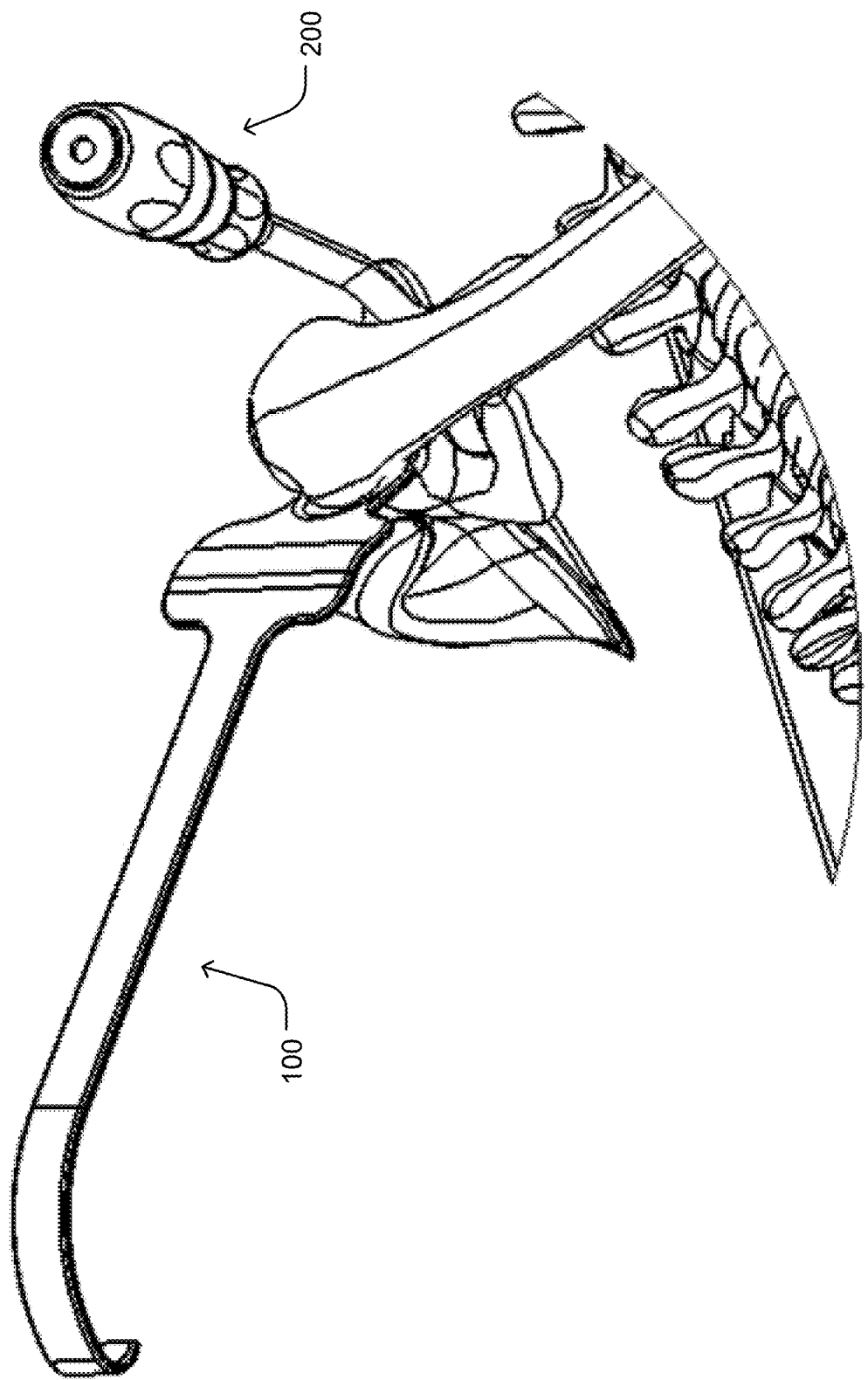
FIG. 13 is an isometric assembly view of an embodiment of humeral head instruments.
Figure 14:
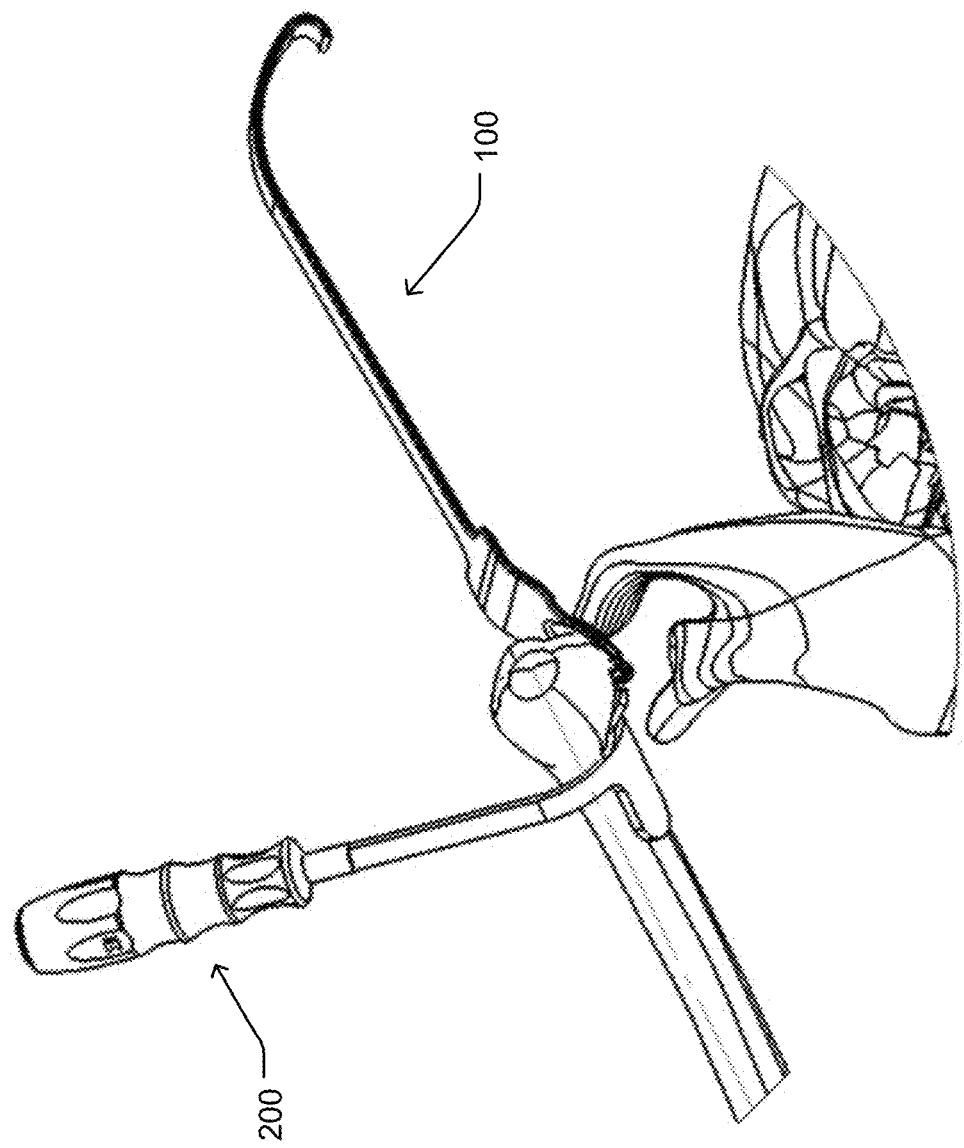
FIG. 14 is a rotated isometric assembly view of an embodiment of the humeral head instruments of FIG. 13.

Referring now to FIGS. 13-14, an isometric assembly view of a humeral head retractor device 100 and a humerus lift device 200 is shown in accordance with one embodiment. The devices are being used to retract a humeral head of a patient. Angles and orientations of approach for the devices can be selected to minimize interference with an anatomy of the patient, such as to avoid contacting bones other than the humerus or to avoid the rotator cuff.

Figure 15:
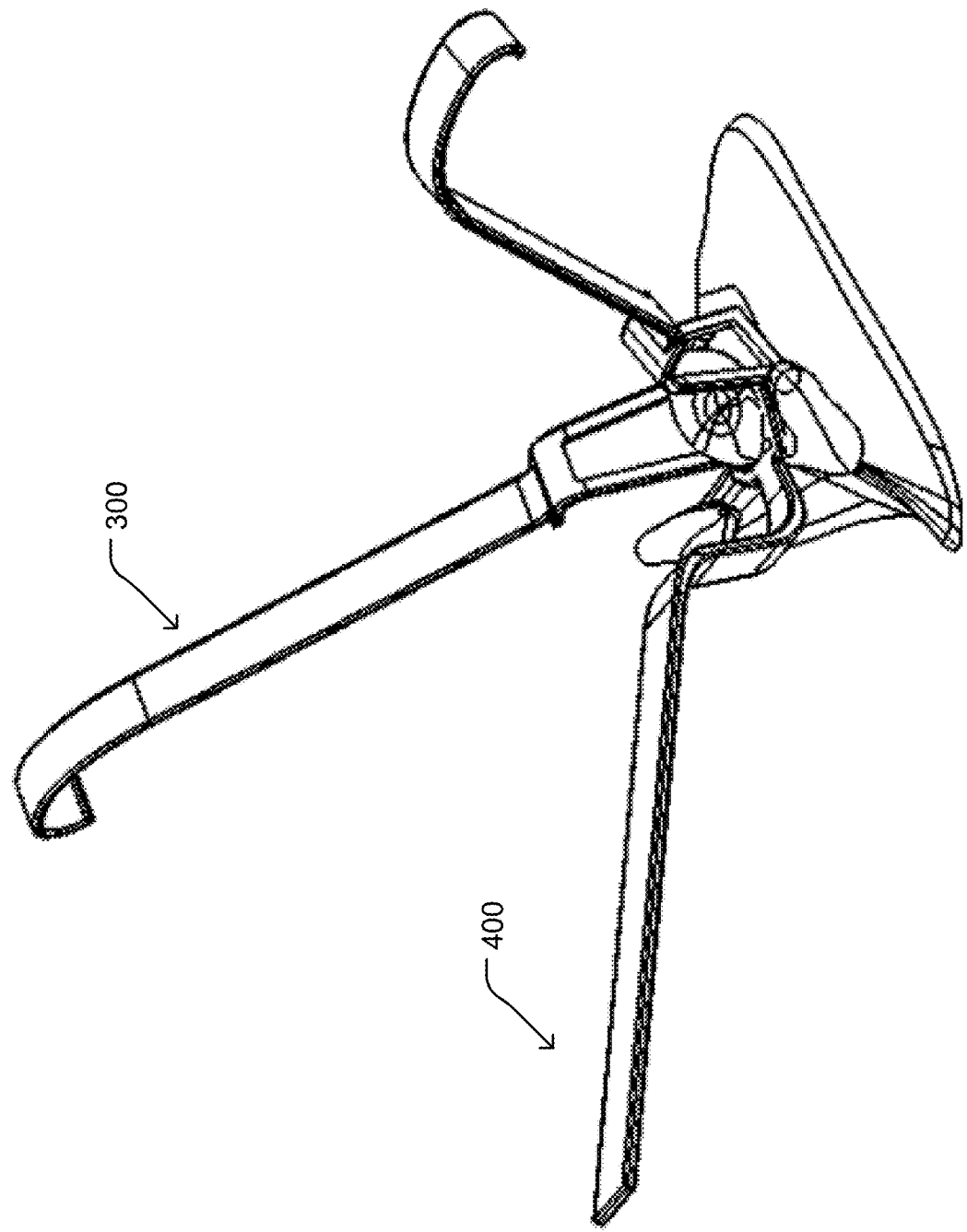
FIG. 15 is an isometric assembly view of an embodiment of glenoid instruments.
Figure 16:
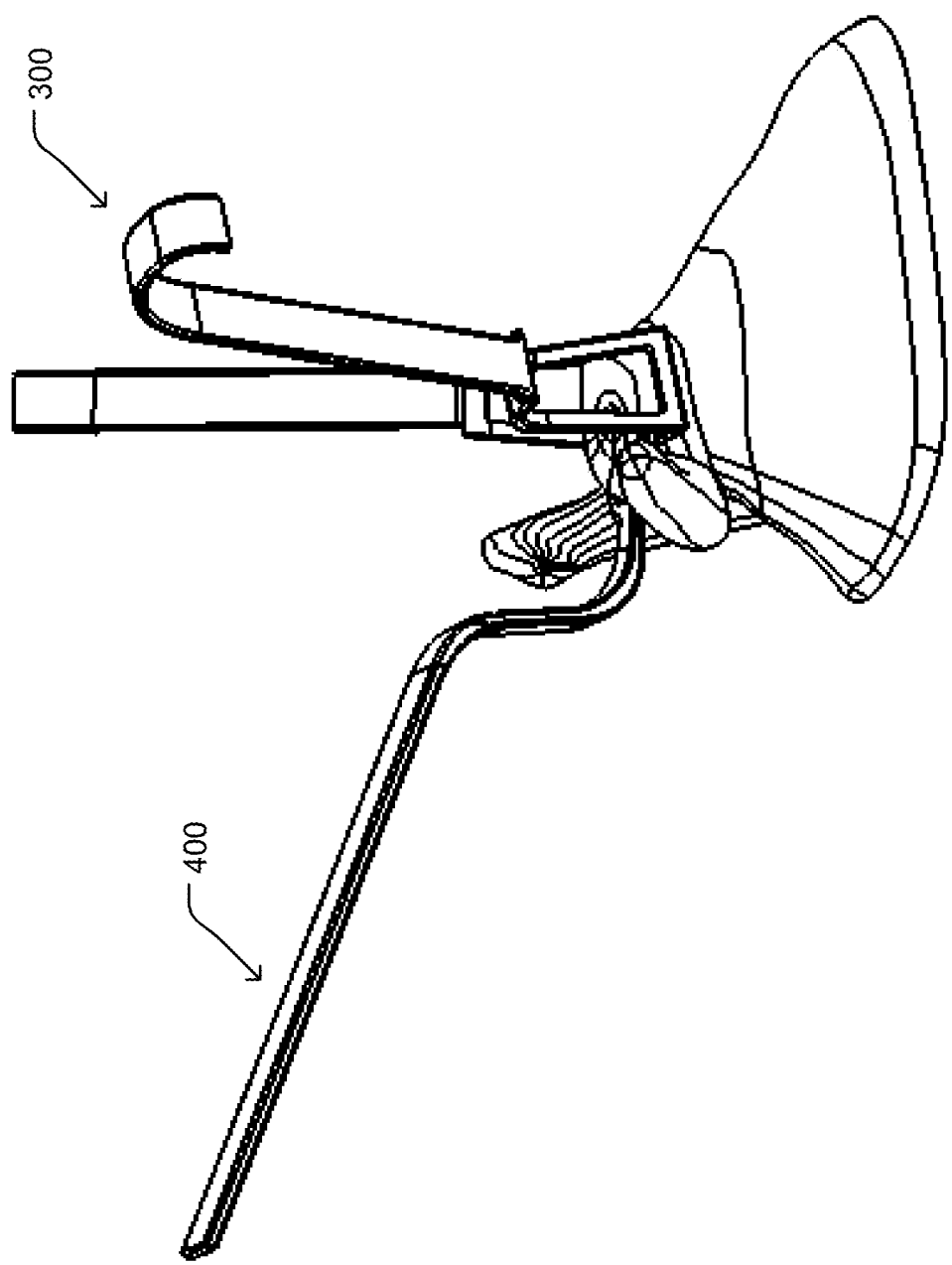
FIG. 16 is a rotated isometric assembly view of an embodiment of the glenoid instruments of FIG. 15.

Referring now to FIGS. 15-16, isometric assembly views of glenoid retractor devices 300, 400 are shown in accordance with one embodiment. The glenoid retractor devices 300, 400 can be attached anterior to a glenoid cavity. The shafts of the devices (e.g., second surface portion 338 of glenoid retractor device 300) can be oriented at an angle of approximately 45 degrees relative to the head of the devices (e.g., an angle defined between the second surface portion 338 and the attachment feature 340 may be greater than or equal to 35 degrees and less than or equal to 55 degrees, greater than or equal to 40 degrees and less than or equal to 50 degrees, greater than or equal to 44 degrees and less than or equal to 46 degrees, etc.). The handle 320 of the glenoid retractor device 300 may extend from the body 310 at an angle of approximately 120 degrees (e.g., greater than or equal to 90 degrees and less than or equal to 150 degrees, greater than or equal to 105 degrees and less than or equal to 135 degrees, greater than or equal to 110 degrees and less than or equal to 130 degrees, etc.). This can allow the handle 320 to be gripped by a user (e.g., a surgical assistant) such that hands of the user are clear of the surgical field (e.g., a line of sight defined between the lift surface 330 and eyes of the user, a surgical camera, or along the body 310 is not blocked or otherwise interfered by the hands of the user). The glenoid retractor device 400 has a double bend (e.g., bends at transitions from the body 410 to the first surface portion 418 and again from the first surface portion 418 to the attachment feature 422), which can allow for retraction of the inferior lip and the superior aspect of the glenoid, to improve glenoid exposure.

Figure 17A:
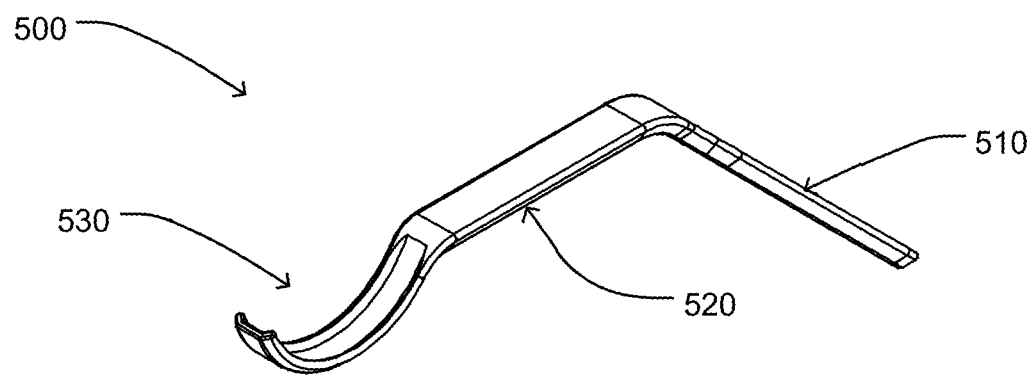
FIG. 17A is a perspective view of an embodiment of a retractor device.
Figure 17B:
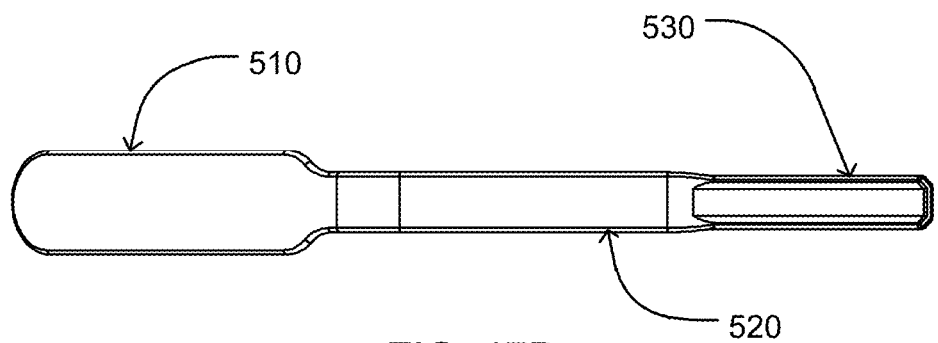
FIG. 17B is a top view of the retractor device of FIG. 17A.
Figure 17C:
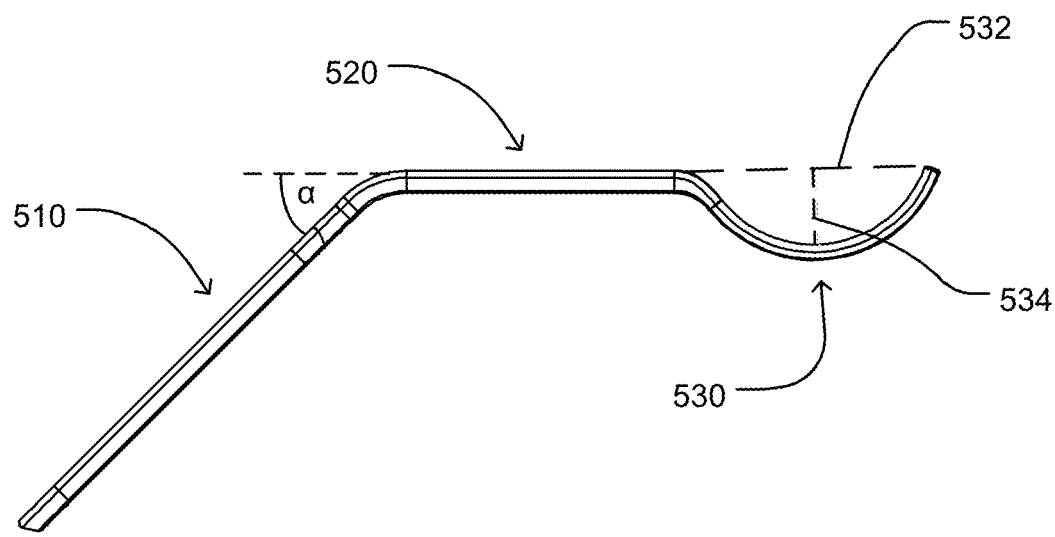
FIG. 17C is a side view of the retractor device of FIG. 17A.

Referring now to FIGS. 17A-17C, a retractor device 500 is illustrated in accordance with one embodiment. The retractor device 500 can be similar to the humeral head retractor device 100 described herein, with the exception of the retractor and handle components as described further below.

As shown in FIGS. 17A-17C, the retractor device 500 includes a handle portion 510, a body portion 520, and a retractor portion 530. The handle portion 510 and the body portion 520 can define an angle α by which the handle portion 510 and body portion 520 are oriented with respect to one another. The angle α can allow a direct line of sight along the retractor device 500 to the retractor portion 530 and the anatomy being manipulated by the retractor portion 530 (e.g., a hand of a user of the retractor device 500 placed on the handle portion 510 will not block, interrupt, or otherwise interfere with a line of sight from the user's eyes to the retractor portion 530 or along the body portion 520 to the retractor portion 530). The handle portion 510 can have a length that corresponds to an expected or average depth of a wound (e.g., approximately 5 inches; greater than or equal to 2 inches and less than or equal to 8 inches; greater than or equal to 4 inches and less than or equal to 6 inches; etc.). The retractor portion 530 can define a curvature that allows for retracting the head of the humerus. The retractor portion 530 can define a span 532 from the body portion 520 to a terminal end of the retractor portion 530 of approximately 2.5 inches (e.g., greater than or equal to 1.5 inches and less than or equal to 3.5 inches; greater than or equal to 2 inches and less than or equal to 3 inches; etc.). The retractor portion 530 can define a radius 534 of approximately 2 to 3 inches (e.g., greater than or equal to 1 inch and less than or equal to 4 inches; greater than or equal to 2 inches and less than or equal to 3 inches; etc.).

Figure 18A:
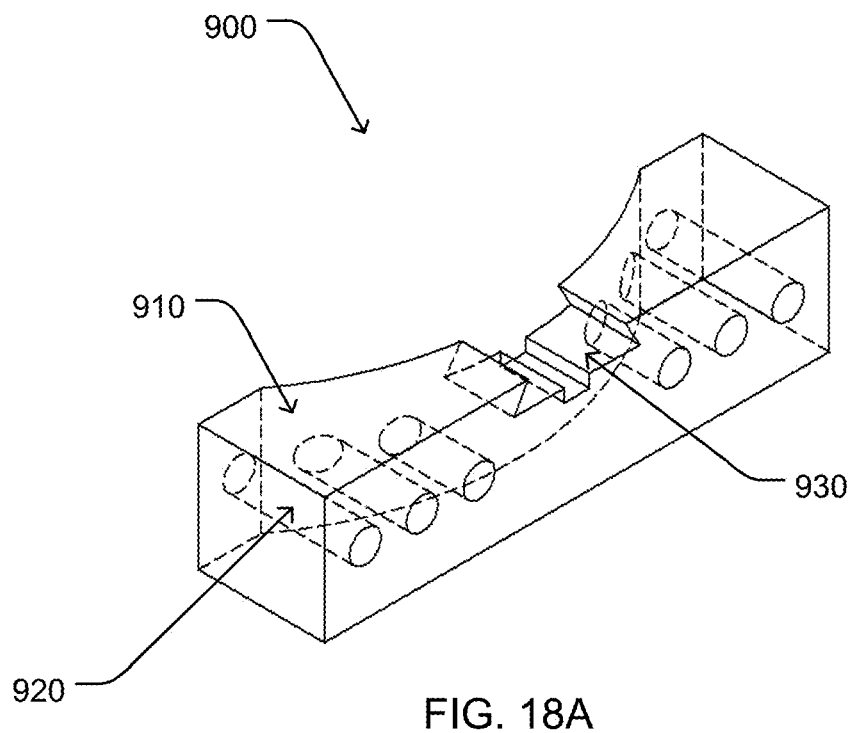
FIG. 18A is a perspective view of an embodiment of a humeral resection guide.
Figure 18B:
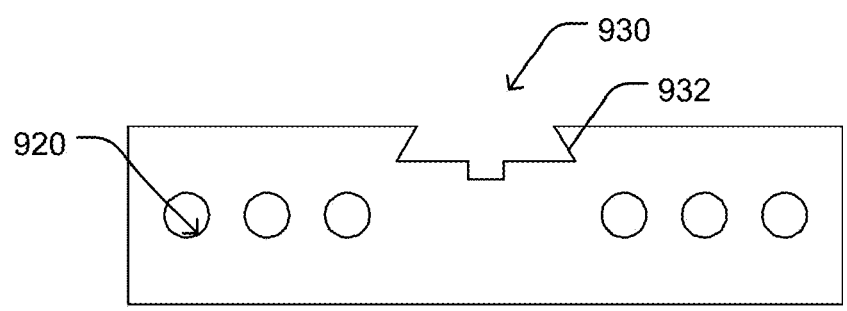
FIG. 18B is a side view of the humeral resection guide of FIG. 18A.

Referring now to FIGS. 18A-18B, a humeral resection guide 900 (e.g., a cutting jig) is illustrated in accordance with one embodiment. The humeral resection guide 900 can provide a flat cutting surface for resection, and unlike existing systems, includes a contact surface for contacting the humeral head so that the humeral head resection guide can fit on a posterior aspect of the humeral head, such as for being braced against the humeral head. The humeral resection guide 900 includes a curved contact surface 910 that can be positioned against the humeral head. The humeral resection guide 900 includes a plurality of channels 920 that can receive pins for pinning the humeral resection guide 900 in place. The humeral resection guide 900 includes an engagement feature 930 (e.g., a slot, a key slot) configured to receive an engagement device (e.g., engagement device 1000 described with reference to FIGS. 22A-22B) for allowing a surgeon or other medical professional performing a shoulder arthroplasty procedure to keep their hands away from the arthroplasty site while manipulating the engagement device, such as the engagement device 1000. The engagement feature 930 can include a pair of engagement walls 932 that extend from the contact surface 920 into an interior of the humeral resection guide 900. A distance between the engagement walls 932 may increase towards the interior of the humeral resection guide 900.

Figure 19A:
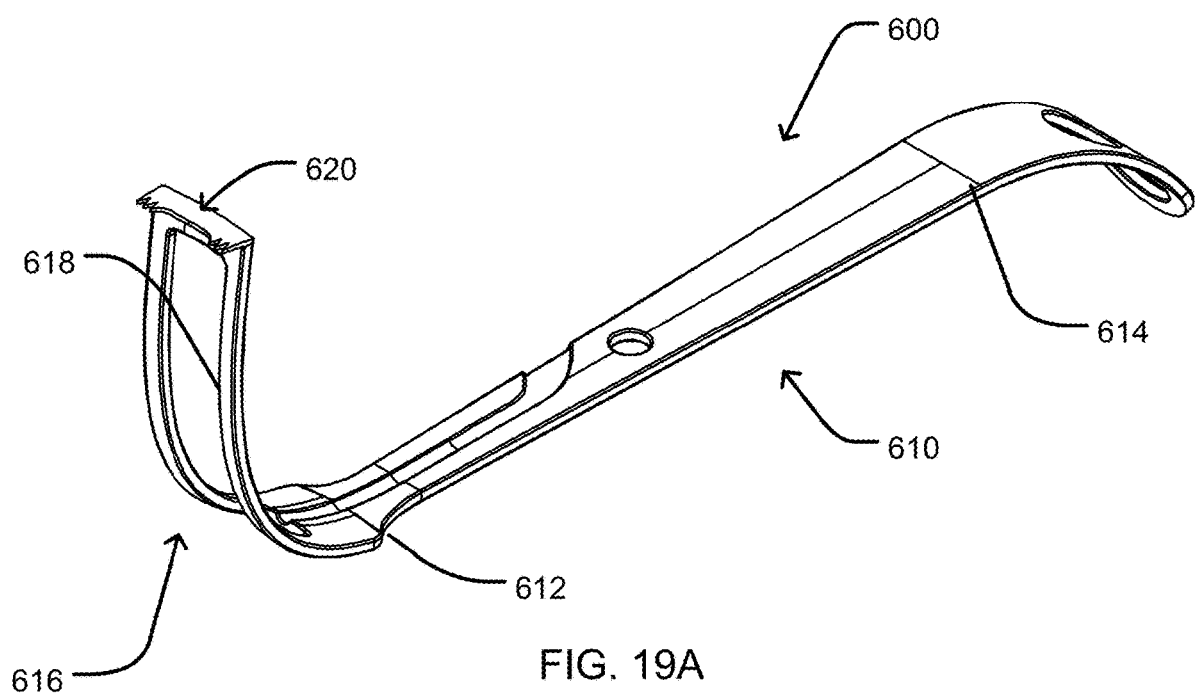
FIG. 19A is a perspective view of an embodiment of a retractor device.
Figure 19B:
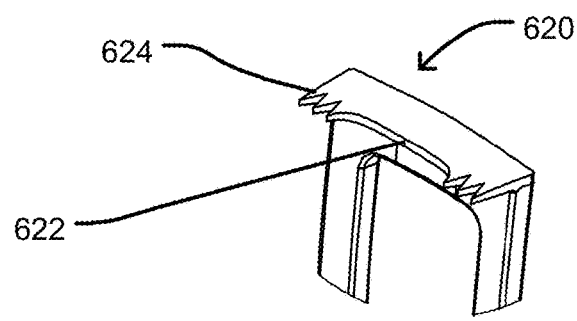
FIG. 19B is a detailed perspective view of a retractor portion of the retractor device of FIG. 19A.

Referring now to FIGS. 19A-19B, a retractor device 600 is illustrated in accordance with one embodiment. The retractor device 600 can be similar to other retractor devices disclosed herein (e.g., glenoid retractor device 300). The retractor device 600 can be configured to retract against the anterior glenoid to improve exposure. The retractor device 600 includes a body 610 that extends from a first end 612 to a second end 614. At the second end 614, the body 610 can define an opening (e.g., a cutout centered in the body 610) allowing for instrumentation to be placed through the opening. The body can have a width of approximately 3 cm (e.g., 3 cm, greater than 2 cm and less than 4 cm, greater than or equal to 2.5 cm and less than or equal to 3.5 cm). The retractor device 600 can include a retractor section 616 extending from the first end 612 of the body 610. The retractor section 616 can define an opening (e.g., a cutout) 618. At a distal end of the retractor section 616 (e.g., an end opposite the first end 612 of the body 610), an offset portion 620 can extend from the retractor section 616. The offset portion 620 can be oriented transverse to the retractor section 616 (e.g., oriented at an angle of approximately 90 degrees). The offset section 620 can terminate in an arc-shaped toothed surface including an arc section 622 positioned between toothed sections 624. The offset section 620 can have a length of approximately 7 mm (e.g., 7 mm). The length can be defined from where the offset section 620 joins the retractor section 616 to where the offset section 620 terminates). The offset section 620 can be placed on a front portion of a socket of the shoulder as the socket is exposed. The arc section 622 can be sized to fit around a lower portion of the glenoid, allowing the toothed portions 624 to be spaced by the arc section 622 and separately engage the glenoid on either side of the lower portion of the glenoid. In some embodiments, the offset section 620 does not include the arc section 622, but instead may have teeth along an entire length of the offset section 620.

Figure 20A:
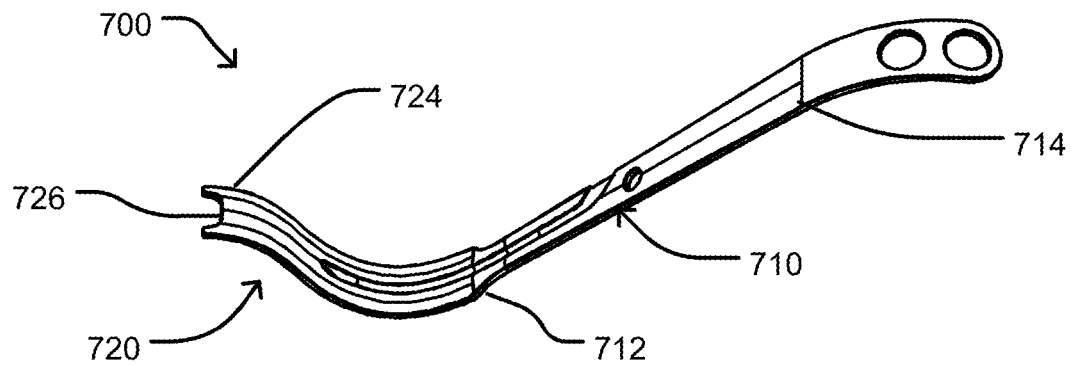
FIG. 20A is a perspective view of an embodiment of a retractor device.
Figure 20B:
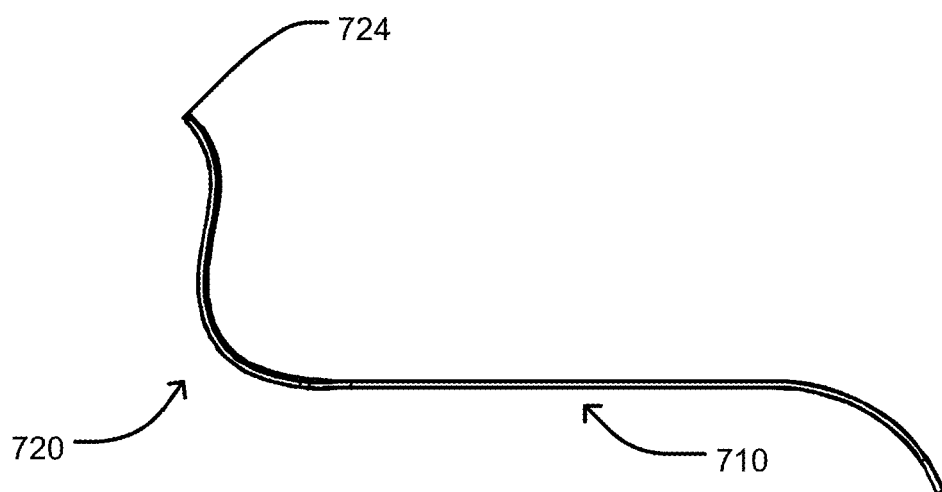
FIG. 20B is a side view of the retractor device of FIG. 20A.
Figure 20C:
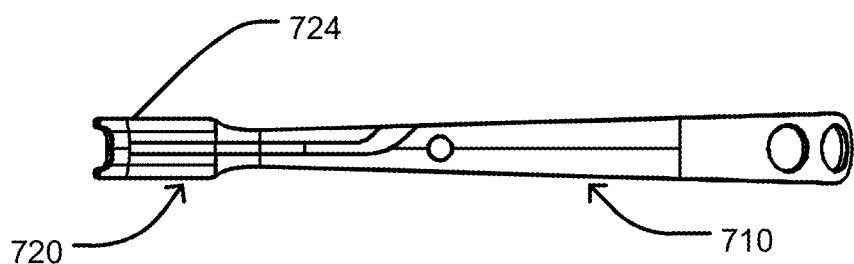
FIG. 20C is a top view of the retractor device of FIG. 20A.

Referring now to FIGS. 20A-20C, a retractor device 700 is illustrated in accordance with one embodiment. The retractor device 700 can be similar to other retractor devices disclosed herein (e.g., humeral head retractor device 100, etc.). The retractor device 700 can be configured to retract the inferior humeral neck, so that the humeral neck and head can be brought close to the rotator cuff split. The retractor device 700 includes a body 710 extending from a first end 712 to a second end 714. The retractor device 700 includes a retractor section 720 extending from the first end 712. The retractor section 720 terminates in a retractor end 724 that defines a curved surface 726 (e.g., U-shaped).

In some embodiments, the retractor end 724 defines a beveled edge that has a soft curve (e.g., having a radius of curvature that is no less than a threshold radius at any given point), which can allow for gentle but strong retraction on the inferior humeral neck. In some embodiments, the retractor end 724 has a length of approximately 3 cm (e.g., 3 cm, greater than 2 cm and less than 4 cm, greater than or equal to 2.5 cm and less than or equal to 3.5 cm). The length of the retractor end 724 can be configured to conform to the inferior humeral neck. In some embodiments, a first portion of the retractor section 720 adjacent to the retractor end 724 curves at an angle of approximately 5 degrees away from the retractor end 724, and a second portion of the retractor section 720 curves at an angle greater than 5 degrees away from the first portion. The retractor end 724 can have a curved edge that retracts a calcar of the humerus. The retractor device 700 can have a curved body, allowing for the surgical field to be clearly seen without obstruction (e.g., a user manipulating the retractor device 700 at the handle of the retractor device 700 does not interrupt a line of sight to the retractor end 724).

Referring now to FIGS. 21A-21B, a retractor device 800 is illustrated in accordance with one embodiment. The retractor device 800 can be similar to other retractor devices disclosed herein (e.g., humeral head retractor device 100, etc.). The retractor device 800 can be configured to fit into the bicipital groove to retract the humeral head for canal preparation for a stemmed implant. The retractor device 800 includes a tip portion 820 located at an end of the retractor device 800. The tip portion 820 can be approximately 4 cm (e.g., 4 cm, greater than 2 cm and less than 6 cm, greater than or equal to 3.5 cm and less than or equal to 4.5 cm). The tip portion 820 can terminate in a flat curved portion 822 (e.g., a beveled portion) of approximately 2 cm in width, so that the tip portion 820 may fit inside a rotator interval and hold the humeral head in place. As such, the tip portion 820 can fit inside the bicipital groove to evert the humerus. The retractor device 800 can be configured to curve away from the shoulder with a gentle curve (e.g., a curve having a radius of curvature less than a threshold radius), which can allow for adequate exposure on the superior humeral head. The tip portion 820 can taper to a terminal end so that the tip portion 820 can avoid large structures that would block the tip portion 820 relative to a tip portion having a more blunt face.

Figure 22A:
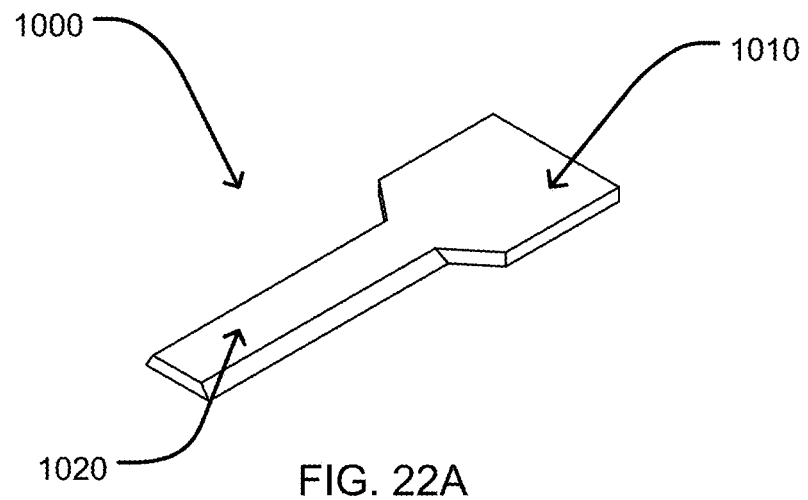
FIG. 22A is a perspective view of an embodiment of an engagement device.
Figure 22B:
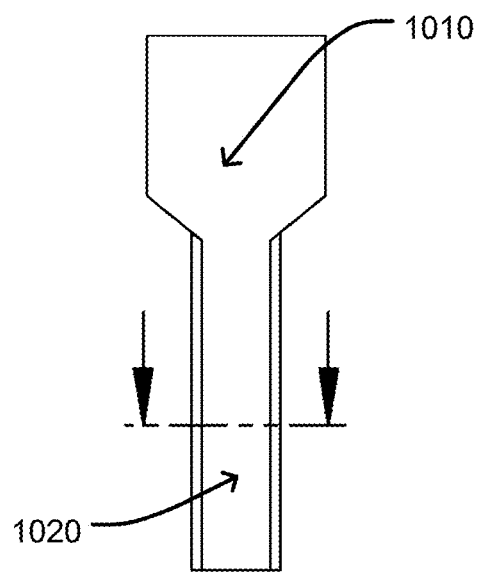
FIG. 22B is a top view of the engagement device of FIG. 22A.
Figure 22C:
FIG. 22C is a sectional view of the engagement device of FIG. 21A and FIG. 21B.
Figure 23:
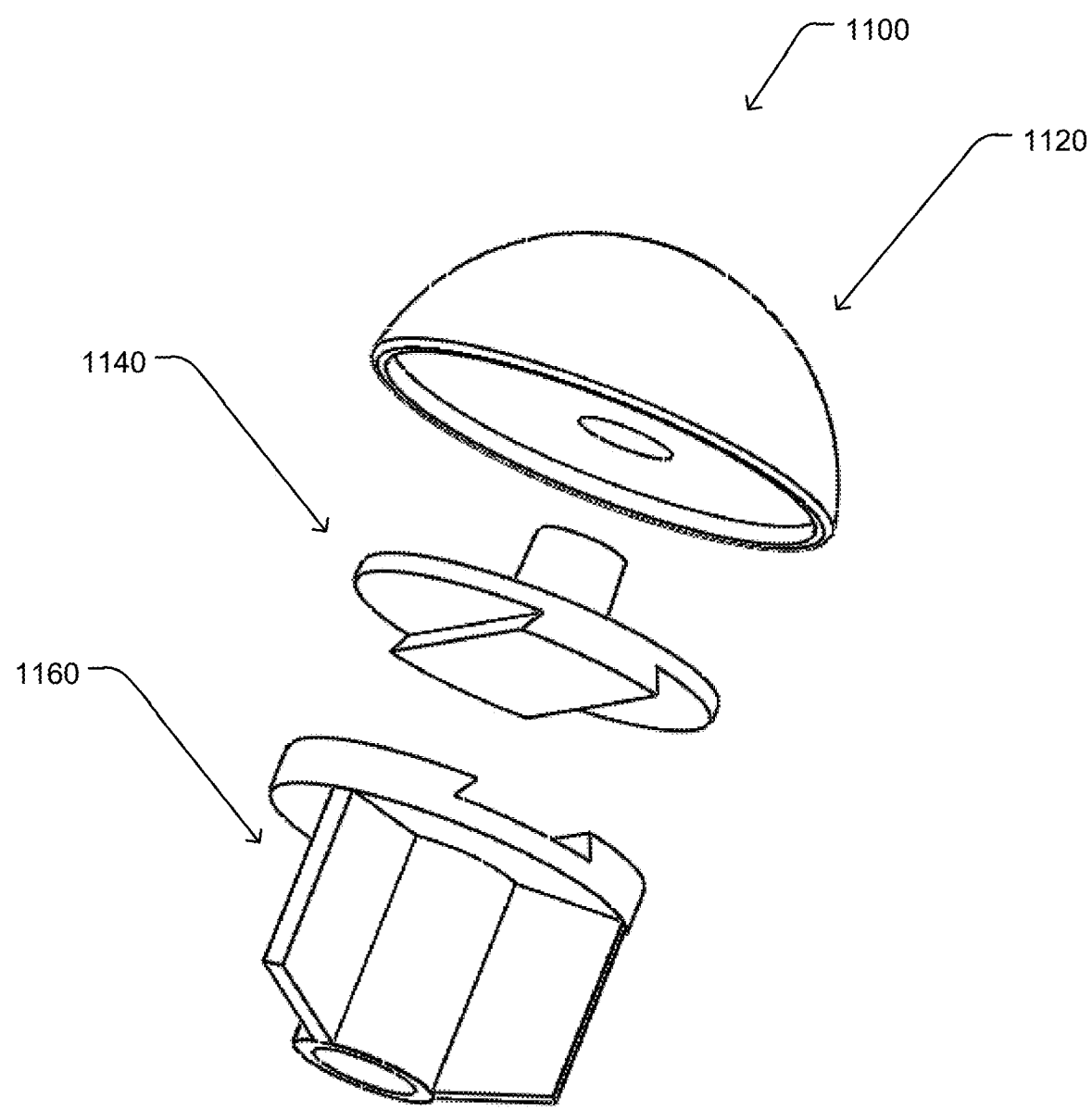
FIG. 23 is an exploded view of an embodiment of a humeral head implant system.

Referring now to FIGS. 22A-22C, an engagement device 1000 (e.g., an insert) is illustrated in accordance with one embodiment. The engagement device 1000 can be configured to engage the engagement feature 930 of the humeral resection guide 900. The engagement device 1000 includes a first portion 1010 that tapers to a second portion 1020. The second portion 1020 can be inserted into the engagement feature 930. For example, the second portion 1020 can terminate in an end surface 1030 that is inserted into or received first by the engagement feature 930. The end surface 1030 can have a similar or identical shape as to an opening defined by the engagement feature 930, such as for allowing a tight fit between the engagement device 1000 and the engagement feature 930. The engagement device 1000 can allow a surgeon or other medical professional performing a shoulder arthroplasty procedure to keep their hands away from the arthroplasty site while manipulating the engagement device 1000, improving line of sight to the arthroplasty site while reducing invasiveness of the arthroplasty procedure. It should also be appreciated that there may not be sufficient space for a surgeon to use their hands to manipulate the humeral resection guide 900 when performing a surgery in this fashion, and as such, the use of the engagement device 1000 enables the surgeon to manipulate the humeral resection guide 900 despite the limited space.

The various apparatuses and systems herein can be used to perform shoulder arthroplasty procedures in a manner that improves over existing procedures by limiting rotator cuff trauma and improving shoulder socket exposure.

In some embodiments of a shoulder arthroplasty procedure, the posterior skin of the shoulder is incised overlying the posterior shoulder joint in line with the deltoid fibers. A retractor device may be used to safely and easily retract and protect the deltoid. For example, the retractor device may have long arms and curved, cupped edges to protect the deltoid. The lower border of the deltoid is identified and dissected free. The deltoid is split in line with its fibers over the apex of the humeral head. The midportion of the humeral head is identified. The rotator cuff is split between the infraspinatus and the teres minor. Two muscular windows are established superior and inferior to the deltoid split. Subsequently, the rotator cuff muscle is dissected down its length both in the deltoid window and the window below it.

The rotator cuff is elevated to slacken it and the muscle is elevated from the underlying capsular tissue. The capsule is released along the labrum and released along the neck of the humerus. The humeral head is then osteotomized. Modified crego retractor devices (e.g., retractor device 500) are placed posterior to the humeral head. The retractor device 500 includes angled arms (e.g., handle 510) that can allow for the humeral head to be directly visualized, creating an assessment of humeral version. Subsequently, a humeral resection guide (e.g., humeral resection guide 900) is placed along the version provided by the retractor devices. The humeral resection guide 900 is then pinned into place. The humeral head is then osteotomized using the humeral head resection guide.

The anterior labrum and capsule are exposed and released. Now the release is taken down the neck of the humerus and scapula to free up the subscapularis. The shoulder is adducted and forward flexed and humeral head retractor devices (e.g., humeral head retractor device 100) are applied to assist in the exposure of the humeral head osteotomy site. The humeral head exposure can be assisted by a curved retractor that fits along an inferior calcar (e.g., retractor device 700). A retractor device to retract the biceps groove (e.g., retractor device 800) can be placed into the bicipital groove to assist with retraction around the humeral head. The retractor devices described herein can assist with delivering the shoulder to a surgeon so that broaching and reaming can be performed. In some embodiments, a retractor device that provides a sling for the humeral shaft and provides posterior retraction can improve exposure (e.g., humerus lift device 200).

The glenoid may be reamed as necessary. For example, the glenoid may be reamed utilizing an anterior glenoid retractor device (e.g., retractor device 600) that allows for exposure of the glenoid. The teeth of the retractor device 600 and the offset between the teeth can allow for improved glenoid exposure by fitting to the end of the glenoid. A 90 degree reamer and drill are utilized to improve the ability to ream and place glenoid components. Trial implants are placed. Closure is performed. Alternatively, a standard anterior approach is performed to the humeral head.

B. Humeral Head Implant System

Referring now to FIGS. 23-27C, a humeral head implant system 1100 is shown according to an embodiment. In some embodiments, the humeral head implant system 1100 is configured to be used during total shoulder arthroplasty procedures. For example, the humeral head implant system 1100 may be used to avoid damage to the rotator cuff by facilitating a posterior approach. For example, in such an approach, a split of the middle and posterior heads of the deltoid and internervous plane between the teres minor and infraspinatus may be used, improving on existing procedures by avoiding subscapularis dysfunction or rupture, improving access to the retroverted glenoid, and enabling posterior soft tissue balancing to be performed. In addition, visualization of the humerus and glenoid may be improved over rotator interval and subscapularis-splitting approaches, such as when inserting a base component (e.g., a baseplate) of the humeral head implant system 1100, or when attaching a head component to the base component.

The humeral head implant system 1100 includes a head component 1120, an insert component 1140, and a base component 1160. The head component 1120 is configured to engage, attach, or otherwise be coupled to the insert component 1140, such as by a Morse taper engagement. The insert component 1140 includes an engagement surface configured to slide into a corresponding slot of the base component 1160. In some embodiments, the humeral head implant system 1100 improves over existing solutions by allowing a surgeon or other operator installing or implanting the system 1100 to secure the base component 1160 at an implant site, then slide the insert component 1140 and head component 1120 (e.g., when the insert component 1140 and head component 1120 have been coupled or engaged) into the slot, providing a more accessible manner of implanting the head component 1120. For example, as compared to existing systems, in some embodiments the humeral head implant system 1100 can enable precise and varied arrangements of the head component 1120, insert component 1140, and base component 1160, even in restrictive conditions where the anatomy of the patient may limit the spacing available for installing the humeral head implant system 1100.

Figure 24A:
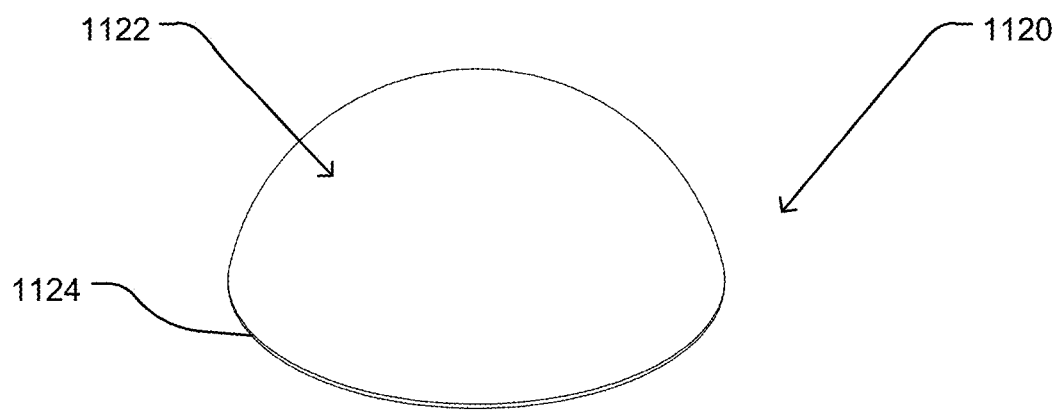
FIG. 24A is a perspective view of an embodiment of a head component of a humeral head implant system.
Figure 24B:
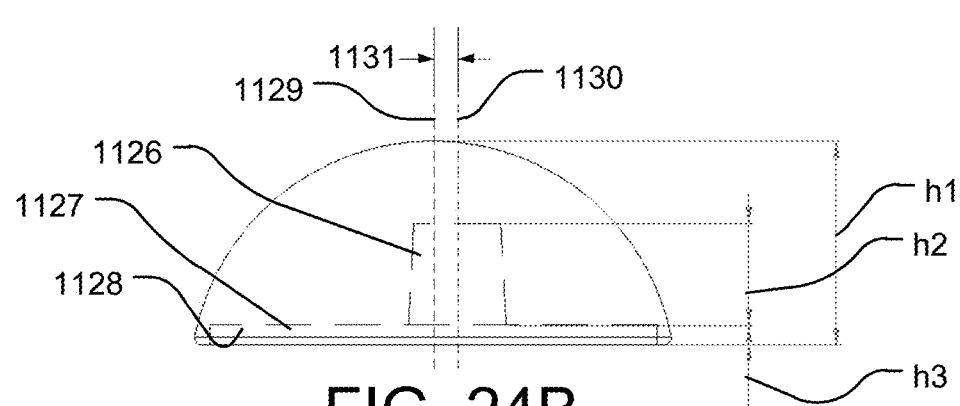
FIG. 24B is a sectional view of the head component of FIG. 24A.
Figure 24C:
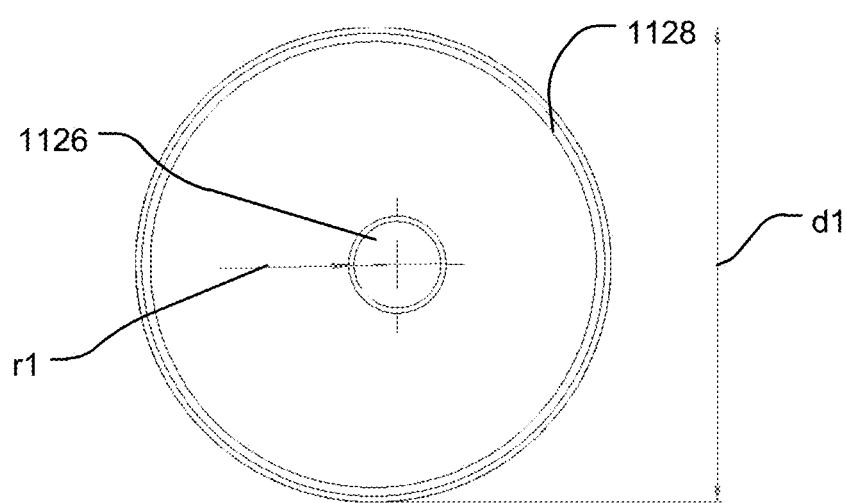
FIG. 24C is a bottom view of the head component of FIG. 24A.
Figure 25A:
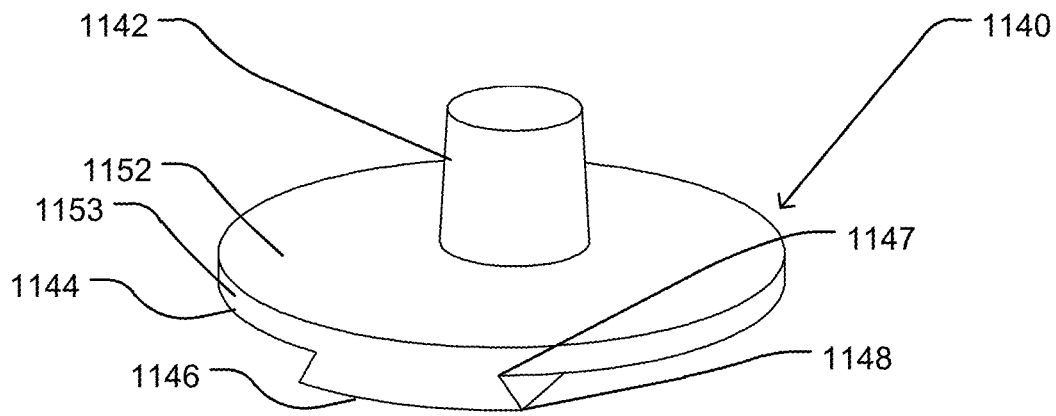
FIG. 25A is a top perspective view of an embodiment of an insert component of a humeral head implant system.
Figure 25B:
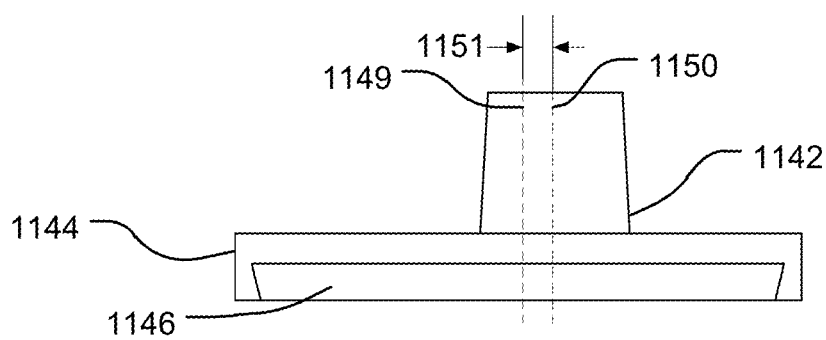
FIG. 25B is a side view of the insert component of FIG. 25A.
Figure 25C:
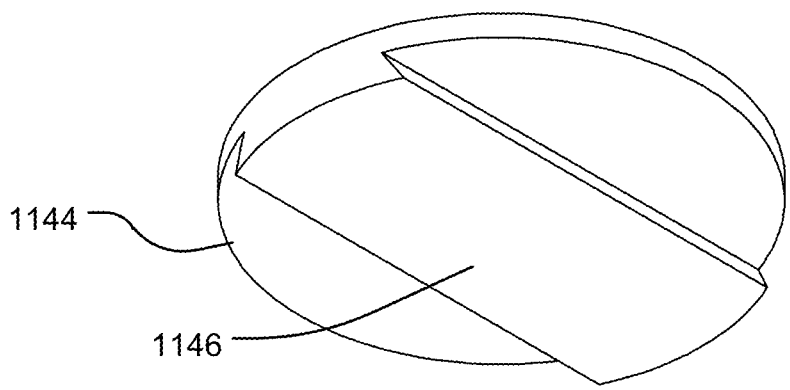
FIG. 25C is a bottom perspective view of the insert component of FIG. 25A.
Figure 25D:
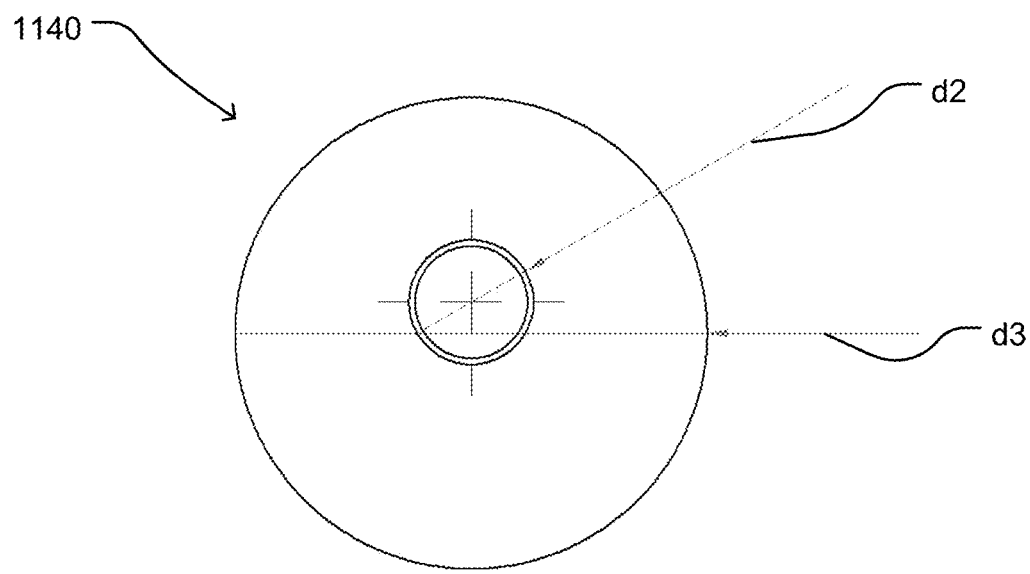
FIG. 25D is a top view of the insert component of FIG. 25A.
Figure 25E:
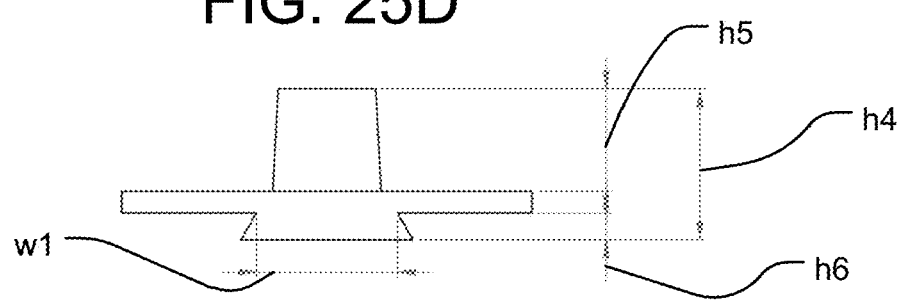
FIG. 25E is another side view of the insert component of FIG. 25A.
Figure 25F:
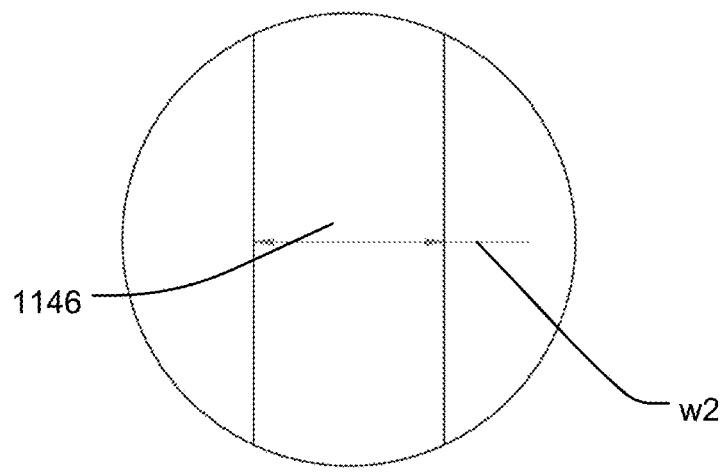
FIG. 25F is a bottom view of the insert component of FIG. 25A.
Figure 26A:
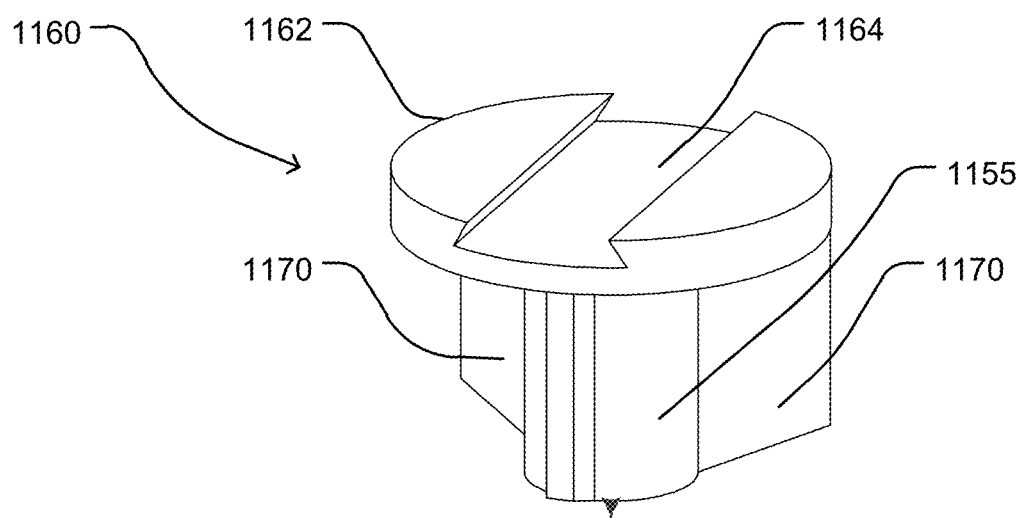
FIG. 26A is a top perspective view of an embodiment of a base component of a humeral head implant system.
Figure 26B:
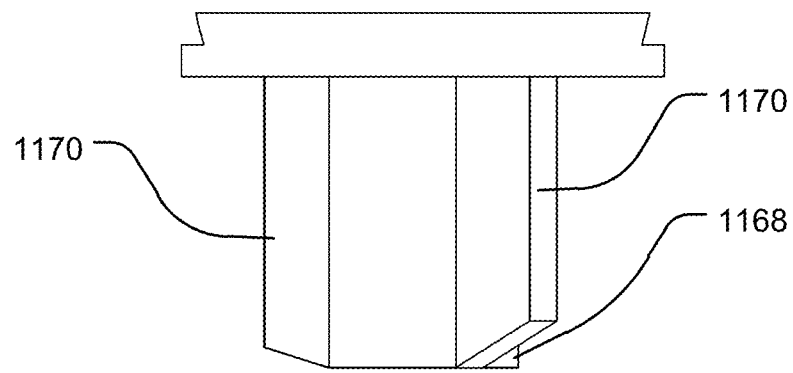
FIG. 26B is a side view of the base component of FIG. 26A.
Figure 26C:
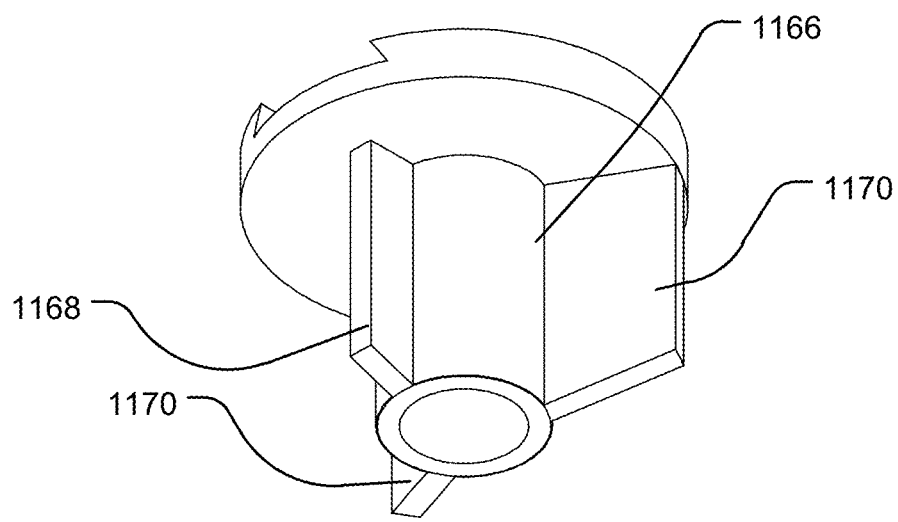
FIG. 26C is a bottom perspective view of the base component of FIG. 26A.
Figure 26D:
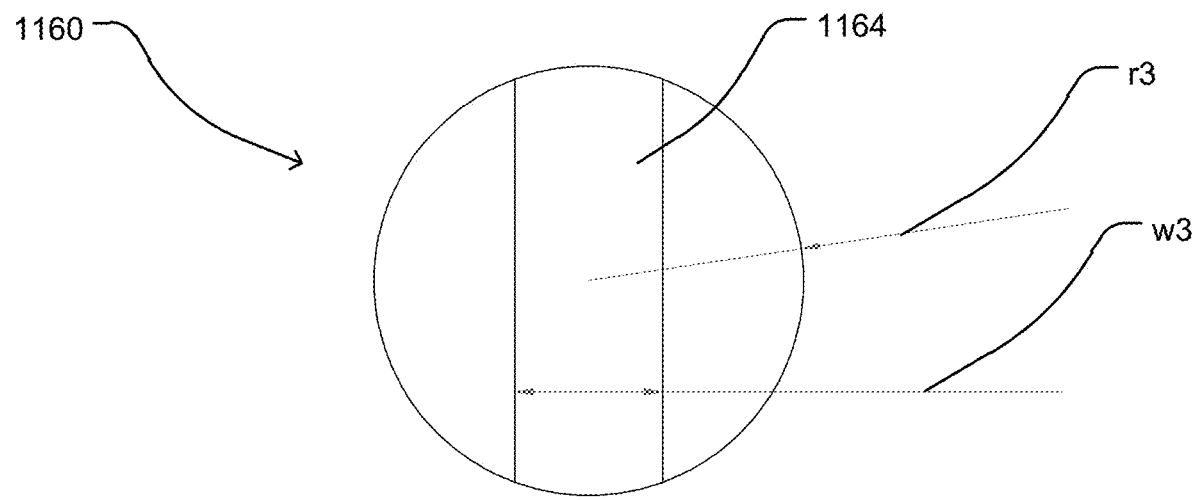
FIG. 26D is a top view of the base component of FIG. 26A.
Figure 26E:
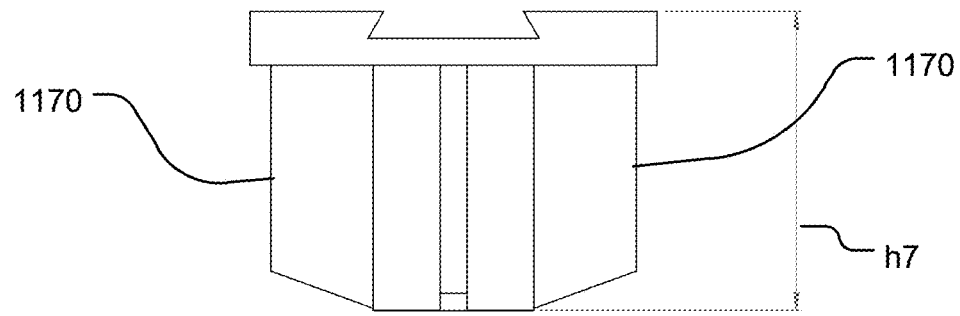
FIG. 26E is another side view of the base component of FIG. 26A.
Figure 26F:
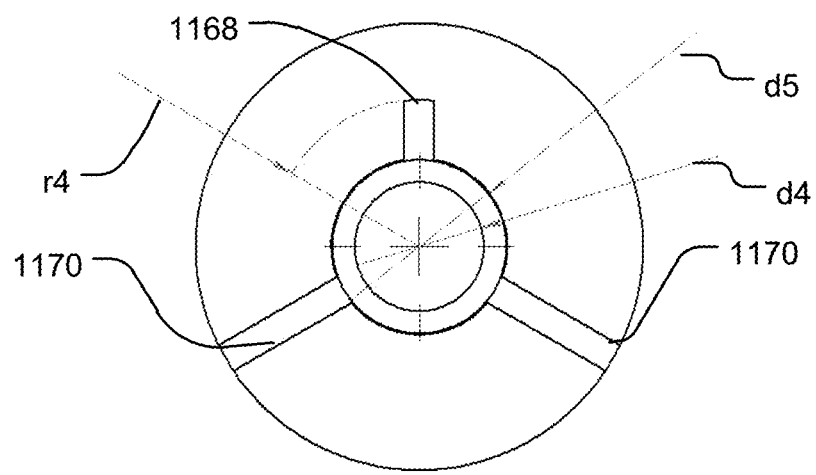
FIG. 26F is a bottom view of the base component of FIG. 26A.

Referring further to FIGS. 24A-24C, an embodiment of the head component 1120 is illustrated. The head component 1120 includes a surface 1122 (e.g., an articulating surface) and an outer rim 1124. The surface 1112 can have a domed, spherical, ellipsoidal, or otherwise rounded shape, allowing for a remote component to articulate along the surface 1122. As described further herein, dimensions of the head component 1120, including height h1 and diameter d1, can define a shape of the surface 1122. The height h1 and/or diameter d1 can be selected to facilitate matching the surface 1122 to an anatomical feature selected to articulate about the surface 1122 and/or to fit the head component 1120 to an implant site. A ratio of the height h1 to the diameter d1 can be varied based on an expected geometry of the implant site. In some embodiments, increasing the height h1 relative to the diameter d1 may increase a range of motion enabled by the head component 1120, but may also increase a profile or form factor of the head component 1120 (e.g., make the head component 1120 less of a low profile device).

The head component 1120 can include a first cavity 1126 (e.g., hole, opening) configured to receive an engagement feature of the insert component 1140, such as by a Morse taper engagement. The first cavity 1126 can taper (e.g., decrease in radius) from a first end at which the engagement feature of the insert component 1140 can be received to a second end. The first cavity 1126 can have a first diameter at the first end which is within a threshold of a maximum diameter of an engagement feature 1142 of the insert component 1140. The first cavity 1126 can have a height h2 which is within a threshold of a height h5 of the engagement feature 1142.

The head component 1120 can also include a second cavity 1127 defined by a receiving wall 1128, which can allow a body of the insert component 1140 to be received inside the head component 1120, such as to allow the head component 1120 to sit flush against the base component 1160. For example, a height h3 of the receiving wall 1128 can be equal to or within a tolerance threshold of a height h5 of an insert body 1144 of the insert component 1140, such that when the insert body 1144 is received in the second cavity 1127, a substantial or entire volume of the insert body 1144 fits within the second cavity 1127. As such, the head component 1120 can be coupled to the base component 1160 via the insert component 1140 without increasing an effective profile of the humeral head implant system 1100 due to a volume of the insert component 1140.

The head component 1120 can define a head axis 1129. The head axis 1129 can be a central axis of the head component 1120. For example, a point along the head axis 1129 on the surface 1122 can be equidistant from many, most, or all points of the outer rim 1124. A point along the head axis 1129 in a plane including the outer rim 1124 can also be equidistant from many, most, or all points of the outer rim 1124. The head axis 1129 can be perpendicular to the plane including the outer rim 1124. The head axis 1129 can pass through a center of the head component 1120, the center defined as a point equidistant from many, most, or all points on the surface 1122. The head axis 1129 can pass through a center of the head component 1120 (e.g., a center of a spherical volume defined by the articulating surface 1122).

The cavity 1126 can define a cavity axis 1130. The cavity axis 1130 can be a central axis of the cavity 1126. The cavity axis 1130 can be equidistant from many, most, or all points along the surface of the cavity 1126. The cavity axis 1130 can be parallel to the head axis 1129. The cavity axis 1130 can be perpendicular to the plane containing the outer rim 1124.

In some embodiments, the head component 1120 is configured to be eccentric. As shown in FIG. 24B, the cavity axis 1130 can be offset from the head axis 1129 by an offset 1131. As the head component 1120 is rotated about the insert component 1140, a greater or lesser volume of the head component 1120 can sit above the base component 1160. For example, the offset 1131 may define a greater volume of the head component 1120 on a first portion of the head component 1120 through which the head axis 1129 passes, and a lesser volume of the head component 1120 on a second portion of the head component 1120 through which the head axis 1129 does not pass. As the head component 1120 is rotated about the insert component 1140 (e.g., while coupled to the insert component 1140 when the engagement feature 1142 is received in the cavity 1126), a location of the greater volume may change relative to the insert component 1140 (and similarly, a location of the lesser volume). As will be described further herein with reference to the base component 1160, the eccentricity of the head component 1120 (e.g., configuring the head component 1120 to include the offset 1131) can allow an offset between an axis of the base component 1160 and the head axis 1129 of the head component 1120 to be varied. In some embodiments, the humeral head implant system 1100 is configured such that an axial offset between the head component 1120 and the base component 1160 can be varied.

The head component 1120 can be sized to fit into an implant site targeted for total shoulder arthroplasty. The head component 1120 can have a height h1 of approximately 21 mm (e.g., 21 mm; greater than or equal to 10 mm and less than or equal to 30 mm). The cavity 1126 can have a height h2 of approximately 10.5 mm (e.g., 10.5 mm; greater than or equal to 5 mm and less than or equal to 21 mm). The receiving wall 1128 can have a height of approximately 2 mm (e.g., 2 mm; greater than or equal to 1 mm and less than or equal to 4 mm). The cavity 1126 (e.g., a rim of the cavity 1126 defining an opening into the cavity 1126) can have a radius r1 of approximately 10.05 mm (e.g., 10.05 mm; greater than or equal to 5 mm and less than or equal to 20 mm). The head component 120 can have a diameter d1 (e.g., a diameter defined by the outer rim 1124) of approximately 49.11 mm (e.g., 49.11 mm; greater than or equal to 24 mm and less than or equal to 100 mm).

Referring further to FIGS. 25A-25F, an embodiment of the insert component 1140 is illustrated. The insert component 1140 includes an engagement feature 1142, an insert body 1144, and a slot engagement feature 1146. In some embodiments, the insert component 1140 may be integrally formed with the head component 120. In some embodiments, the insert component 1140 may be removably coupled to the head component 120. In some embodiments, insert component 1140 may be permanently coupled with the head component 120. In some embodiments, the insert component 1140 may slidably coupled with the head component 120.

The engagement feature 1142 is configured to engage the cavity 1126 (e.g., by a Morse taper engagement). The engagement feature 1142 can be sized to fit within the cavity 1126. For example, a diameter d2 of the engagement feature 1142 can be less than or equal to a maximum diameter of the cavity 1126. The diameter d2 may also be greater than or equal to a minimum diameter of the cavity 1126. The engagement feature 1142 can have a surface curvature matching a surface curvature of the engagement feature 1142. In some embodiments, the engagement feature 1142 is configured to be selectively rotated within the cavity 1126. For example, the engagement feature 1142 can be shaped, sized, and/or include surface engagement features to enable rotation of the engagement feature 1142 relative to the cavity 1126 to adjust a relative orientation of the head component 1120 and the insert component 1140, yet restrict rotation of the head component 1120 relative to the insert component 1140 when the humeral head implant system 1100 is implanted. Alternatively, the engagement feature 1142 can be shaped, sized, and/or include surface engagement features to restrict rotation of the head component 1120 relative to the insert component 1140 unless the head component 1120 and insert component 1140 are not coupled. The engagement feature 1142 and/or cavity 1126 can include relatively high friction surfaces configured to restrict rotation of the insert component 1140 relative to the cavity 1126 unless a rotational force applied to the insert component 1140 or head component 1120 is greater than a threshold force. The threshold force may be greater than an expected force during implantation or operation of the humeral head implant system 1100.

The slot engagement feature 1146 is configured to engage a slot of the base component 1160 (e.g., slide into the slot). The insert component 1140 can advantageously allow a user to slide the insert component 1140 and head component 1120 together into the base component 1160 using less physical space in and around the implant site than existing systems. The slot engagement feature 1146 can provide tactile feedback as the insert component 1140 is slid into the base component 1160, even if the insert component 1140 is coupled to the head component 1120 such that the slot engagement feature 1146 may be partially or completely obscured from a line of sight of a user by the head component 1120.

In some embodiments, the slot engagement feature 1146 has a dovetail shape to facilitate a secure engagement to the base component 1160. For example, a first end of the slot engagement feature 1146 at which the slot engagement feature 1146 extends from the insert body 1144 can have a first width that is less than a second with at a second end of the slot engagement feature 1146 opposite the first end. In some embodiments, the slot engagement feature 1146 restricts a separation from the base component 1160 responsive to a force applied to the slot engagement feature 1146 in a direction other than along a longitudinal axis of the slot engagement feature 1146 (by which the slot engagement feature 1146 may be received by the base component 1160). It should be appreciated that other slot engagement feature may have another shape or design to facilitate a slidable engagement to the base component.

The insert component 1140 can define an insert axis 1149. The insert axis 1149 can pass through a center of the insert component 1140 and/or the insert body 1142, such as a centroid or center of mass. The insert axis 1149 can be perpendicular to a surface 1152 of the insert body 1142. The insert axis 1149 can be equidistant from many, most, or all points on a rim surface 1153 of the insert body 1142.

The engagement feature 1142 can define an engagement axis 1150. The engagement axis 1150 can pass through the engagement feature 1142. The engagement axis 1150 can be equidistant from many, most, or all points on a surface of the engagement feature 1142. The engagement axis 1150 can be parallel to the insert axis 1149. The engagement axis 1150 can be perpendicular to a plane including the surface 1152.

In some embodiments, an orientation of the head component 1120 relative to the insert component 1140 and/or the base component 1160 can be altered based on rotation of the head component 1120 about the engagement axis 1150. When the engagement feature 1142 is received in the cavity 1126, the engagement axis 1150 may align with the cavity axis 1130 of the cavity 1126. In a first configuration, the insert axis 1149 may align with the head axis 1129 when the engagement feature 1142 is received in the cavity 1126. In a second configuration or a plurality of second configurations, the insert axis 1149 may be offset from the head axis 1129 when the engagement feature 1142 is received in the cavity 1126. The insert axis 1149 may be parallel to the head axis 1129 while offset. The humeral head implant system 1100 may be adjusted between the first configuration and one or more of the plurality of second configurations based on rotation of the head component 1120 relative to the engagement feature 1142 about the engagement axis 1150.

A magnitude of the offset may be varied based on rotation of the head component 1120 about the engagement axis 1150. For example, the magnitude of the offset may increase from a first, minimum value (e.g., the offset may be zero when the insert axis 1149 is aligned with the head axis 1129 at the first configuration) to a second, maximum value (e.g., the offset may be greatest when the head component 1120 has been rotated 180 degrees about the engagement axis 1150 from the first configuration), and may decrease from the second, maximum value to the first, minimum value (e.g., when the head component 1120 is rotated 180 degrees further to complete a 360 degree rotation about the engagement axis 1150). When the insert component 1140 is coupled to the base component 1160, the rotation of the head component 1120 about the engagement axis 1150 may also cause a change in orientation of the head component 1120 relative to the base component 1160. In some embodiments, enabling the head component 1120 to be changed in orientation relative to the base component 1160 enables anatomic restoration of the humeral head of the patient. Similarly, when implanting the humeral head implant system 1100, there may be a limited selection of locations at which the base component 1160 may be implanted, such that changing the orientation of the head component 1120 allows for anatomic restoration in ways that would not otherwise be possible.

The insert component 1140 can be sized and shaped to couple the head component 1120 to the base component 1160. The engagement feature 1142 can have a shape, including a diameter d2 of approximately 10.05 mm (e.g., 10.05 mm; greater than or equal to 5 mm and less than or equal to 20 mm) to match the diameter d1 and shape of the cavity 126. The insert body 1144 can have a diameter d3 of approximately 38.08 mm (e.g., 38.08 mm; greater than or equal to 20 mm and less than or equal to 80 mm). The insert component 1140 can have a height h4 of approximately 14 mm (e.g., 14 mm; greater than or equal to 7 mm and less than or equal to 28 mm). The engagement feature 1142 can have a height h5 of approximately 9.50 mm (e.g., 9.50 mm; greater than or equal to 4 mm and less than or equal to 20 mm). The slot engagement feature 1146 can have a height h6 of approximately 2.5 mm (e.g., 2.5 mm; greater than or equal to 1 mm and less than or equal to 5 mm). The slot engagement feature 1146 can have a first width w1 (e.g., a width adjacent to the insert body 1144) of approximately 13.11 mm (e.g., 13.11 mm; greater than or equal to 6 mm and less than or equal to 27 mm) and a second width (e.g., a width at an opposite end of the insert body 1144 from the first width w1) of approximately 16 mm (e.g., 16 mm; greater than or equal to 8 mm and less than or equal to 32 mm).

Referring further to FIGS. 4A-4F, an embodiment of the base component 1160 is illustrated. The base component 1160 includes a first surface 1162 and a slot 1164. The first surface 1162 is configured to be positioned adjacent to the insert component 1140 and/or inserted into the cavity defined by the receiving wall 1128.

The slot 1164 may be defined within the first surface 1162 or may extend into a body of the base component 1160 from the first surface 1162. The slot 1164 may be configured, sized, and/or shaped to receive the slot engagement feature 1146 of the insert component 1140. In some embodiments, the slot 1164 includes a dovetail receiving feature configured to receive a dovetail feature of the slot engagement feature 1146. The dovetail receiving feature may enable a secure fit between the base component 1160 and the insert component 1140, such that a force applied to the base component 1160 or the insert component 1140 may not cause the base component 1160 to separate from the insert component 1140 unless a component of the force is parallel to a longitudinal axis of the slot 1164 (e.g., unless the insert component 1140 is slid out of the slot 1164). A first width of the slot 1164 where the slot extends from the first surface 1162 and a second width of the slot 1164, which is greater than the first width, may each be selected or configured to match corresponding widths of the slot engagement feature 1146, which can restrict movement of the insert component 1140 relative to the base component 1160 while the insert component 1140 is engaged with the base component 1160 unless the insert component 1140 is translated along a longitudinal axis of the slot 1164 (e.g., unless the insert component 1140 is slid along the slot 1164).

In some embodiments, the base component 1160 includes an extension 1166, a first leg 1168 (e.g., a leg or stem having a relatively lesser length; a leg extending a radial distance from the extension 1166 less than a radius of the first surface 1162), and a pair of second legs 1170 (e.g., legs or stems having a relatively greater length; legs extending radially from the extension 1166 by a radial distance equal to the radius of the first surface 1162). The second legs 1170 can extend the same distance from the extension 1166. Having a relatively shorter first leg 1168, which can be positioned superiorly, can facilitate insertion of the base component 1160 at the implant site; having relatively longer legs 1170, which can be positioned inferiorly, can allow rotational control and stability, as opposed to a configuration with all equally sized legs which may be difficult to use in a posterior approach. In some embodiments, the base component 1160 is configured such that at least one of the first leg 1168 or second legs 1170 extends at 90 degrees or approximately ninety degrees (e.g., greater than or equal to 75 degrees and less than or equal to 105 degrees; greater than or equal to 85 degrees and less than or equal to 95 degrees) relative to another of the first leg 1168 or second legs 1170, which may increase stability of the base component 1160.

The base component 1160 can be sized, shaped, and/or configured to engage or otherwise be coupled to the insert component 1140 and the head component 1120. The base component 1160 can have a radius r3 of approximately 19.04 mm (e.g., 19.04 mm; greater than or equal to 9 mm and less than or equal to 40 mm). The slot 1164 can have a width w3 of approximately 13.11 mm (e.g., 13.11 mm; greater than or equal to 6 mm and less than or equal to 27 mm). The extension 1166 can have a diameter d4 of approximately 11 mm (e.g., 11 mm; greater than or equal to 5 mm and less than or equal to 22 mm) and a diameter d5 of approximately 14.79 mm (e.g., 14.79 mm; greater than or equal to 7 mm and less than or equal to 30 mm). The leg 1168 can have a radius r4 of approximately 12.5 mm (e.g., 12.5 mm; greater than or equal to 6 mm and less than or equal to 25 mm).

Referring further to FIGS. 27A-27E, various views of the humeral head implant system 1100 are shown according to various configurations, orientations, and embodiments.

Figure 28C:
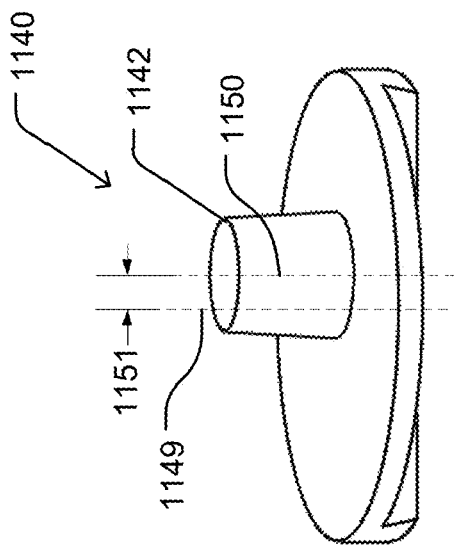
FIGS. 28A-28C illustrate various embodiments of engagement features of an insert of a humeral head implant system.
Figure 28B:
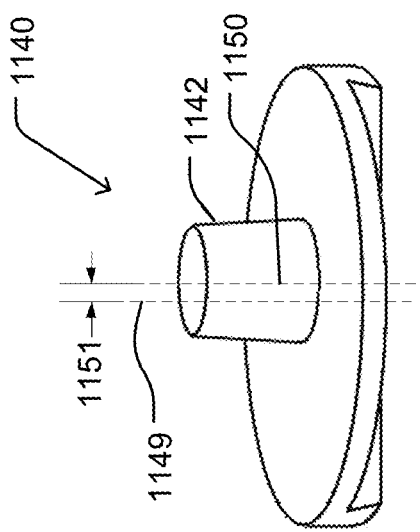
Figure 28A:
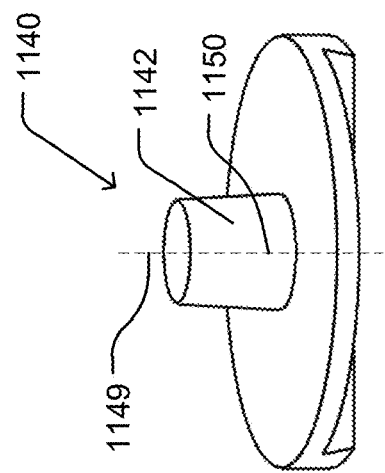
Figure 29:
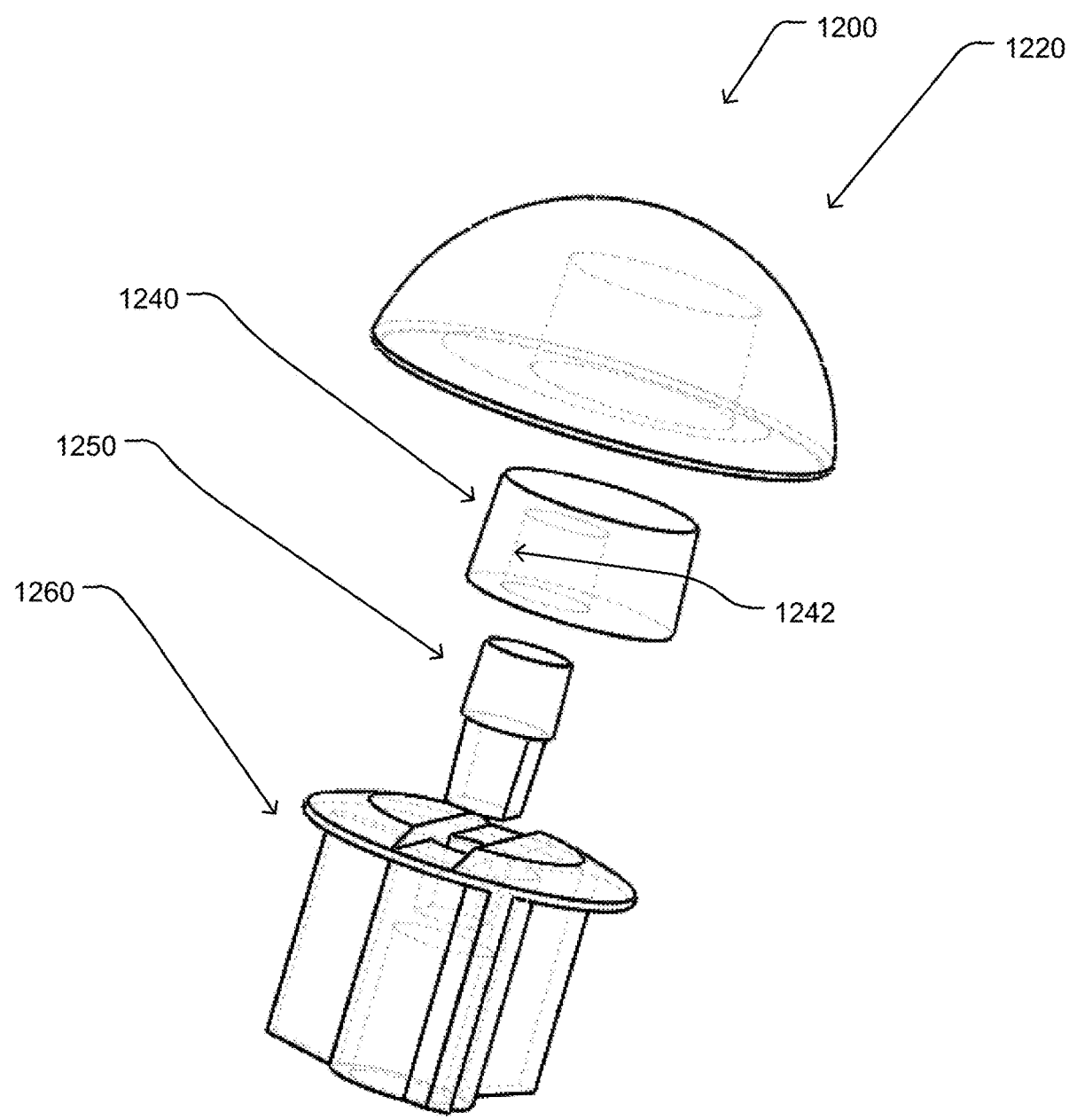
FIG. 29 is an exploded view of another embodiment of a humeral head implant system.

Referring further to FIGS. 28A-28C, various embodiments of the engagement feature 1142 of the insert component 1140 are illustrated. For example, the engagement feature 1142 can be located, positioned, or otherwise included in the insert component 1140 at various radial distances from a center of the insert component 1140, such as to allow for various ranges of motion, orientation, or eccentricity of the head component 1120 relative to the insert component 1140. As shown in FIG. 28A, the insert axis 1149 and engagement axis 1150 may be aligned, such that there is no offset between the insert axis 1149 and engagement axis 1150. As shown in FIGS. 28B-28C, a magnitude of the offset 1151 may be varied as the position of the engagement feature 1142 is varied.

Referring now to FIGS. 29-33E, a humeral head implant system 1200 is shown according to an embodiment. The humeral head implant system 1200 can be similar to the humeral head implant system 1100, and can include further features relating to the engagement between the insert components 1240, 1250 and the head component 1220, and between the insert component 1250 and the base component 1260, as described further herein. The system 1200 can include a head component 1220, a first insert component 1240, a second insert component 1250, and a base component 1260. The first insert component 1240 is configured to engage or otherwise couple to the head component 1220, such as by a Morse taper engagement. The second insert component 1250 is configured to engage or otherwise couple to the first insert component 1240 and to the base component 1260, such as by a Morse taper engagement The first insert component 1240 can include or define a first insert cavity 1242 configured to receive the second insert component 1250. The first insert cavity 1242 can be sized, shaped, and/or configured to match a shape of the second insert component 1250.

Figure 30A:
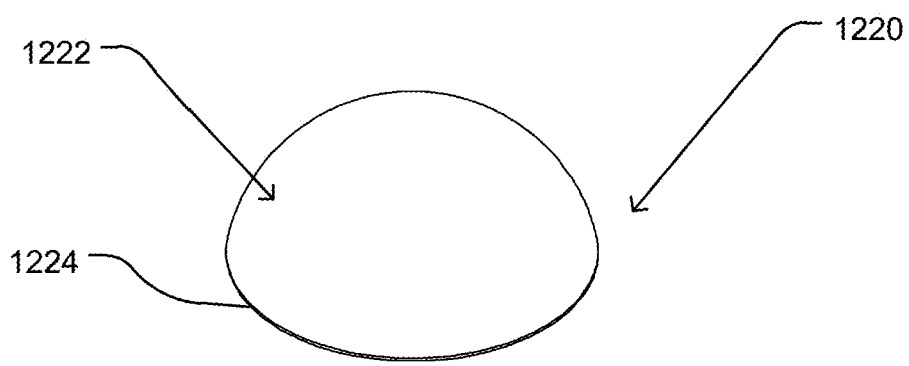
FIG. 30A is a perspective view of an embodiment of a head component of a humeral head implant system.
Figure 30B:
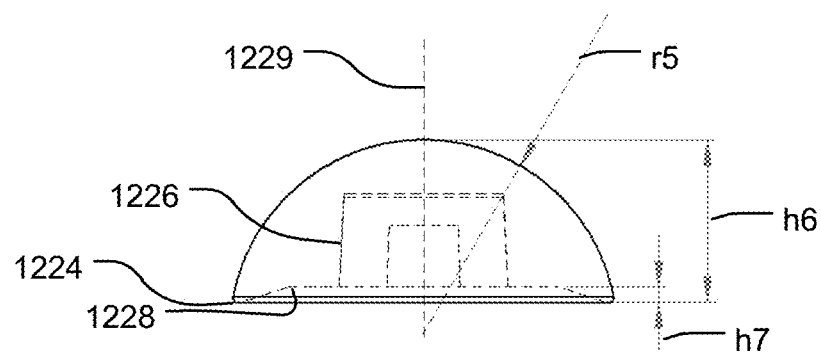
FIG. 30B is a sectional view of the head component of FIG. 30A.
Figure 30C:
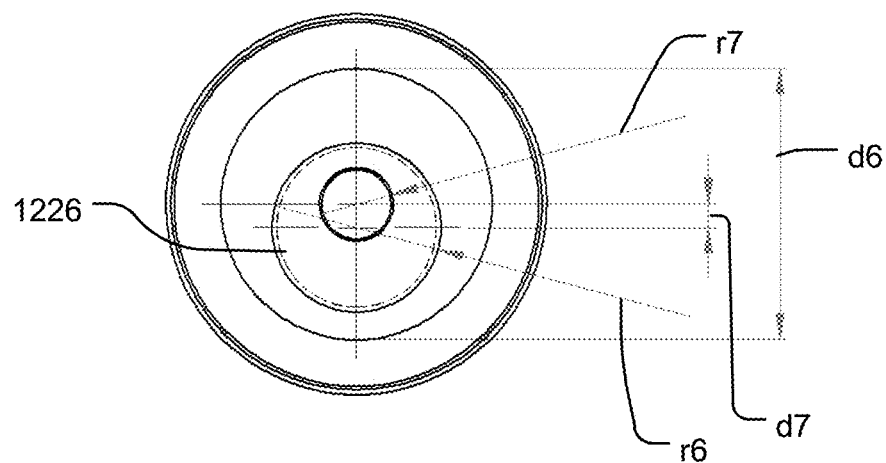
FIG. 30C is a bottom view of the head component of FIG. 30A.
Figure 34:
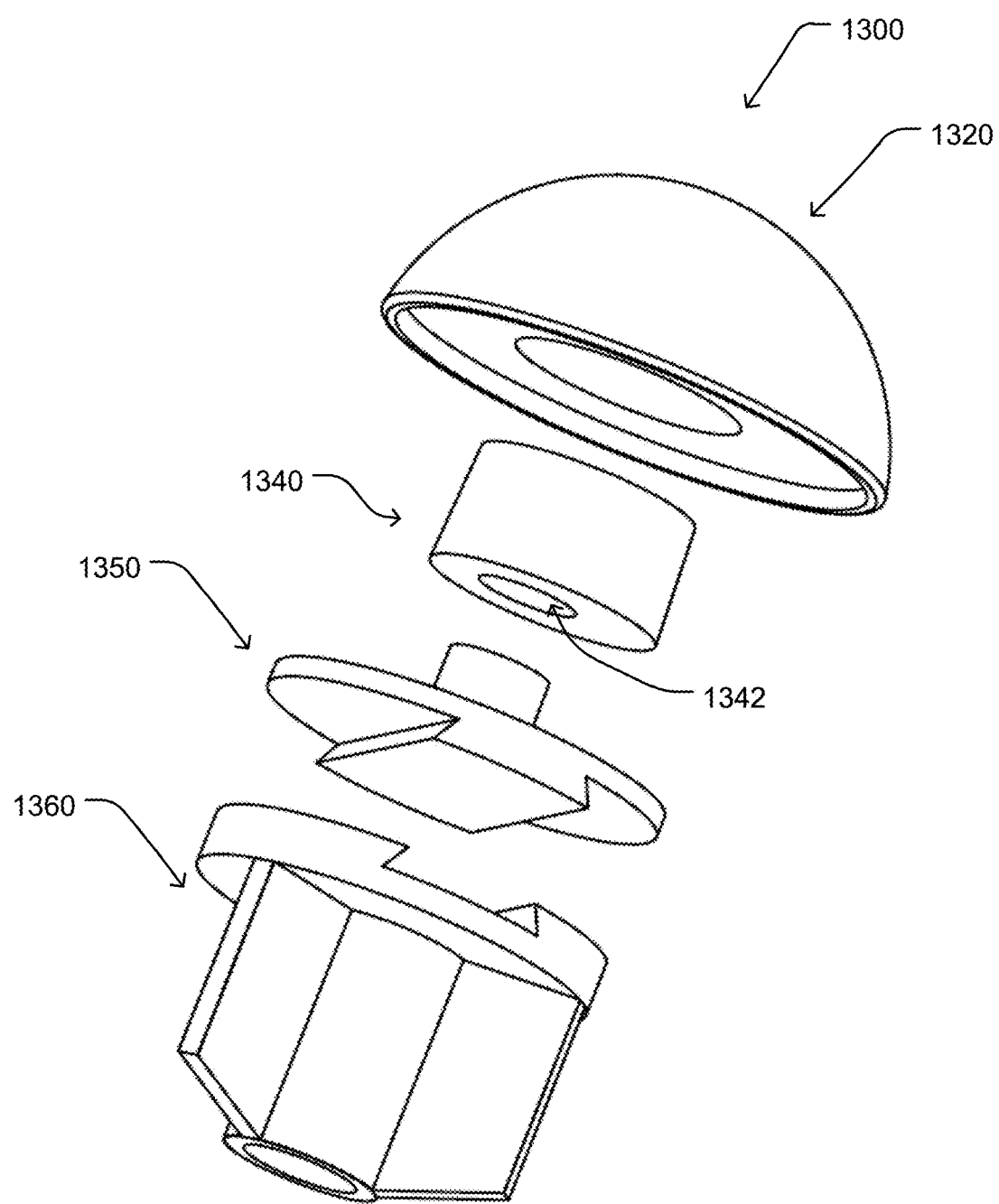
FIG. 34 is an exploded view of another embodiment of a humeral head implant system.

Referring further to FIGS. 8A-8C, the head component 1220 (and/or the first insert component 1240 when received in the head component 1220) includes an articulating surface 1222, an outer rim 1224, a cavity 1226, and a receiving wall 1228. The head component 1220 can be sized, shaped, or otherwise configured for dual eccentricity (e.g., allowing for two radial degrees of motion for selecting a relative orientation of the head component 1220 to the base component 1260) and for engaging the first insert component 1240 and/or the second insert component 1250. Similar to the relationship between the cavity 1126 and the engagement feature 1142, the cavity 1226 can be shaped to match a shape of the insert component 1240, such that the first insert component 1240 can be securely received in the cavity 1226. As shown in FIG. 30C, a center of the cavity 1226 (or a cavity axis of the cavity 1226) may be offset from a center of the head component 1220 (or the head axis 1229) by an offset distance d7.

The head component 1220 can define a head axis 1229. The head axis 1229 can be defined in a similar manner to the head axis 1129 of the head component 1120. For example, the head axis 1229 can be perpendicular to a plane including the outer rim 1224 and equidistant from many, most, or all points of the outer rim 1224. The head axis 1229 can pass through a center of the surface 1222.

The head component 1220 can have a radius r5 of approximately 25 mm (e.g., 25 mm; greater than or equal to 12 mm and less than or equal to 50 mm). The head component 1220 can have a height h6 of approximately 21 mm (e.g., 21 mm; greater than or equal to 10 mm and less than or equal to 42 mm). The head component 1220 can have a height h7 of approximately 2 mm (e.g., 2 mm; greater than or equal to 1 mm and less than or equal to 4 mm). The head component 1220 can have a diameter d6 of approximately 35 mm (e.g., 35 mm; greater than or equal to 17 mm and less than or equal to 70 mm). The offset distance d7 may be approximately 3 mm (e.g., 3 mm; greater than or equal to 1 mm and less than or equal to 6 mm). The head component 1220 can have a radius r6 of approximately 21.80 mm (e.g., 21.80 mm; greater than or equal to 10 mm and less than or equal to 42 mm). The head component 1220 can have a radius r7 of approximately 9.5 mm (e.g., 9.5 mm; greater than or equal to 4 mm and less than or equal to 19 mm).

Referring further to FIGS. 31A-31E, the second insert component 1250 includes a first region 1252 and a second region 1254. The first region 1252 can be sized, shaped, and/or configured to be received in and/or engage the first insert component 1240 (e.g., a cavity thereof). The second region 1254 can be sized, shaped, and/or configured to be received in and/or engage the base component 1260 (e.g., a slot or cavity thereof). The second region 1254 includes a first surface 1256 configured, sized, and/or shaped to slide along the slot of the base component 1260. The second region 1254 includes a second surface 1258 configured to fit or engage (e.g., by a Morse taper) a cavity of the slot of the base component.

The second insert component 1250 can have a radius r8 of approximately 4.75 mm (e.g., 4.75 mm; greater than or equal to 2 mm and less than or equal to 10 mm). The second insert component 1250 can have a height h8 of approximately 17 mm (e.g., 17 mm; greater than or equal to 8 mm and less than or equal to 34 mm). The second insert component 1250 can have a height h9 of approximately 8 mm (e.g., 8 mm; greater than or equal to 4 mm and less than or equal to 16 mm). The first surface 1256 of the second region 1254 can have a width w6 of approximately 7 mm (e.g., 7 mm; greater than or equal to 3.5 mm and less than or equal to 14 mm).

Referring further to FIGS. 32A-32F, the base component 1260 can include base surface 1262, a slot 1264, and a slot cavity 1265 configured to receive the second insert component 1250. The base component 1260 can also include an extension 1266, a first leg 1268, and a pair of second legs 1270.

The slot 1264 can have a ramp feature, a base surface, and/or side walls sized, shaped, or otherwise configured to receive and engage the second insert component 1250. For example, the second insert component 1250 can be aligned with the edges of the slot 1264 such that the walls of the first surface 1256 fit against the side walls of the slot 1264, such that a user can slide the second insert component 1250 (e.g., with the first insert component 1240 and the head component 1220 coupled to the second insert component 1250) along the slot 1264 into the slot cavity 1265.

The base component 1260 can have a height h10 of approximately 27.98 mm (e.g., 27.98 mm; greater than or equal to 13 mm and less than or equal to 56 mm). The base component 1260 can have a height h11 of approximately 2 mm (e.g., 2 mm; greater than or equal to 1 mm and less than or equal to 4 mm). The base component 1260 can have a radius r9 of approximately 17.50 mm (e.g., 17.50 mm; greater than or equal to 8 mm and less than or equal to 35 mm). The base component 1260 can have a height r10 of approximately 11.50 mm (e.g., 5 mm; greater than or equal to 11.50 mm and less than or equal to 23 mm). The base component 1260 can have a width w7 of approximately 7 mm (e.g., 7 mm; greater than or equal to 3.5 mm and less than or equal to 14 mm). The base component 1260 can have a diameter d11 of approximately 11 mm (e.g., 11 mm; greater than or equal to 5 mm and less than or equal to 22 mm). The base component 1260 can have a diameter d12 of approximately 14.79 mm (e.g., 14.79 mm; greater than or equal to 7 mm and less than or equal to 29 mm). The base component 1260 can define a base axis 1272. The base axis 1272 can be perpendicular to the slot 1264. The base axis 1272 can pass through or include a center of the base component 1260. The base axis 1272 can be equidistant from many, most, or all points of the base surface 1262 or a rim of the base surface 1262, and can be perpendicular to a plane including the base surface 1262 or a rim of the base surface 1262.

In some embodiments, the humeral head implant system 1200 is configured such that the head axis 1229 can be offset from the base axis 1272 based on rotation or orientation of the head axis 1229 about an engagement axis of at least one of the first insert component 1240 or the second insert component 1250. For example, a configuration of the head component 1220 relative to the base component 1260 can be varied based on a rotation or orientation of at least one of (1) the head component 1220 relative to the first insert component 1240; (2) the first insert component 1240 relative to the second insert component 1250; or (3) the second insert component 1250 relative to the base component 1260. In some such embodiments, the humeral head implant system 1200 may enable more precise configuration of the head component 1220 relative to the base component 1260 while maintaining a low profile form factor for the humeral head implant system 1200 during and subsequent to implantation. For example, the first insert component 1240 and second insert component 1240 enable at least two degrees of rotational freedom for adjusting how the volume of the head component 1220 can be positioned relative to the base component 1260.

Referring further to FIGS. 33A-33E, various views of the humeral head implant system 1200 are shown according to various configurations, orientations, and embodiments. In some embodiments, such as shown in FIG. 33E, surfaces of the head component 1220 (e.g., surfaces from which the cavity 1226 extends) can be shaped to allow for accurate humeral head sizing when restoring a natural anatomy of a patient and a geometry of the humeral head.

Referring now to FIGS. 34-37E, a humeral head implant system 1300 is shown according to an embodiment. The humeral head implant system 1300 can be similar to the systems 1100, 1200 described herein. For example, the humeral head implant system 1300 includes the base component 1160 of the system 1100. The humeral head implant system 1300 includes a head component 1320, a first insert component 1340, and a second insert component 1350. The second insert component 1350 may be received within a cavity of a head component 1320 of the humeral head implant system 1300 independent of an orientation of the head component 1320 relative to the base component 1160, which can allow for a more secure implantation of the humeral head implant system 1300. For example, the second insert component 1350 can be received such that the head component 1320 sits flush against the base component 1160 independent of an orientation of the head component 1320, such as an angular position of the head component 1320. The first insert component 1340 includes a first insert cavity 1342 configured to receive the second insert component 1350.

Figure 35A:
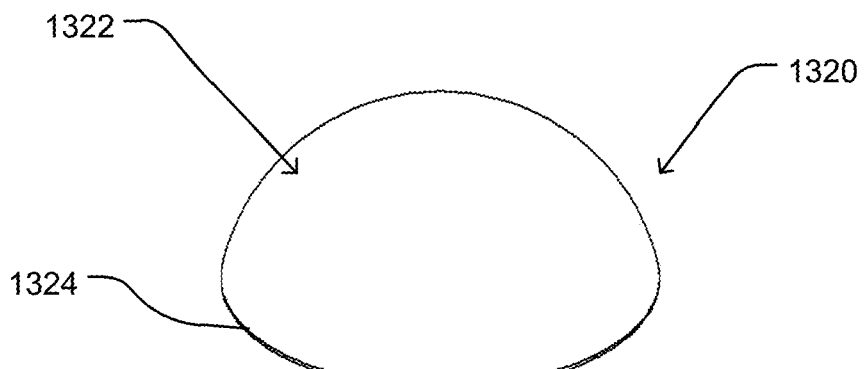
FIG. 35A is a perspective view of an embodiment of a head component of a humeral head implant system.
Figure 35B:
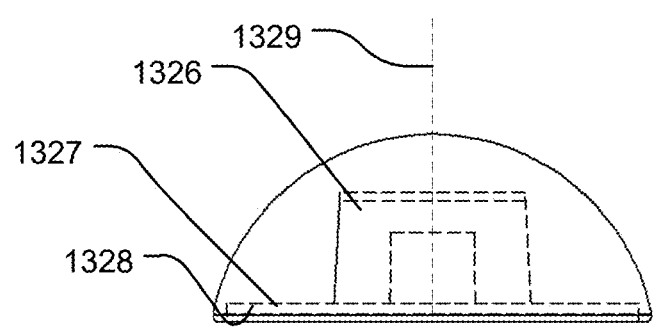
FIG. 35B is a sectional view of the head component of FIG. 35A.
Figure 35C:
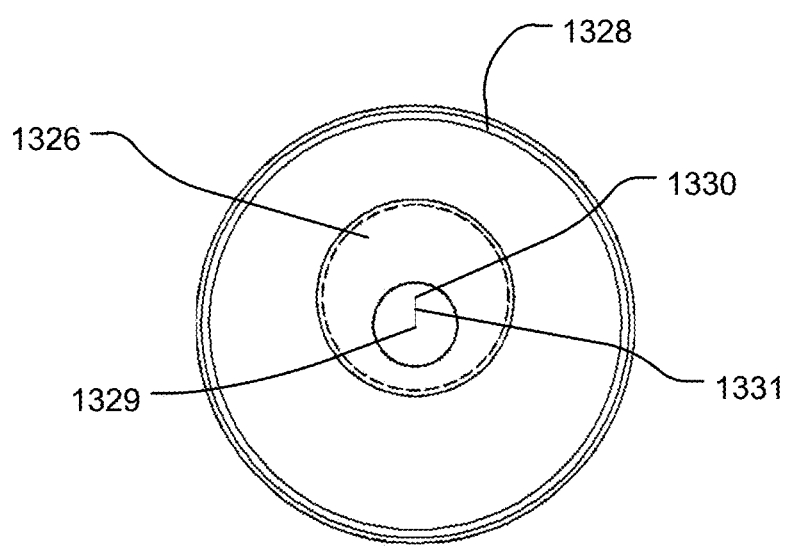
FIG. 35C is a bottom view of the head component of FIG. 35A.
Figure 36A:
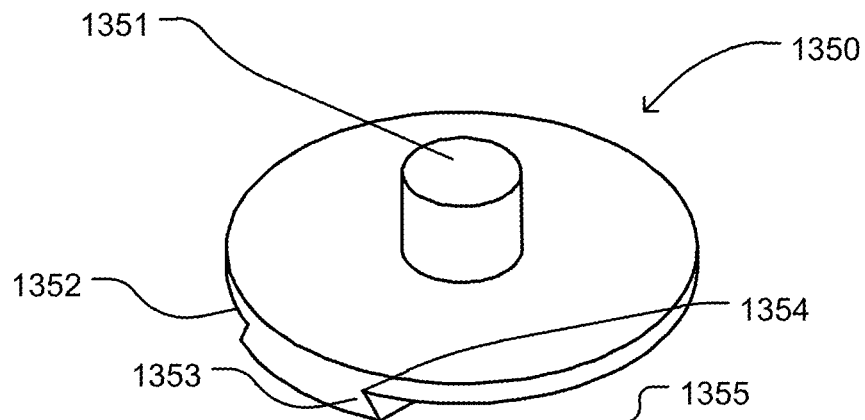
FIG. 36A is a perspective view of an insert component of a humeral head implant system.
Figure 36B:
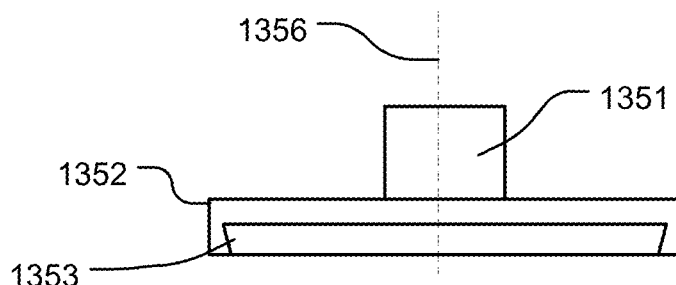
FIG. 36B is a side view of the insert component of FIG. 36A.
Figure 36C:
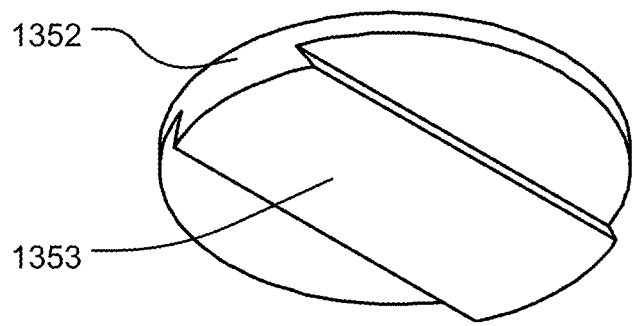
FIG. 36C is a bottom perspective view of the insert component of FIG. 36A.
Figure 36D:
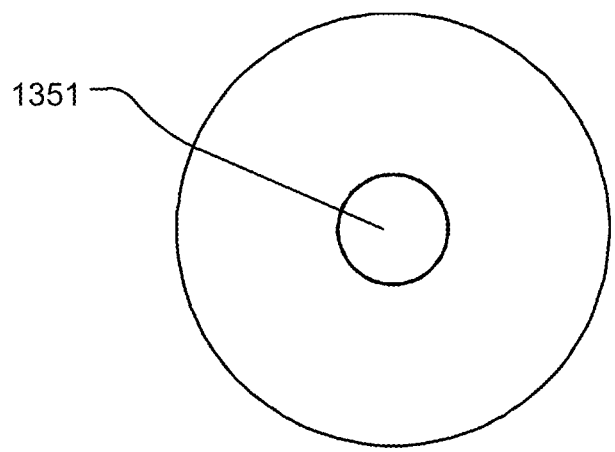
FIG. 36D is a top view of the insert component of FIG. 36A.
Figure 36E:
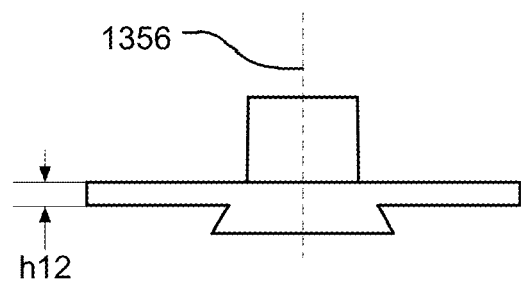
FIG. 36E is another side view of the insert component of FIG. 36A.
Figure 36F:
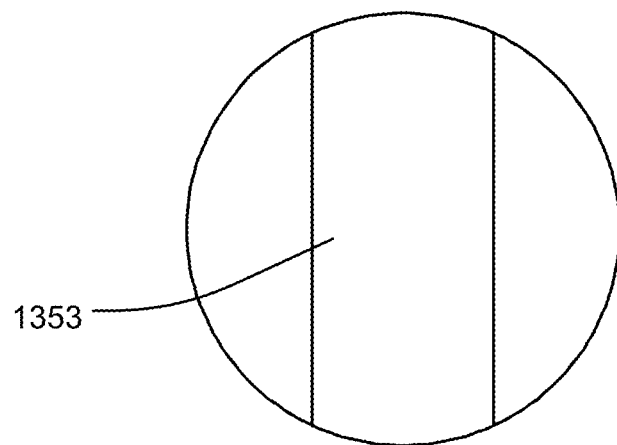
FIG. 36F is a bottom view of the insert component of FIG. 36A.

Referring further to FIGS. 35A-35C, the head component 1320 includes a surface 1322 and an outer rim 1324. The head component 1320 includes or defines a first cavity 1326. The first cavity 1326 is configured to receive the first insert component 1340. The head component 1320 includes or defines a second cavity 1327. The second cavity 1327 can be defined by a receiving wall 1328.

As shown in FIG. 35C, the head component 1320 is configured to be eccentric. The first cavity 1326 can be configured to be offset from the head component 1320. For example, a first cavity axis 1330 of the first cavity 1326 can be offset by a first offset 1331 relative to a head axis 1329 of the head component 1320 (see also FIGS. 37A-37E). The head axis 1329 can be defined to pass through a center of the head component 1320, or a center of a plane defined by the outer rim 1324. The cavity axis can be defined to pass through a center of the cavity 1326, or as an axis equidistant from many, most, or all points on a surface defining the cavity 1326 and perpendicular to a plane including the outer rim 1324.

Referring further to FIGS. 36A-36F, the second insert component 1350 includes an engagement member 1351, an insert body 1352, and a slot engagement feature 1353. The slot engagement feature 1353 extends from a first end 1354 adjacent to the insert body 1352 to a second end 1355. The second insert component 1350 is similar to the insert component 1140, except that the engagement member 1351 is configured to be aligned with a center of the insert body 1352. For example, the engagement member 1351 can define an engagement axis 1356 which passes through a center of the engagement member 1351 (e.g., through a point equidistant from many, most, or all points on a side surface of the engagement member 1351). The engagement axis 1356 can also pass through a center of the insert body 1352 (e.g., through a center of a surface of the insert body 1352).

The insert body 1352 can define a height $h_{12}$. The height $h_{12}$ can be less than or equal to a height of the receiving wall 1328 of the head component 1320, such that the insert body 1352 fits within the second cavity 1327.

Referring further to FIGS. 37A-37E, various views and configurations of the humeral head implant system 1300 are shown according to an embodiment of the present disclosure. The humeral head implant system 1300 is configured such that the head component 1320 (e.g., a surface of the head component 1320 defined by the outer rim 1324) contacts the base component 1160 (e.g., a surface of the base component 1160 from which the slot 1164 extends). The head component 1320 may be seated flush against the base component 1160.

By including the first insert component 1340 and second insert component 1350, the head component 1320 may be seated flush against the base component 1160 independent of an orientation of the head component 1320 relative to the base component 1160. For example, the head component 1320 may be oriented at various angles about the head axis 1329 when the first insert component 1340 is received in the first cavity 1326. The first insert component 1340 may be oriented at various angles when the engagement member 1351 is received in the first insert component 1340. Because the first insert component 1340 enables the head component 1320 to be rotated about the second insert component 1350, the head component 1320 may be flush against the base component 1160 at any angular orientation.

In some embodiments, the humeral head implant system 1300 is configured to offset the head axis 1329 of the head component 1320 from a base axis 1171 of the base component 1160. The offset between the head axis 1329 and the base axis 1171 can be defined as a sum of the first offset 1331 between the head axis 1329 and the cavity axis 1330 and a second offset between a first insert axis 1343 of the first insert 1340 and a first insert cavity axis 1344 of the first insert 1340. When the first insert component 1340 is received in the head component 1320, the first insert axis 1343 may align with the cavity axis 1330. When the second insert component 1350 is received in the first insert cavity 1342 of the first insert component 1340, the engagement axis 1356 may align with the first insert cavity axis 1344 of the first insert cavity 1342. When the second insert component 1350 is received by the base component 1160, the engagement axis 1356 may align with base axis 1171 of the base component 1160.

C. Method of Performing Posterior Rotator Cuff Sparing Total Arthroplasty

Figure 38A:
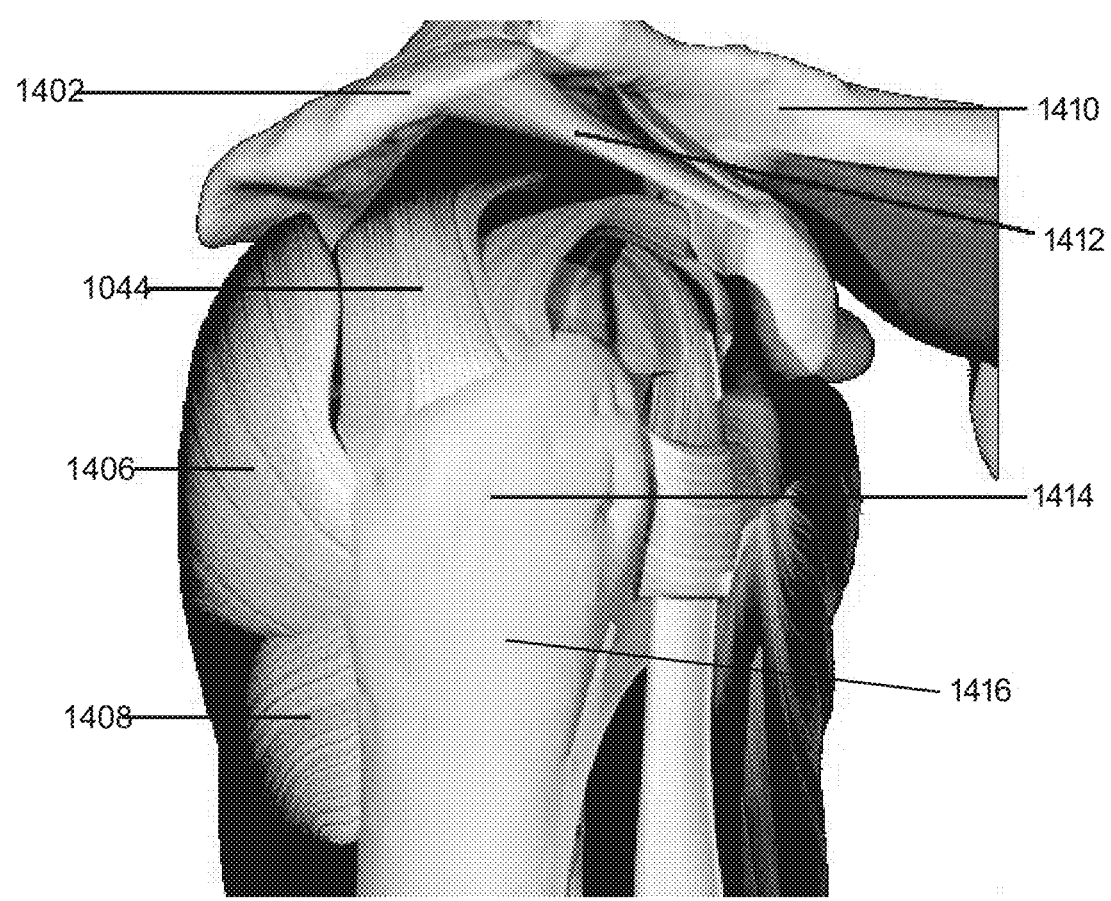
FIG. 38A is a schematic diagram illustrating an end view of an example shoulder anatomy.
Figure 38B:
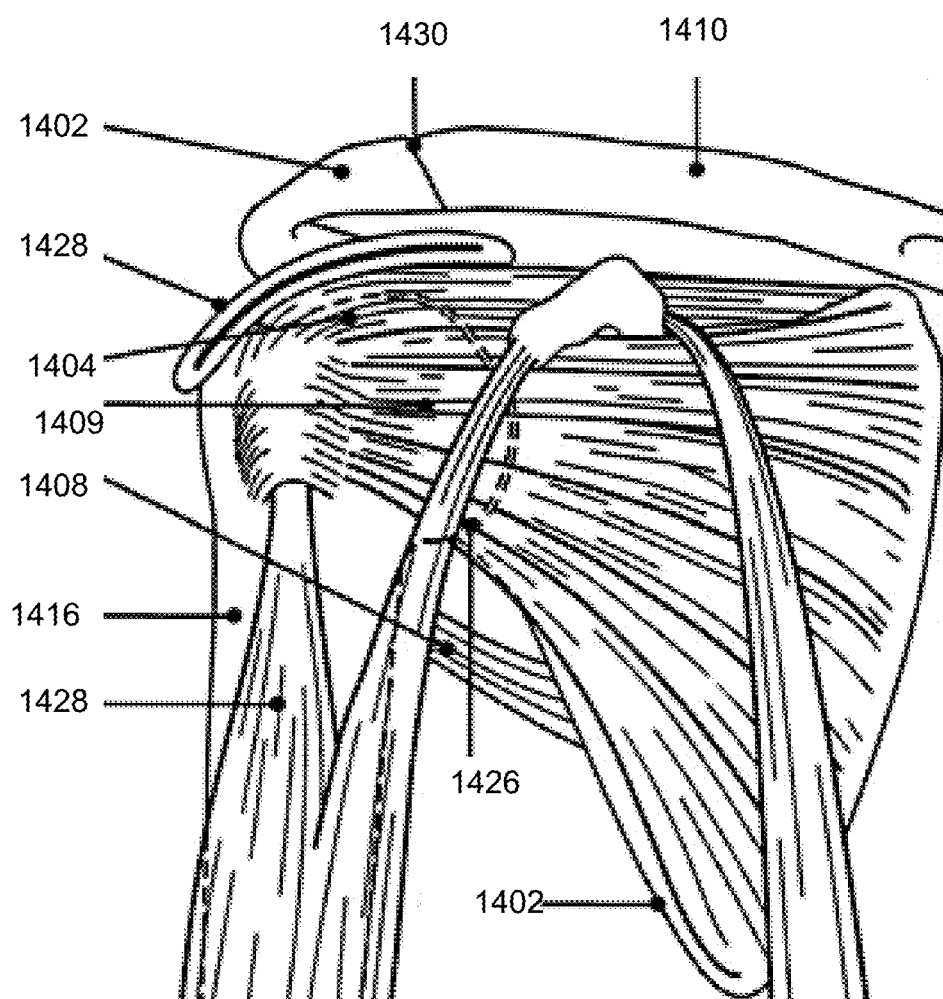
FIG. 38B is a schematic diagram illustrating a side view of an example shoulder anatomy.
Figure 39A:
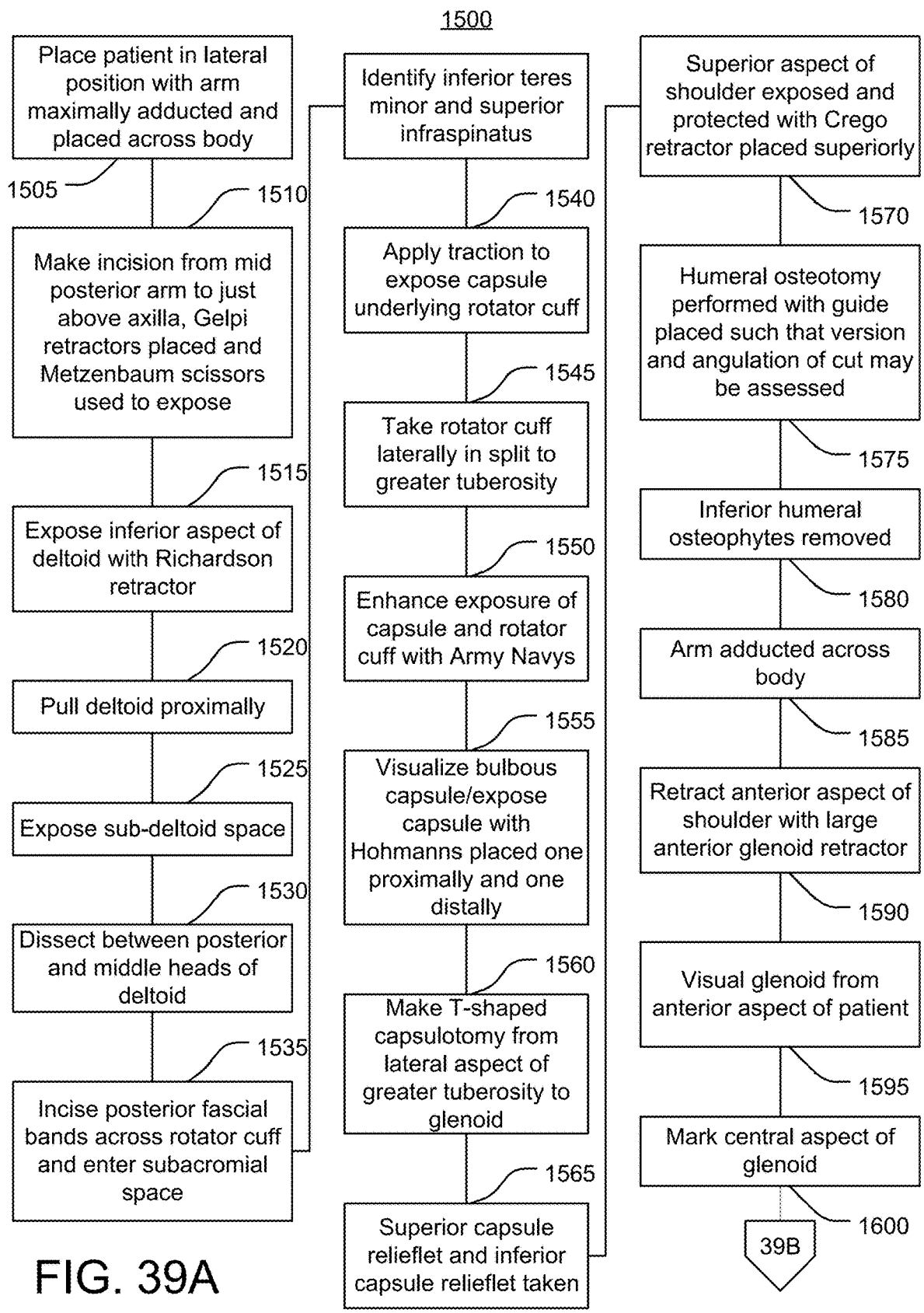
FIGS. 39A-39B are flow diagrams of an embodiment of a method of performing a posterior approach rotator cuff sparing total shoulder arthroplasty.
Figure 39B:
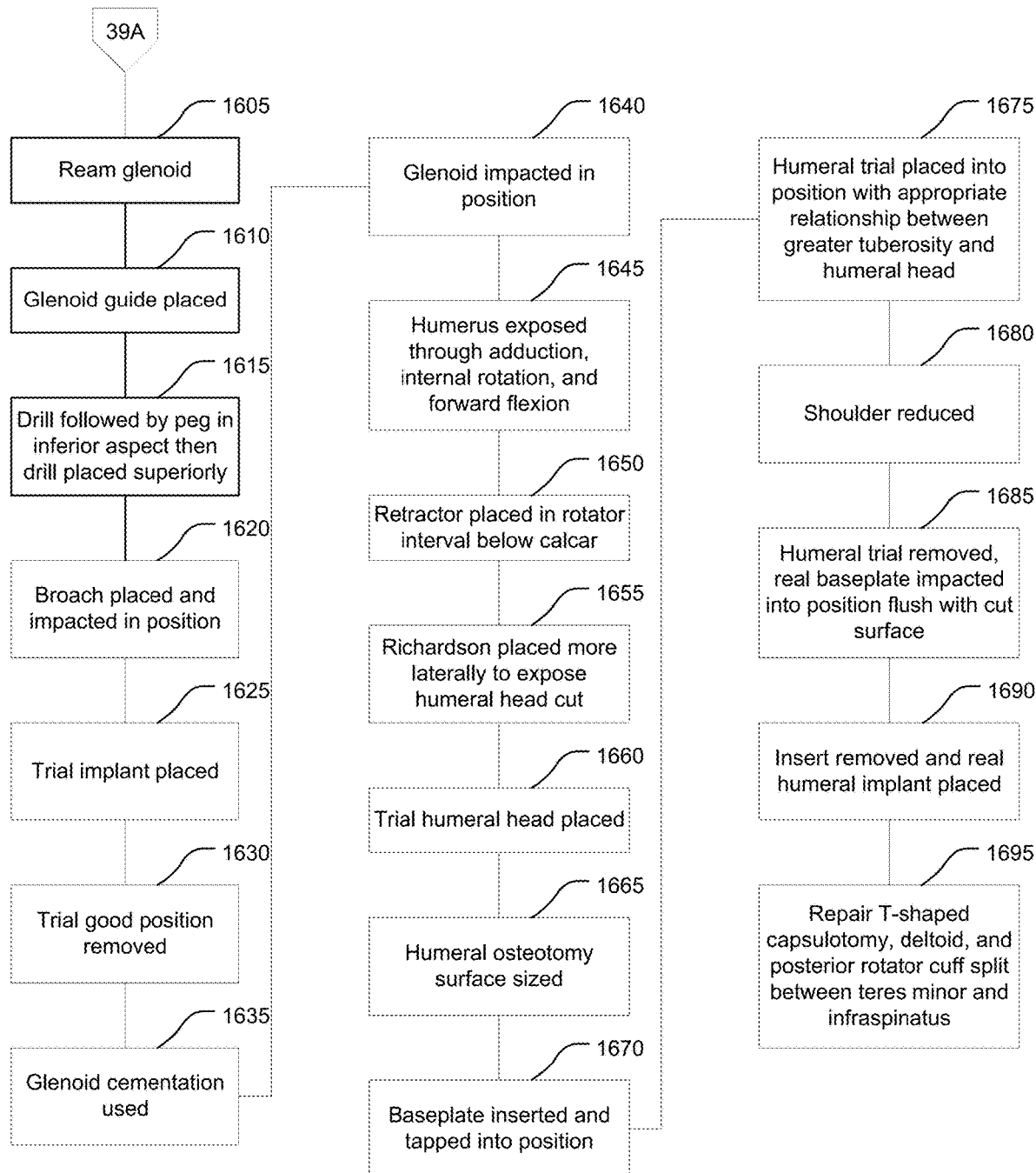

Referring now to FIGS. 38A-38B, schematic diagrams of an example shoulder anatomy are illustrated. The shoulder anatomy includes the rotator cuff, including the supraspinatus 1404 (which can abduct the humerus), infraspinatus 1406 (which can externally rotate the humerus), teres minor 1408 (which can externally rotate the humerus), and subscapularis 1409 (which can internally rotate the humerus). The shoulder anatomy also includes acromion 1402, clavicle 1410, coraco-acromial ligament 1412, and greater tuberosity 1414 of the humerus 1416. The coraco-acromial ligament 1412 defines subacromial space 1414, in which bursa 1418 and supraspinatus 1404 are located. The coraco-acromial ligament 1412 connects to the acromion 1402 and coracoid process 1420 of scapula 1422. Long head of biceps 1428 tendon 1424 also connects the humerus 1416 to scapula 1422. The shoulder anatomy also includes gleno-humeral joint 1426, bursa 1428 between the acromion 1402 and rotator cuff, and acromioclavicular joint 1430.

In existing solutions, shoulder arthroplasty can result in long recovery times due to how the rotator cuff is removed in order to perform the procedure. The present disclosure relates to devices, systems, and methods for improving shoulder arthroplasty while preventing damage to the rotator cuff, such as by using instruments that can position the humerus and glenoid at an accessible orientation for implant installation without cutting the rotator cuff. The traditional total shoulder arthroplasty approach utilizes a subscapularis takedown via tenotomy, peel or lesser tuberosity osteotomy.

Total shoulder arthroplasty (TSA) has long been one of the more successful procedures orthopaedic surgeons perform. Complications including subscapularis rupture, dysfunction and attenuation, infection, superior rotator cuff failure, and glenoid loosening remain issues. Subscapularis dysfunction and failure are the leading complications of TSA, occurring in 11%-66% of patients. Surgical intervention for subscapularis dysfunction is relatively rare, but frequently is unsuccessful. The standard anterior approach to the shoulder requires division of the subscapularis tendon either through a tenotomy, peel, or lesser tuberosity osteotomy. It is accepted that the lesser tuberosity osteotomy and peel techniques are more resistant to subscapularis rupture, but chronic nerve denervation, weakness and tendon dysfunction are still relatively common and long-lasting. Subscapularis insufficiency may result in long term issues with glenoid loosening due to increased forces on the cement-prosthesis interface. Efforts to reduce subscapularis-related complications and improve glenoid exposure led some surgeons to question traditional surgical techniques.

Referring to various embodiments of shoulder arthroplasty procedures in further detail, a subscapularis split, rotator interval and sub-subscapularis approach can spare the rotator cuff and provide improved functional outcomes for patients. Rotator cuff-sparing total shoulder arthroplasty may improve post-operative pain, rehabilitation and subscapularis function and strength. A rotator cuff-sparing posterior approach to shoulder arthroplasty that utilizes the interval between the teres minor and infraspinatus and an in-situ osteotomy is described herein.

The posterior approach utilizes a split of the middle and posterior heads of the deltoid and the internervous plane between the teres minor and infraspinatus. Because it avoids subscapularis and posterior rotator cuff tendon release and repair, early active motion can be performed. In some embodiments, benefits of this approach include avoidance of subscapularis dysfunction or rupture, improved access to the retroverted glenoid, and the ability to perform posterior soft tissue balancing. Newer implants, including stemless humeral components have facilitated this approach for selected patients with reasonable proximal humeral bone. Additionally, this approach improves visualization of the humerus and glenoid over rotator interval and subscapularis-splitting approaches.

In some embodiments, total shoulder arthroplasty can be performed through a variety of surgical approaches. The posterior approach is described herein. The benefits of a posterior approach include improved visualization of the retroverted glenoid, the ability to perform posterior soft tissue balancing, and the ability to protect the overlying rotator cuff.

Typical surgical instruments can be used in this particular approach as well as some specialized instruments shown in FIGS. 1-21. Several of these, such as those shown in the Figures, are specially designed to enhance the exposure in a posterior shoulder arthroplasty. The posterior approach can be performed using a stemless shoulder component.

Referring now to FIGS. 39A-39B and FIGS. 41A-41Z, a method 1500 of performing a posterior approach shoulder arthroplasty is shown according to various embodiments of the present disclosure. The method 1500 may be performed by various entities, including a surgeon, technician, or other medical professional, or a robotic surgical system. It will be appreciated that while at least some portions of the method 1500 may be described in terms of sequential steps, various steps may be rearranged, modified, or omitted by those skilled in the art, such as for tailoring the performance of the shoulder arthroplasty to particular patient needs.

At 1505, a body 1800 of a patient may be oriented to provide appropriate access to the shoulder for a posterior approach. In some embodiments, the patient may be placed in a lateral position (e.g., as compared to an anterior approach, in which the patient is placed supine with an arm board at the side). Orienting the patient may include placing an axillary roll. Orienting the patient may also include padding bony prominences. In some embodiments, orienting the patient includes adducting an arm of the patient (e.g., an arm adjacent to the shoulder to be operated on) to be placed across the body, which can improve glenoid exposure. The arm may be maximally adducted. In some embodiments, the shoulder anatomy 1804 is labeled. For example, the posteriolateral corner 1806 of the acromion (e.g., acromion 1402) may be marked using a marking pen. The humeral head 1808 may be outlined as well.

At 1510, an incision is made, such as to expose or begin exposure of a surgical site or an implant site. The incision may be made from the arm to the acromion 1402. For example, the incision may be made from the mid posterior arm 1802' to a point 1810 just above the axilla approximately two to three centimeters posterior to the post lateral tip of the acromion 1402. In some embodiments, electrocautery is utilized (e.g., along the incision) to coagulate any skin bleeders. In some embodiments, dissection is carried down through skin and subcutaneous tissues.

At 1515, the deltoid is exposed. For example, Gelpi retractors 1812 may be placed, and Metzenbaum scissors 1814 may be used to expose an inferior aspect 1816 of the deltoid.

At 1520, the sub-deltoid space (e.g., a space under the deltoid relative to a direction from which the deltoid is being accessed) is exposed. A Richardson retractor 1818 may be used to pull the deltoid more proximally such that the sub-deltoid space 1820 is exposed.

At 1525, the posterior and middle heads of the deltoid may be dissected. For example, a finger can be used to bluntly dissect between the posterior and middle heads of the deltoid. In some embodiments, electrocautery is used to further this exposure. In some embodiments, using electrocautery may include applying the electrocautery at a distance from the axillary nerve (e.g., distally to the exposure) to avoid the axillary nerve.

At 1530, a subacromial space may be entered. For example, posterior fascial bands 1822 across the rotator cuff may be incised to enter the subacromial space. In some embodiments, posterior fascial bands may be incised without cutting through the rotator cuff as performed in anterior approach shoulder arthroplasty, which may help preserve the rotator cuff and reduce the likelihood of and extent of post-operative recovery necessary for the rotator cuff.

At 1535, the teres minor 1408 (which may be relatively inferior) and the infraspinatus 1406 (which may be relatively superior) are identified. For example, the infraspinatus 1406 may be identified based on the infraspinatus 1406 being relatively more muscular, while the teres minor 1408 may be identified based on the teres minor having white fascial bands. In some embodiments, a tagging stitch 1824 may be applied to the infraspinatus 1406 and the teres minor 1408.

At 1540, traction is applied to expose the capsule underlying the rotator cuff. At 1545, the rotator cuff is taken laterally in a split to the greater tuberosity. For example, the rotator cuff may be repositioned, or portions of the rotator cuff may be separated, without cutting through the rotator cuff (e.g., division of the subscapularis tendon).

At 1550, exposure of the implant site is enhanced. For example, exposure of the capsule 1826 and rotator cuff can be enhanced. Retractors 1828 (e.g., Army Navy retractors) may be placed superiorly and inferiorly to enhance the exposure of the capsule and rotator cuff.

At 1555, the capsule can be visualized; two retractors 1830 (e.g., Hohmann retractors), one proximally and one distally, may be applied, such as to better expose the capsule.

At 1560, a capsulotomy is performed. Performing the capsulotomy may include cutting into the capsule. In some embodiments, a T-shaped capsulotomy is made from the lateral aspect of the greater tuberosity to the glenoid.

At 1565, a superior capsule relieflet is taken. For example, a T-capsule from the T-shaped capsulotomy may be taken superiorly up and around the superior aspect of the shoulder. A tagging stitch may be placed into the superior capsule relieflet. In some embodiments, a T-shaped capsulotomy 1832 may be made from the inferior aspect of the capsule. The T-shaped capsulotomy from the inferior aspect of the capsule may be taken along the humeral neck or along the inferior humeral osteophytes. In some embodiments, a tagging stitch may be applied to the inferior capsule relieflet such that traction can be performed.

At 1570, the superior aspect of the shoulder may be at least one of exposed or protected. A retractor 1834 may be used to perform the exposure and/or protection. For example, a Crego retractor may be placed superiorly to expose and protect the superior aspect of the shoulder.

At 1575, a humeral osteotomy is performed. Performing the osteotomy may include removing bone pieces in and around the humeral head to prepare the humeral head for an implant. In some embodiments, a guide 1836 is placed such that version and angulation of the osteotomy (e.g., of the cut made to perform the osteotomy) may be assessed and more easily performed. The osteotomy can then be performed after guide placement. In some embodiments, performing the osteotomy can include removing inferior humeral osteophytes 1838.

In some embodiments, performing the method 1500 can include exposing the glenoid, which may include one or more of the procedures described at 1580-1585. At 1580, the arm 1802 may be adducted across the body. At 1585, an anterior glenoid retractor 1840 may be placed. In some embodiments, the anterior glenoid retractor may be configured to facilitate improved exposure once the surgeon goes to the anterior aspect of the shoulder. The anterior glenoid retractor may be relatively large (e.g., as compared to other retractors described herein).

At 1590, the glenoid is visualized from the anterior aspect 1800' of the patient. At 1595, a central aspect of the glenoid is marked, which can facilitate further operations on the glenoid.

At 1600, the glenoid is reamed. In some embodiments, a drill 1842 is inserted into the glenoid 1844 such that a reamer 1846 may be placed. Glenoid reaming can be performed to prepare the glenoid to receive an implant. Glenoid reaming can be performed to shape the glenoid into an appropriate geometry to facilitate desired kinematics for movement of the arm relative to the shoulder after the procedure is completed.

At 1605, a glenoid guide 1848 is placed, which can help guide insertion and alignment of implants. At 1610, a first glenoid drill can be placed, followed by a peg in the inferior aspect of the glenoid, and a second glenoid drill can be placed superiorly (e.g., in the superior aspect of the glenoid; superior to the first glenoid drill). At 1615, a broach 1850 is placed and impacted in position.

At 1620, once the broach is in position, a trial implant 1852 is placed. At 1825, the trial 1852 implant is removed (e.g., based on the trial implant 1852 position satisfying an implant position condition, such as for facilitating appropriate or desired arm movement). Glenoid cementation techniques can be used to prepare the implant site for implantation. In some embodiments, thrombin soaked sponges are placed. At 1630, cement is placed to secure the implant site.

At 1635, the glenoid 1854 is impacted in position. In some embodiments, excess cement may be removed (e.g., using a Freer elevator).

At 1640, the humerus is exposed. In some embodiments, the humerus is exposed by one or more of adduction, internal rotation, and forward flexion of the arm (or the humerus at the shoulder), such as to return to the posterior aspect of the implant site 1800.

At 1645, a retractor is placed in an interval of the rotator cuff (e.g., where the rotator cuff is split). In some embodiments, the retractor may be placed below the calcar. At 1650, an additional retractor (e.g., Richardson retractor) is placed more laterally than the retractor placed in the interval, such as to expose the cut of the humeral head.

At 1655, a trial humeral head component 1856 is placed. In some embodiments, a pin 1858 is placed through a central aspect of the trial humeral head component 1856, such as to verify that a position of the humerus (or of the trial humeral head component on the humerus) is accurate. At 1660, a surface of the humeral osteotomy is sized (e.g., after removing the trial humeral head component 1856). The trial humeral head component 1856 can be removed and the humeral osteotomy surface sized.

At 1665, a baseplate 1860 can be secured to the glenoid. For example, the baseplate 1860 can be inserted and tapped into position. The baseplate 1860 may be selected based upon anatomical or kinematic requirements for the shoulder of the patient.

At 1670, the trial humeral head component 1856 is placed into position. In some embodiments, placing the trial humeral head component 1856 includes placing the trial humeral head component 1856 based on a desired spatial relationship between the greater tuberosity and the humeral head. An imaging device may be used to identify the spatial relationship between the greater tuberosity and the humeral head. For example, a mini C-arm can be used to identify the accuracy of the placement of the trial humeral head component along the glenoid (e.g., based on receiving image data of the implant site and trial humeral head component 1856 from the mini C-arm). In some embodiments, the position of the trial humeral head component 1856 can be modified based on the accuracy of the placement to achieve the desired spatial relationship. At 1675, the shoulder is reduced. For example, the humerus can be aligned in a desired anatomical relationship (e.g., orientation) relative to the glenoid.

At 1680, the trial humeral head component is removed and the real humeral baseplate 1862 is impacted into position. In some embodiments, the baseplate 1862 is impacted to be flush with the cut surface of the humeral head. At 1685, an inserter is removed. In some embodiments, the baseplate 1862 is cleaned. The real humeral implant 1864 is placed (e.g., based on the range of motion and alignment of the shoulder meeting corresponding criteria). In some embodiments, placing the real humeral implant 1864 can include securing the real humeral implant 1864 to the real humeral baseplate 1862 via a Morse taper. In some embodiments, placing the real humeral implant 1864 includes impacting the real humeral implant into position 1864 and checking the Morse taper to confirm that the real humeral implant 1864 is engaged to the real humeral baseplate 1862. The shoulder can be reduced. In some embodiments, the accuracy of the cut is assessed, such as by using an imaging device such as the mini C-arm.

At 1690, the T-shaped capsulotomy is repaired. In some embodiments, the T-shaped capsulotomy is repaired using at least one figure of eight stitches. The capsule and posterior rotator cuff are repaired. In some embodiments, the deltoid is repaired. The capsule is repaired to the rotator cuff. In some embodiments, the T-shaped capsulotomy can easily be visualized and the capsule is repaired to the lateral portion of the rotator cuff (e.g., based on the visualization). In some embodiments, the capsule can be imbricated, such as to improve soft tissue balancing of the posterior aspect of the humerus. In some embodiments, figure of eight stitches are placed in the capsule in order to improve the strength of the repair. After figure of eight stitches are placed into the capsule and the capsule is fully repaired, the posterior rotator cuff split between the teres minor and infraspinatus can be repaired. For example, a running figure of eight rotator cuff stitch is placed. In some embodiments (e.g., if there is demonstration of preoperative subluxation of the posterior shoulder), an imbrication stitch here can be performed. As compared to an anterior approach, in which a subscapularis takedown may require significantly more complicated rotator cuff repair procedures, and may result in chronic nerve denervation, weakness, tendon dysfunction, or glenoid loosening, the posterior approach described herein can facilitate improved shoulder recovery.

In some embodiments, post-operatively, the patient is allowed to be placed in a sling for one to two weeks but active motion may be utilized at any time when pain allows. Posterior joint stabilization precautions can be put in place for a total of six weeks. For example, the a combination of adduction and forward flexion with a forced posterior load may be restricted. After the capsule and rotator cuff are closed, range of motion may be assessed. It will be appreciated that the patient can have near full range of motion and forward flection and full abduction and external rotation of 90 degrees adduction and an extremely stable shoulder.

Figure 40A:
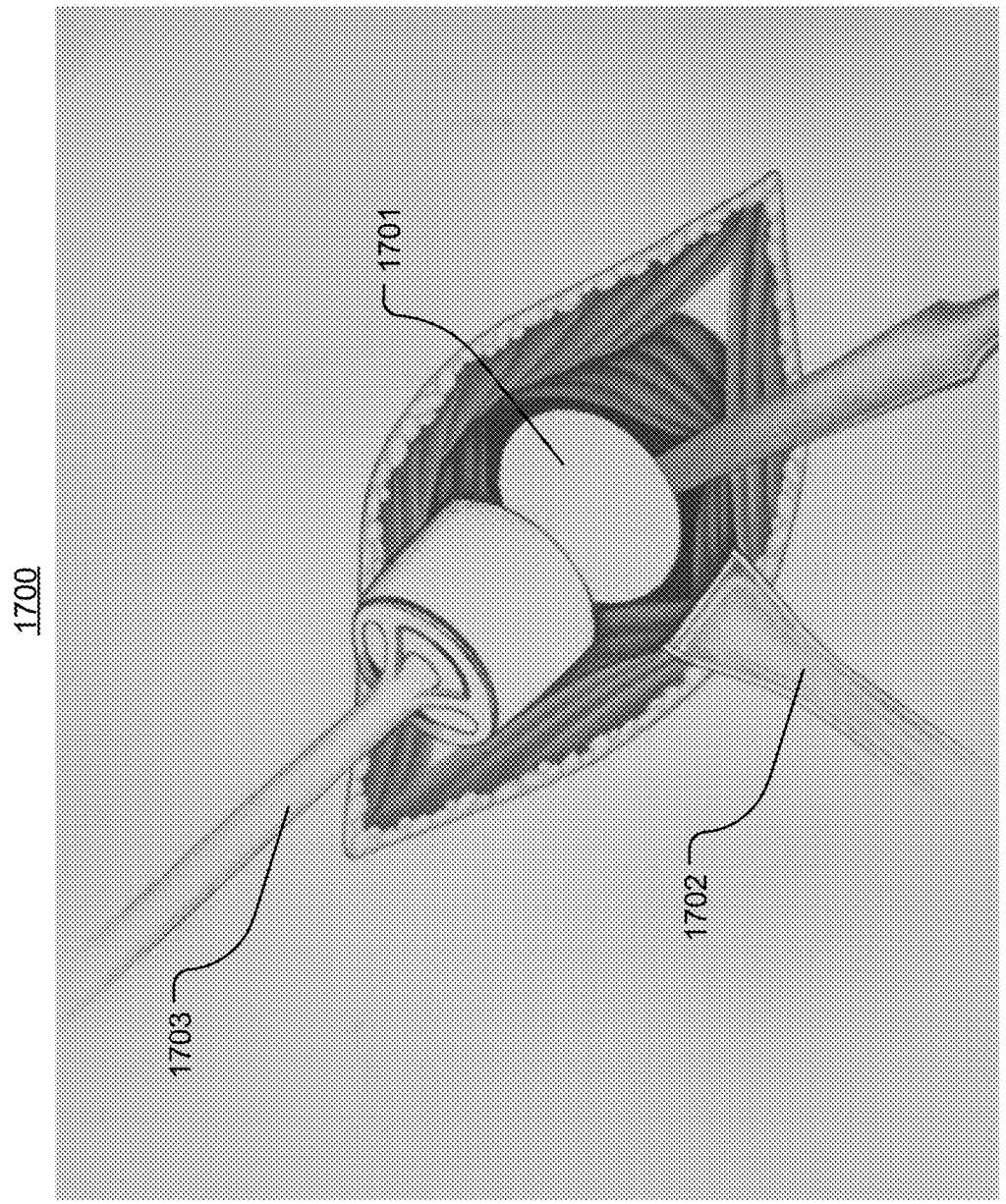
FIGS. 40A-40C are schematic diagrams illustrating example shoulder anatomies on which a posterior approach rotator cuff sparing total shoulder arthroplasty is being performed.
Figure 40B:
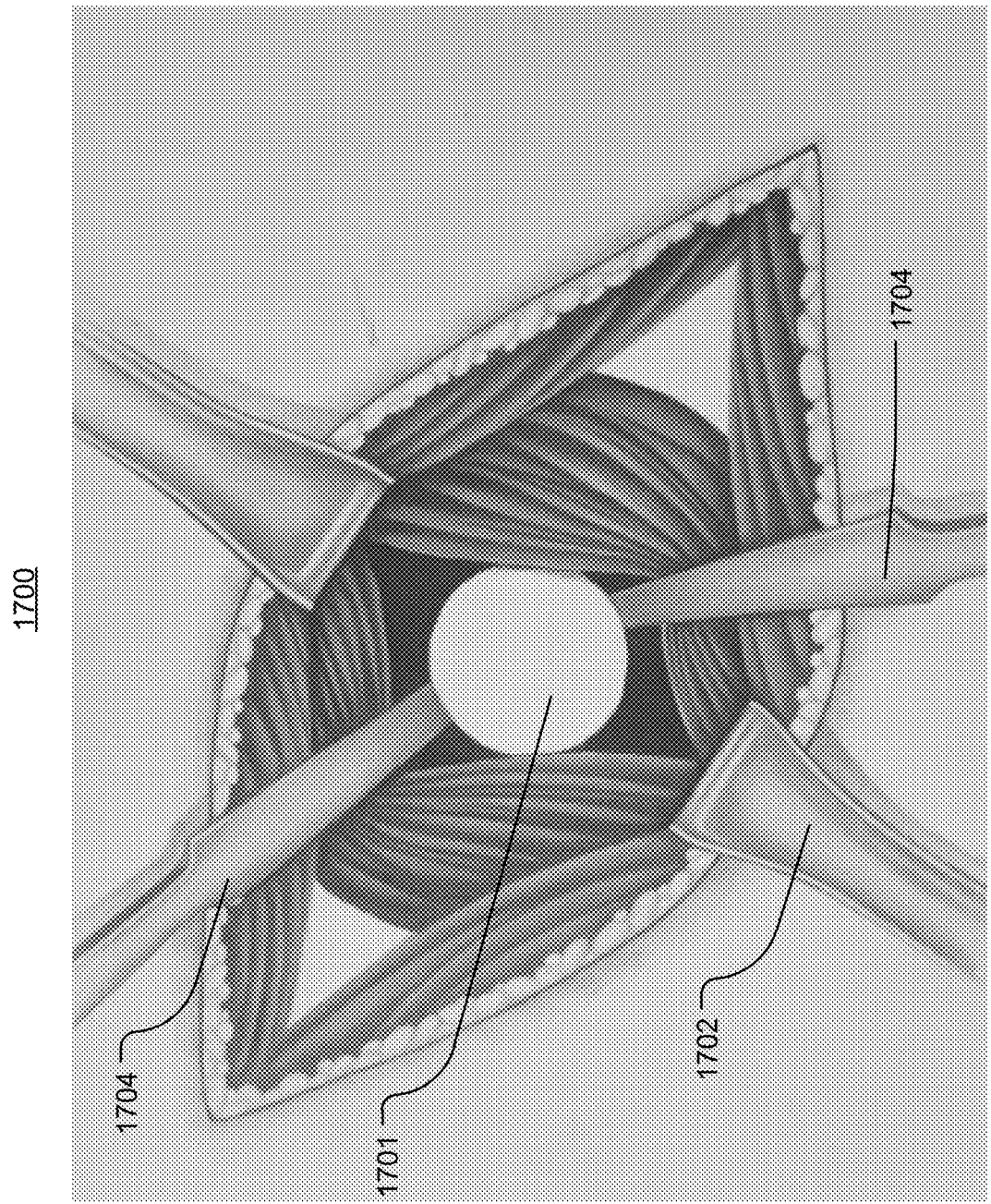
Figure 40C:
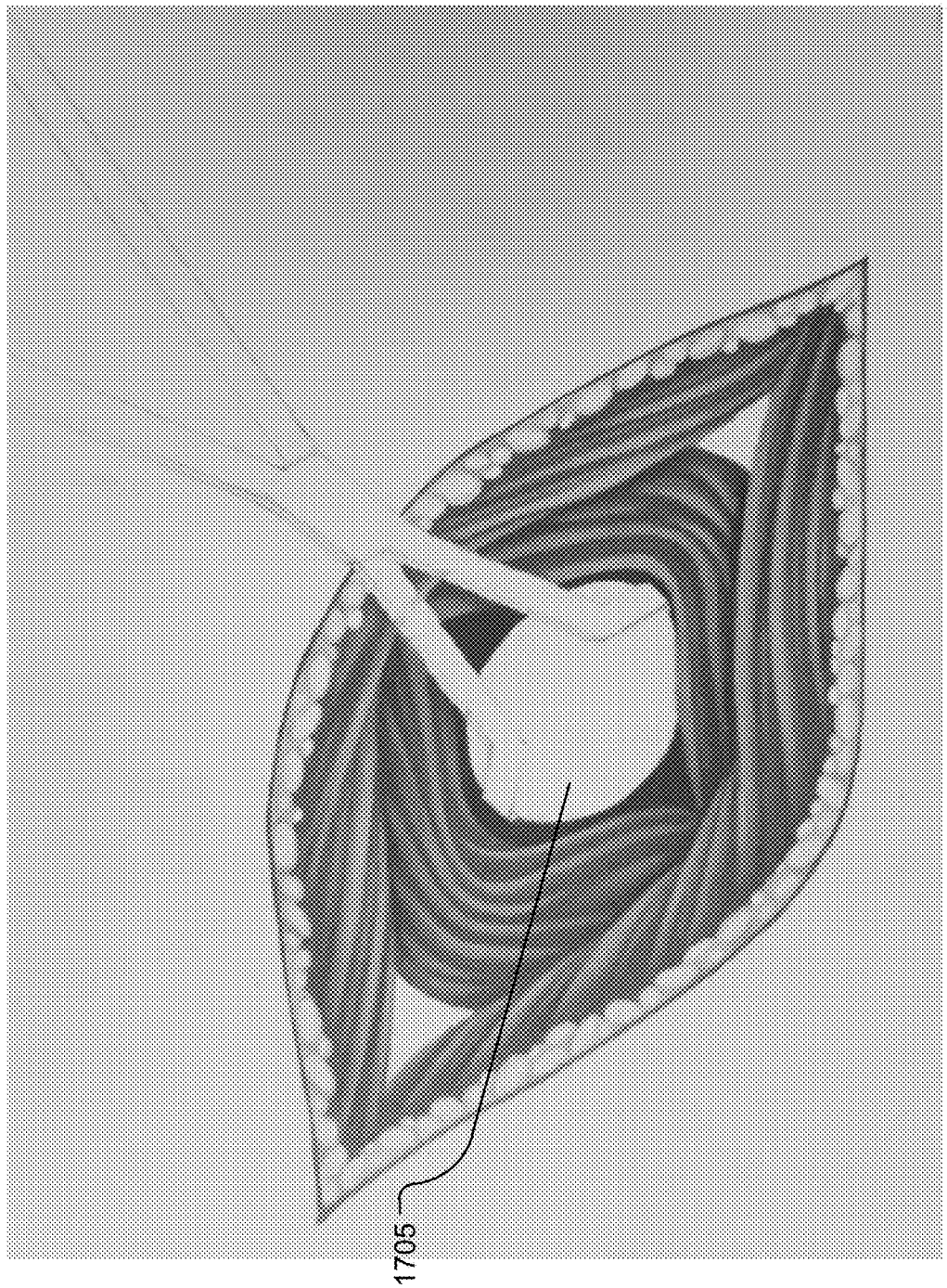
Figure 41A:
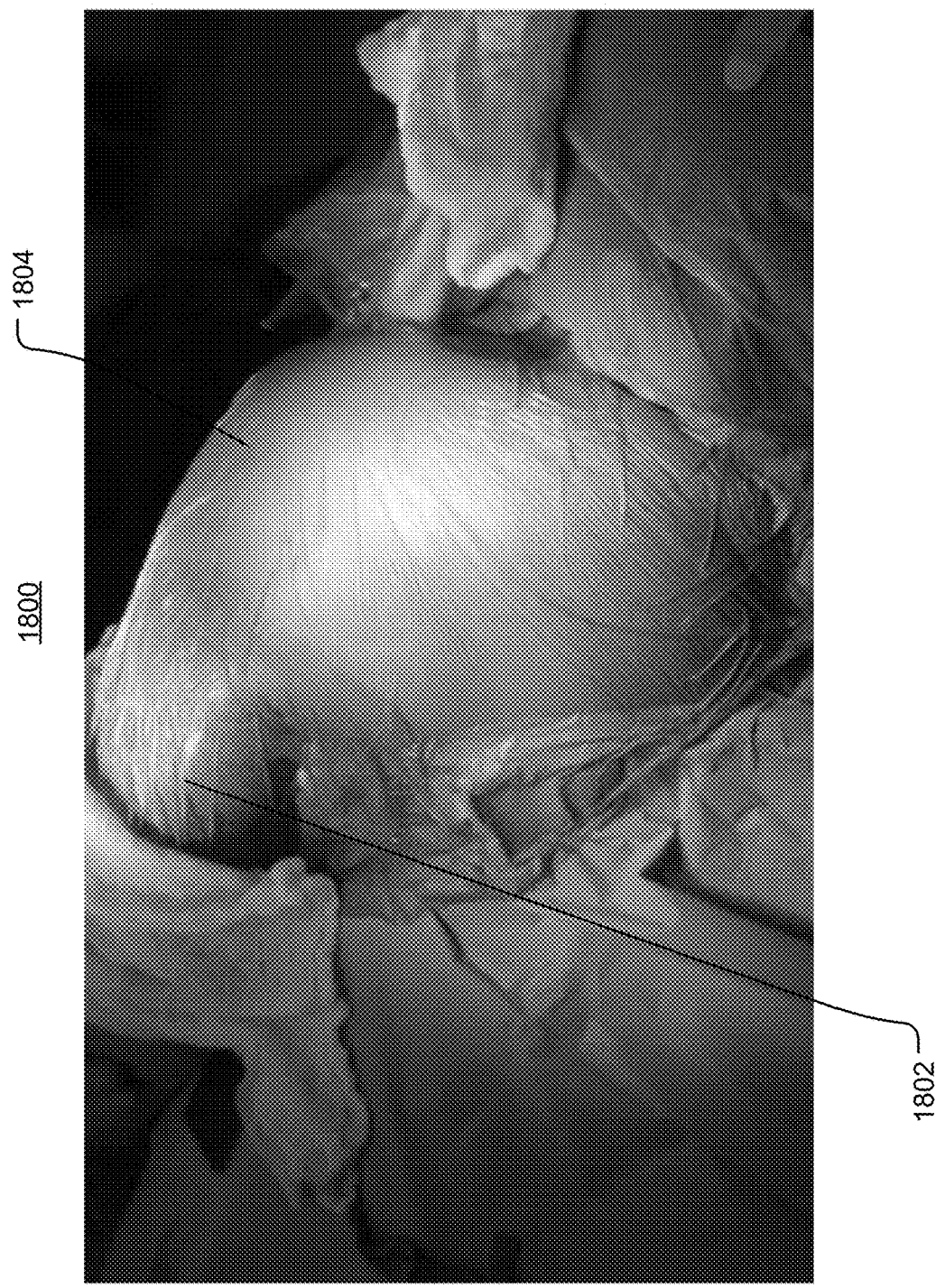
FIGS. 41A-41Z are images illustrating an embodiment of performing the posterior approach rotator cuff sparing total shoulder arthroplasty of FIGS. 39A-39B.
Figure 41B:
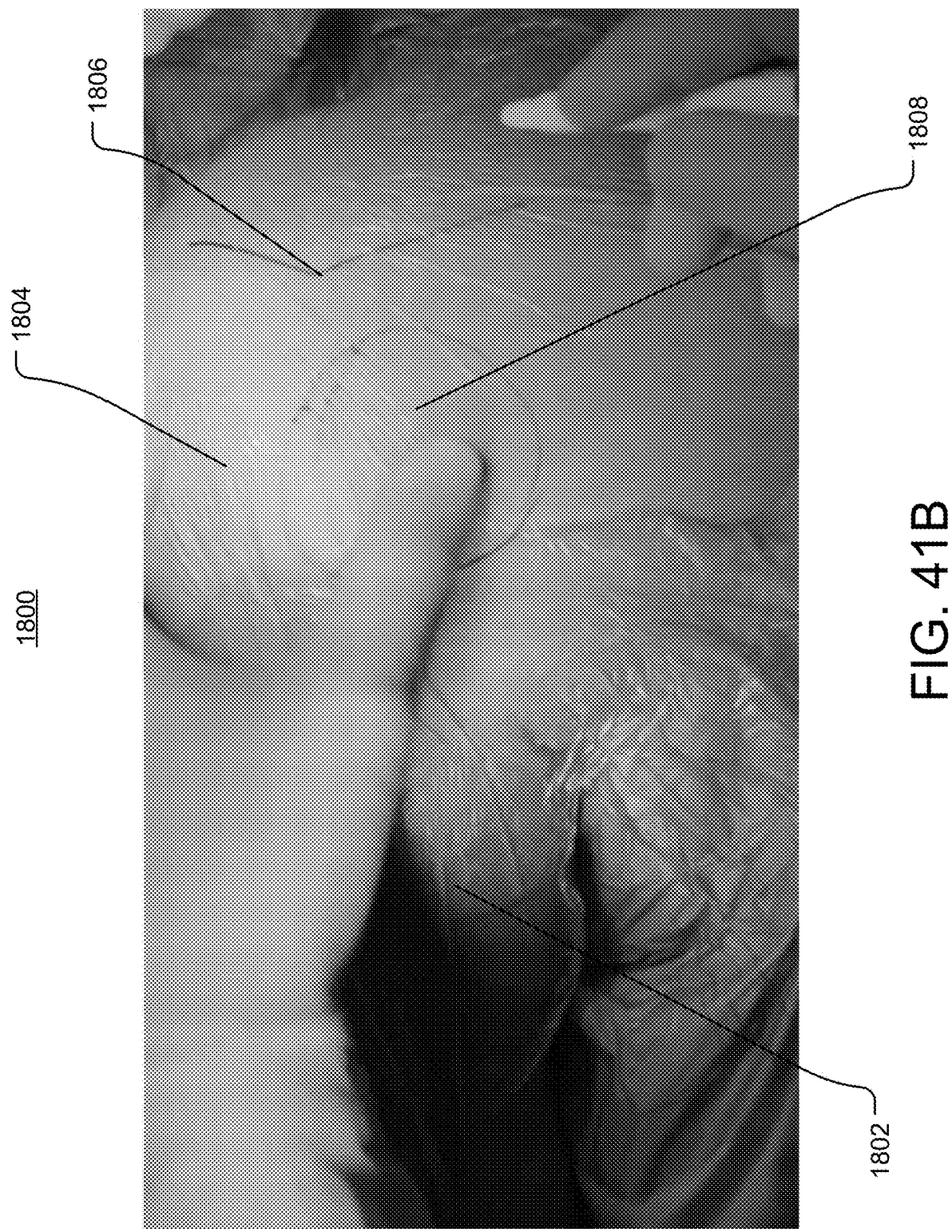
Figure 41C:
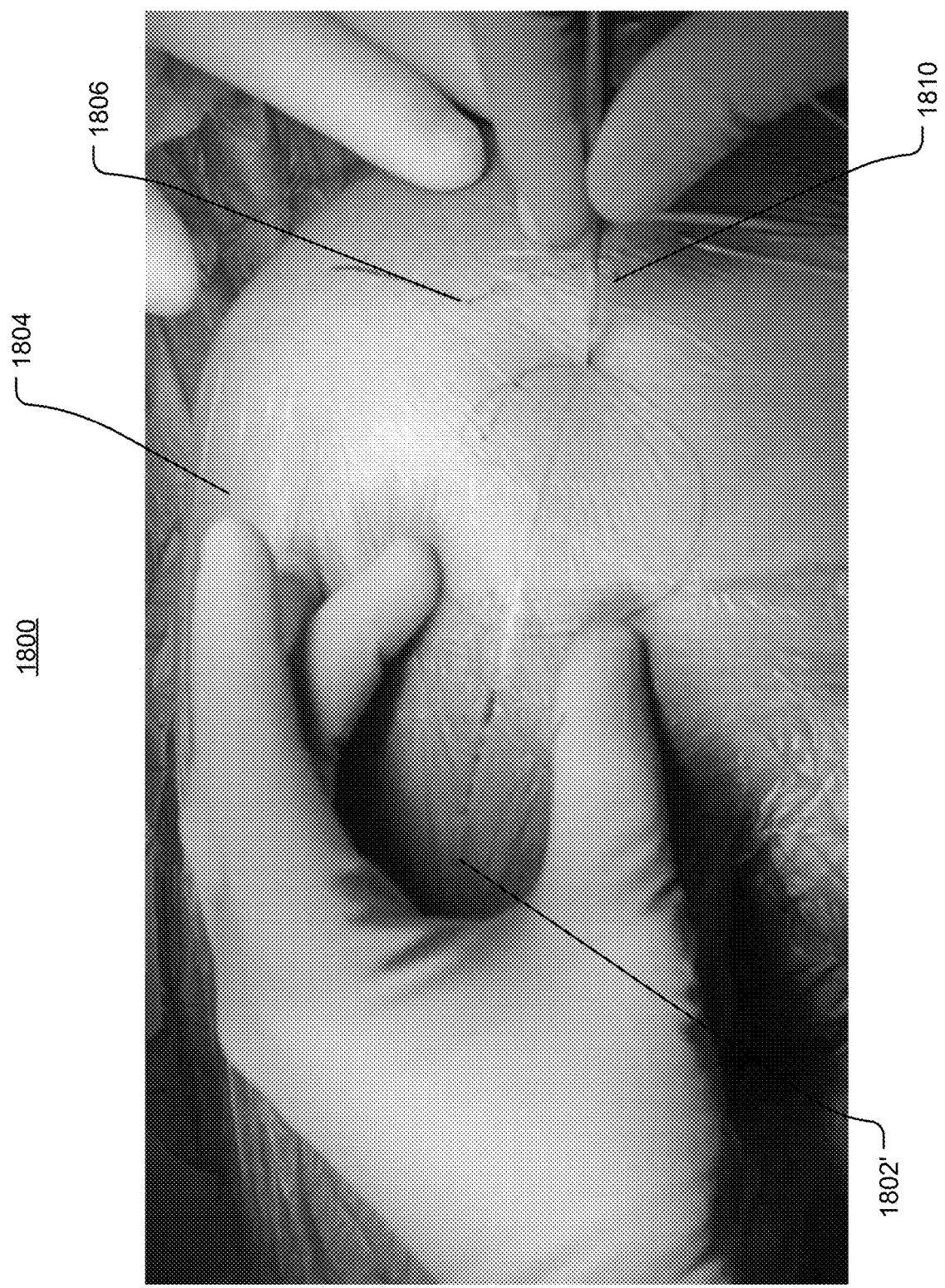
Figure 41D:
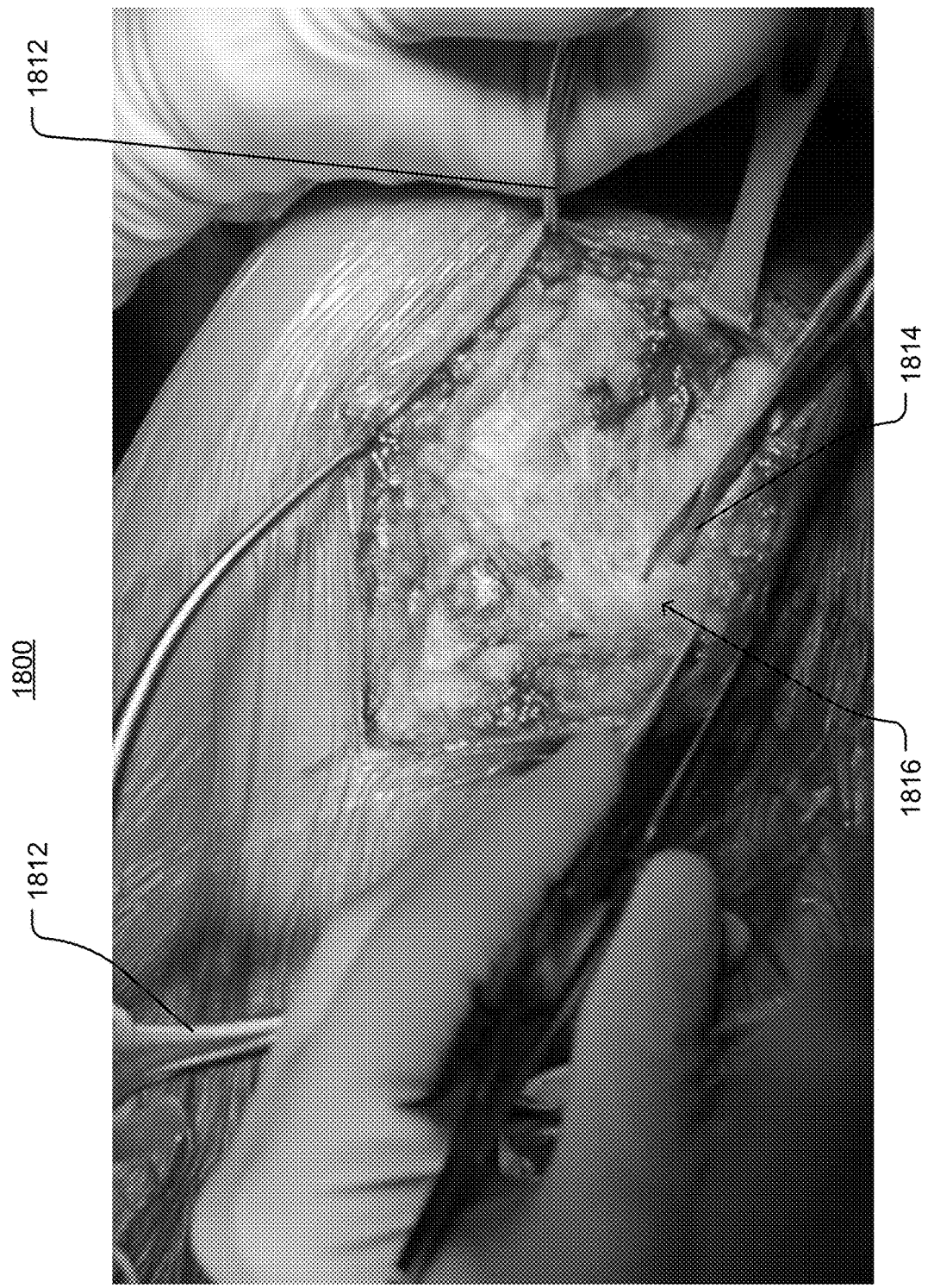
Figure 41E:
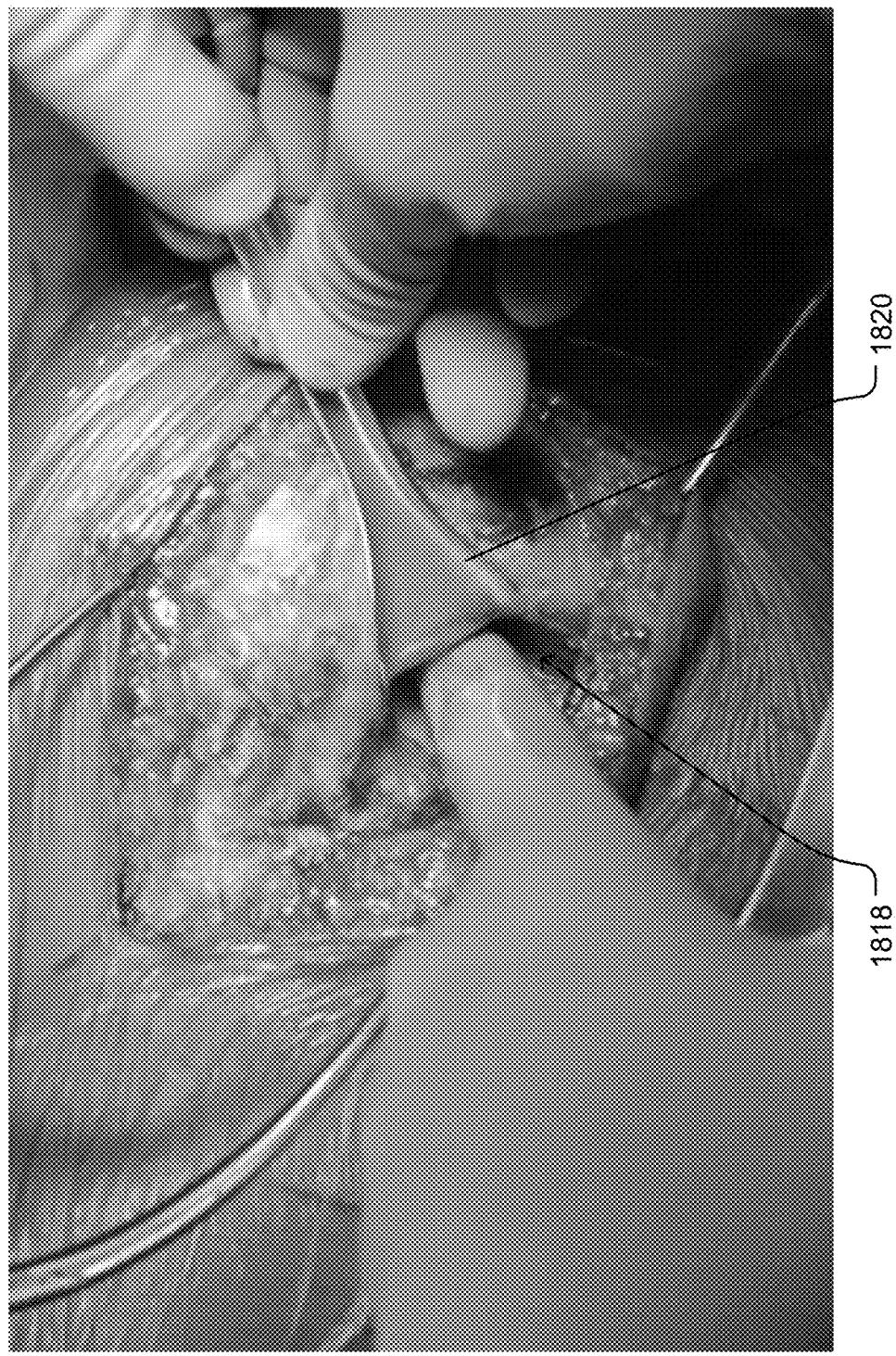
Figure 41F:
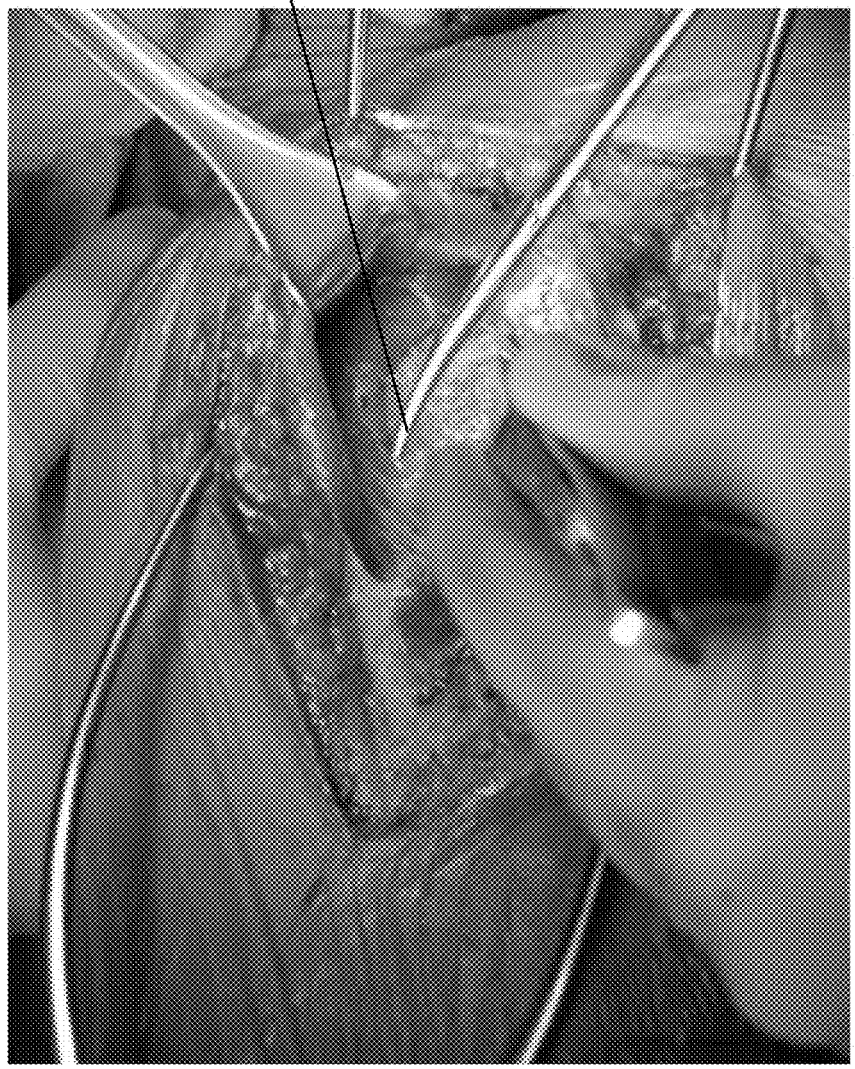
Figure 41G:
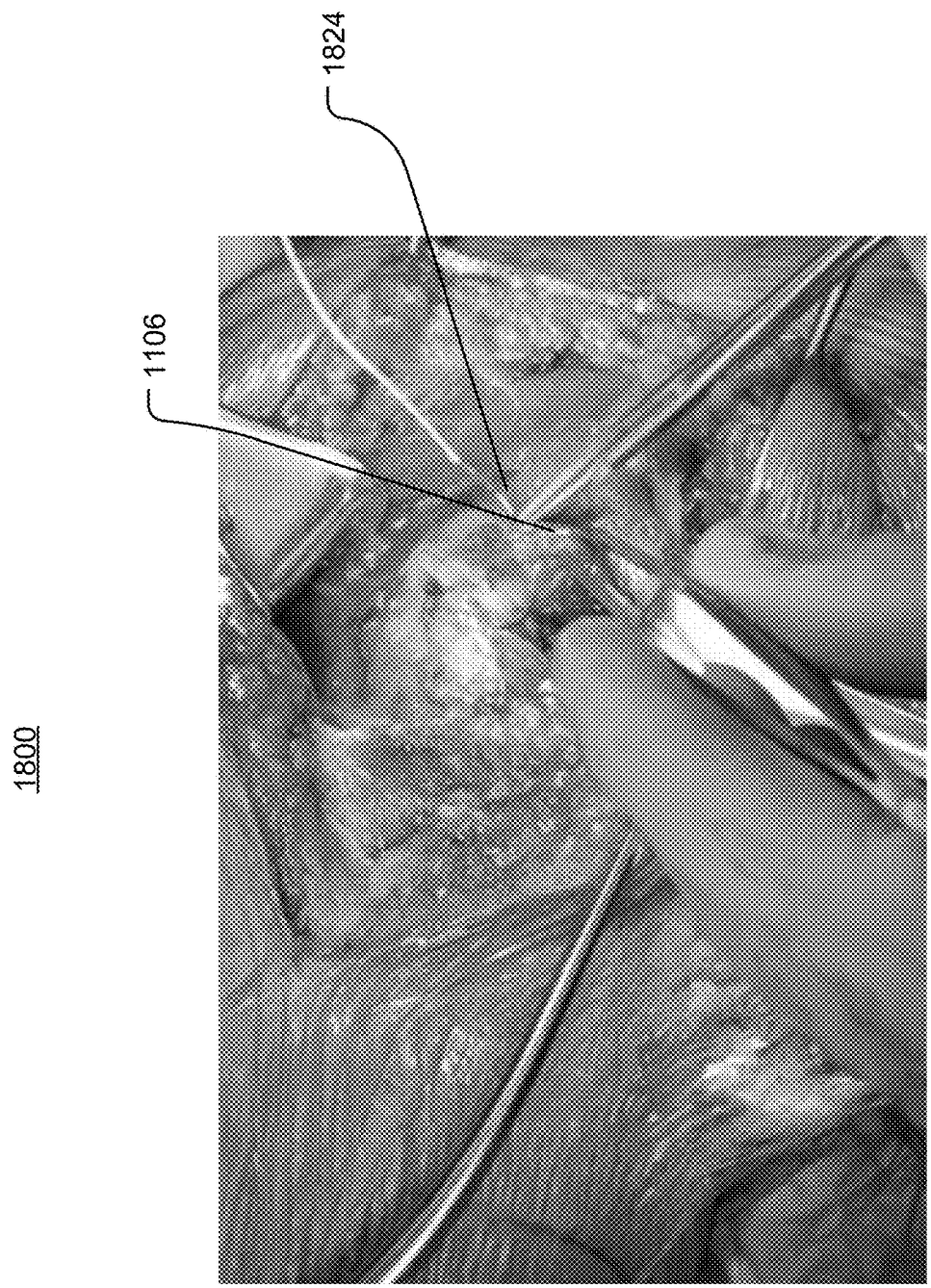
Figure 41H:
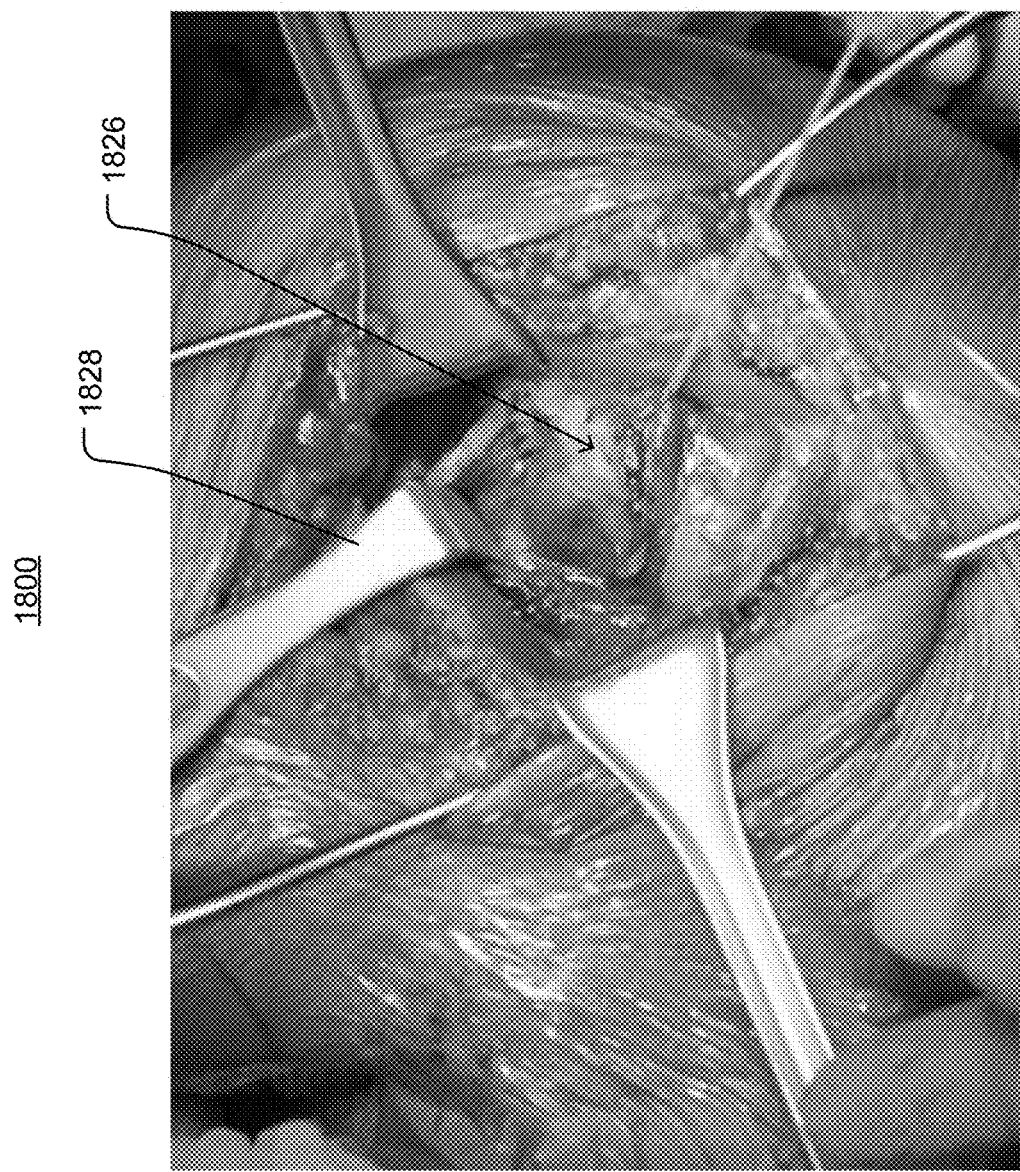
Figure 41I:
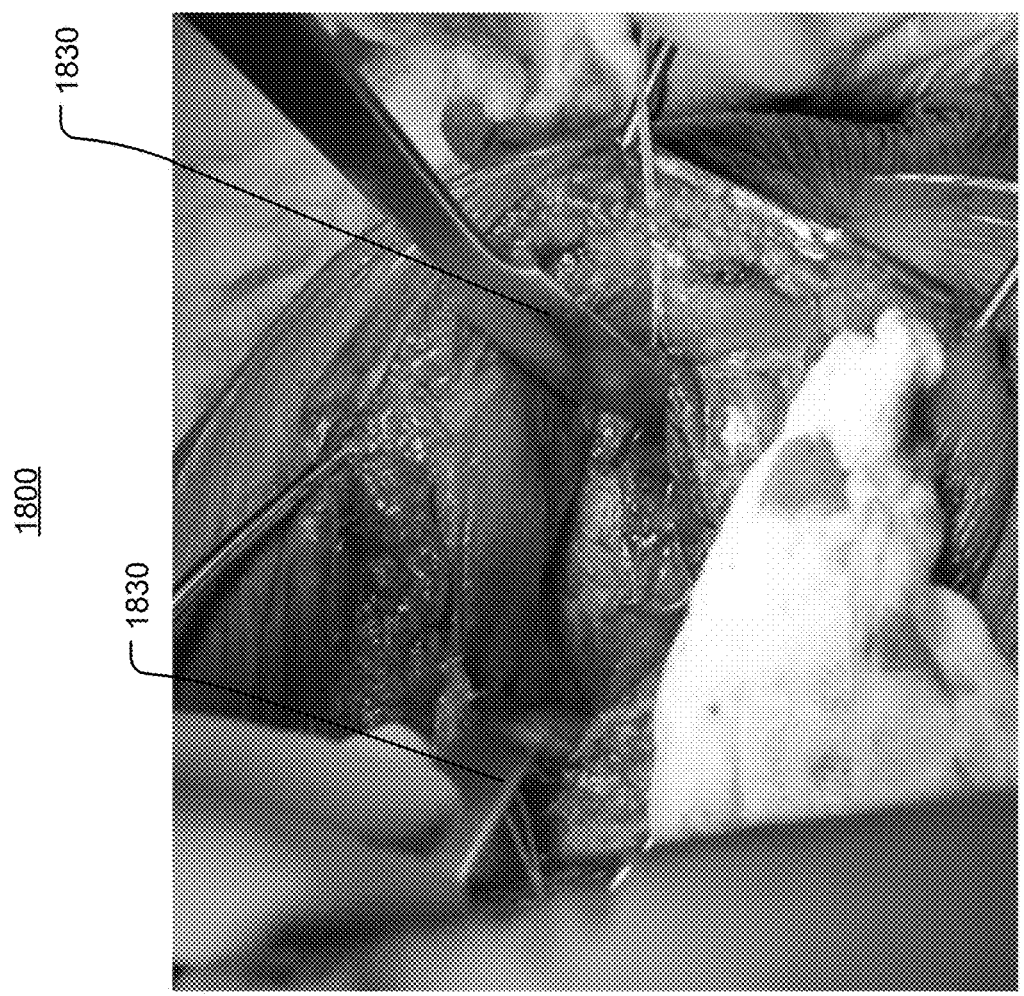
Figure 41J:
Figure 41K:
Figure 41L:
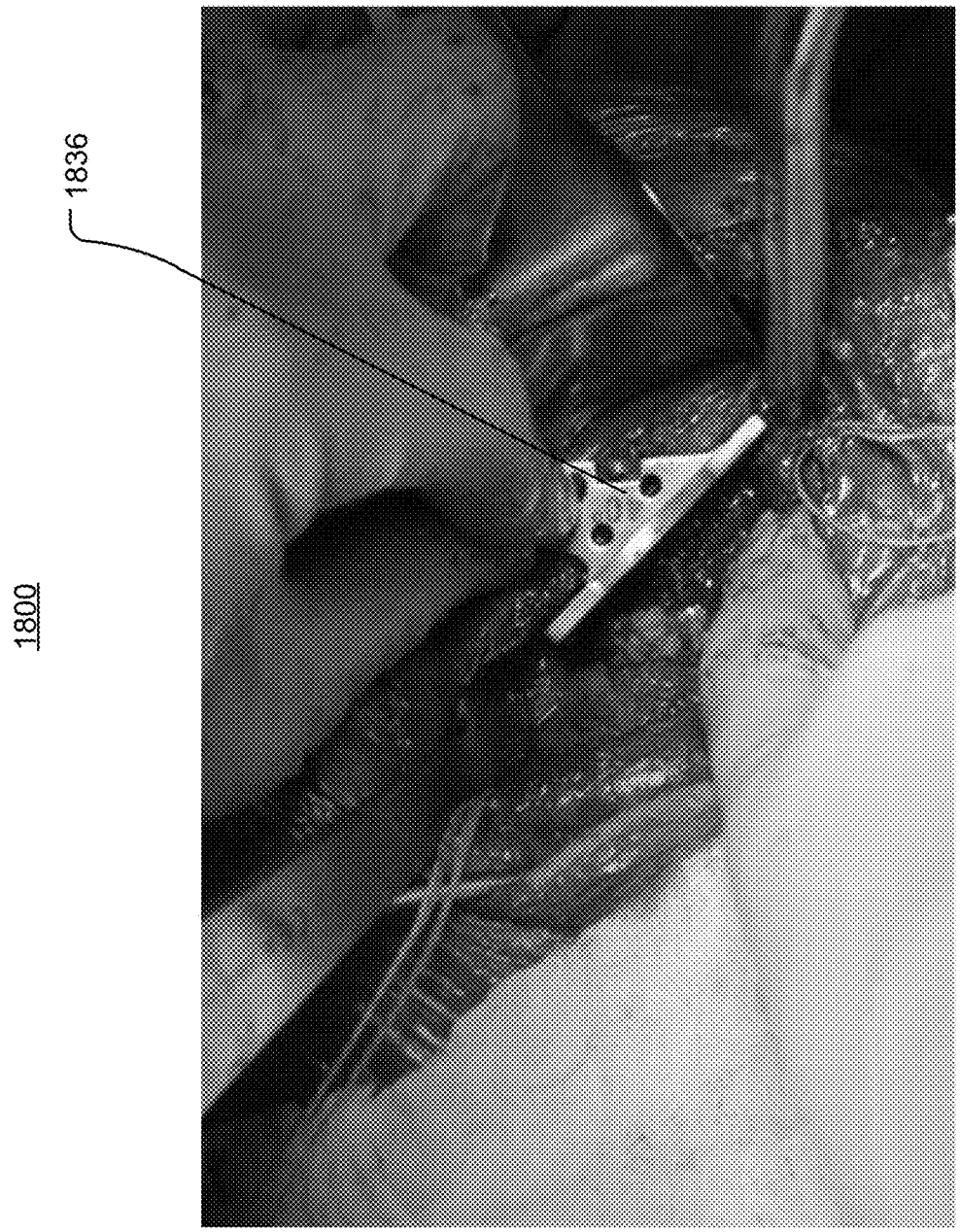
Figure 41M:
Figure 41N:
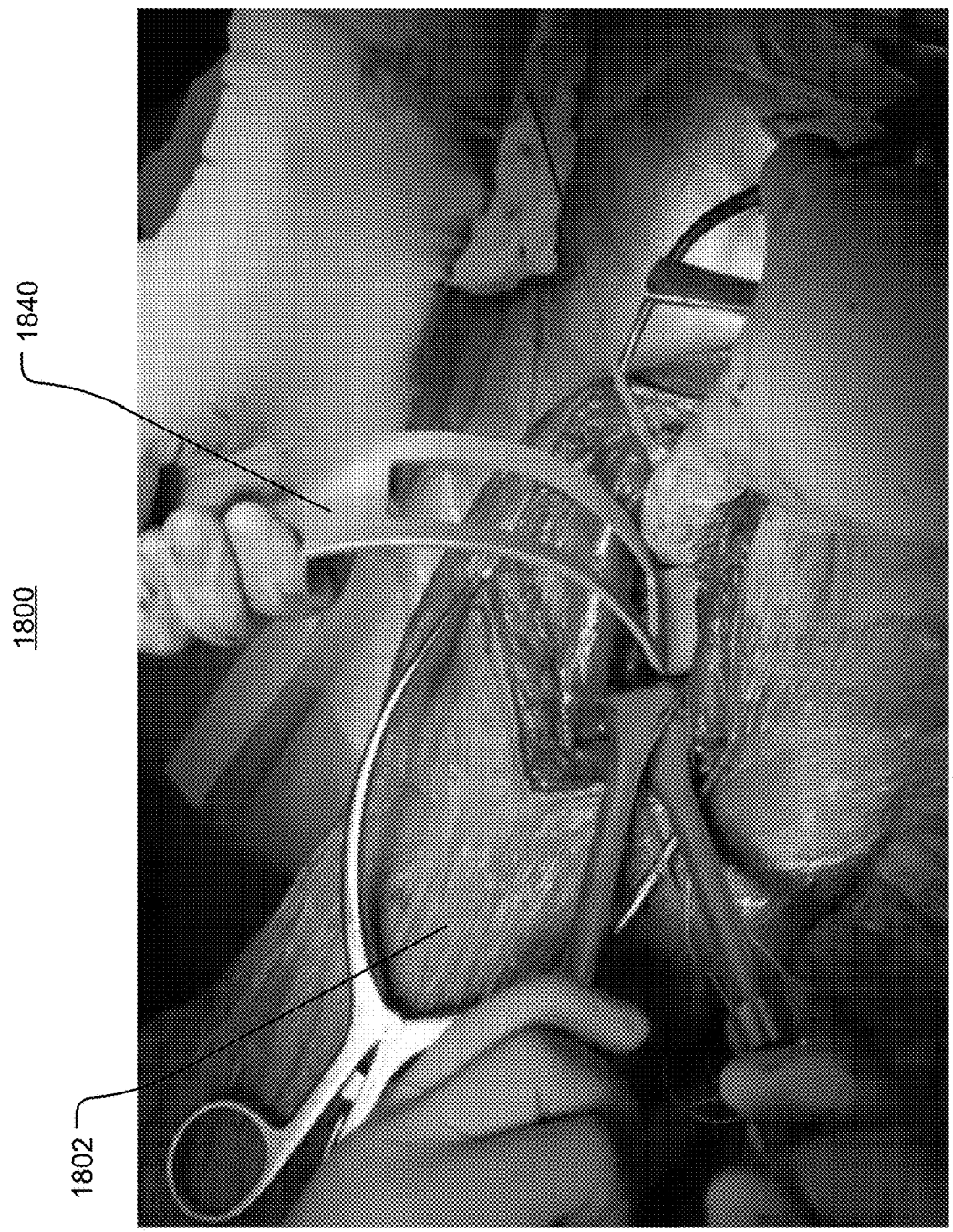
Figure 41O:
Figure 41P:
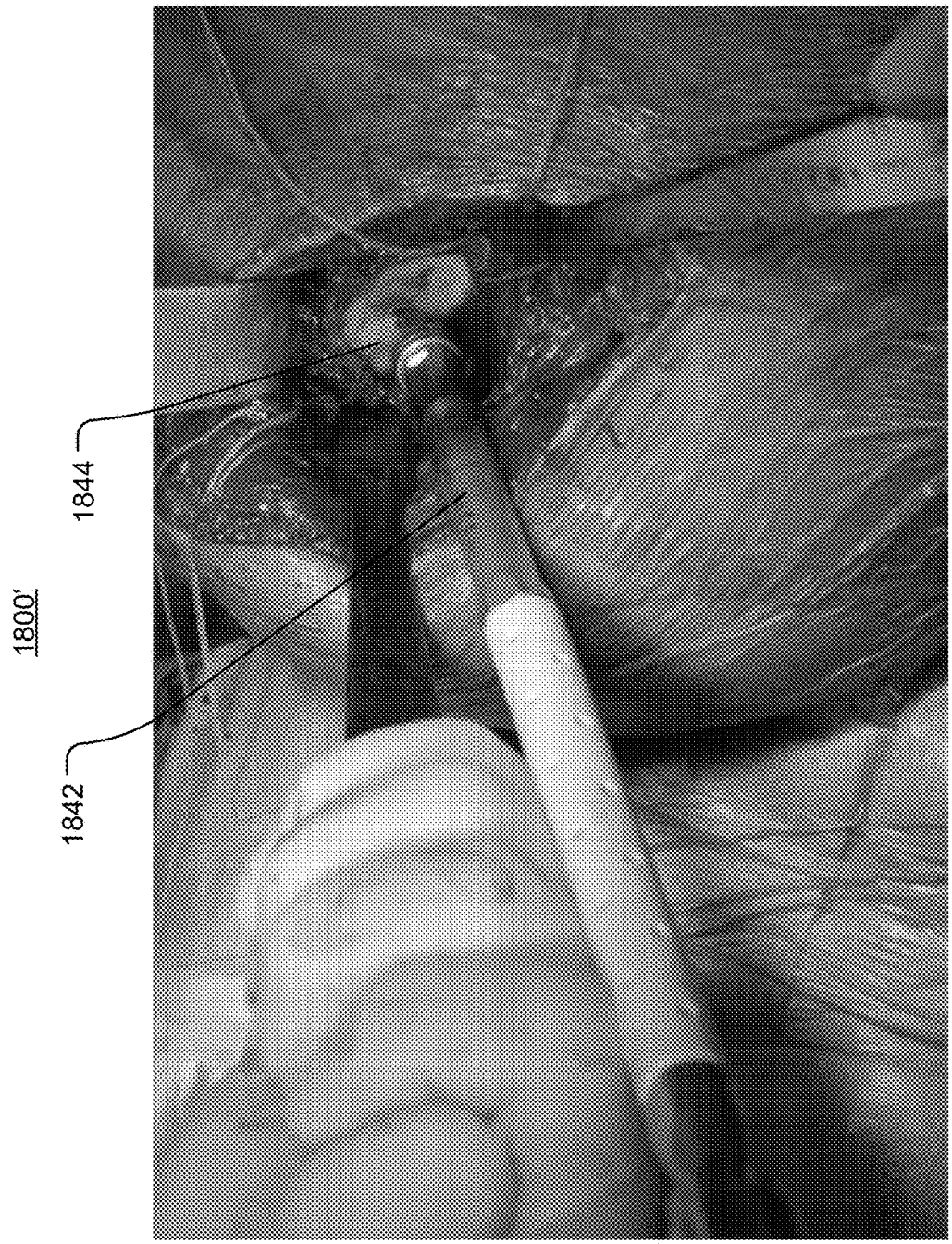
Figure 41Q:
Figure 41R:
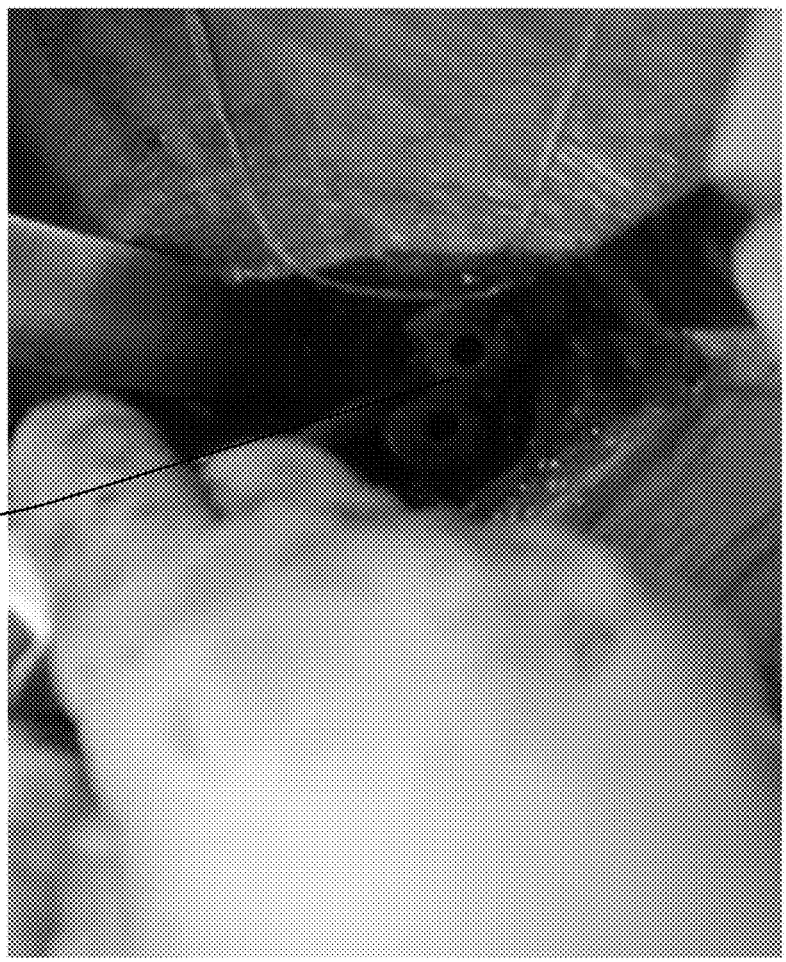
Figure 41S:
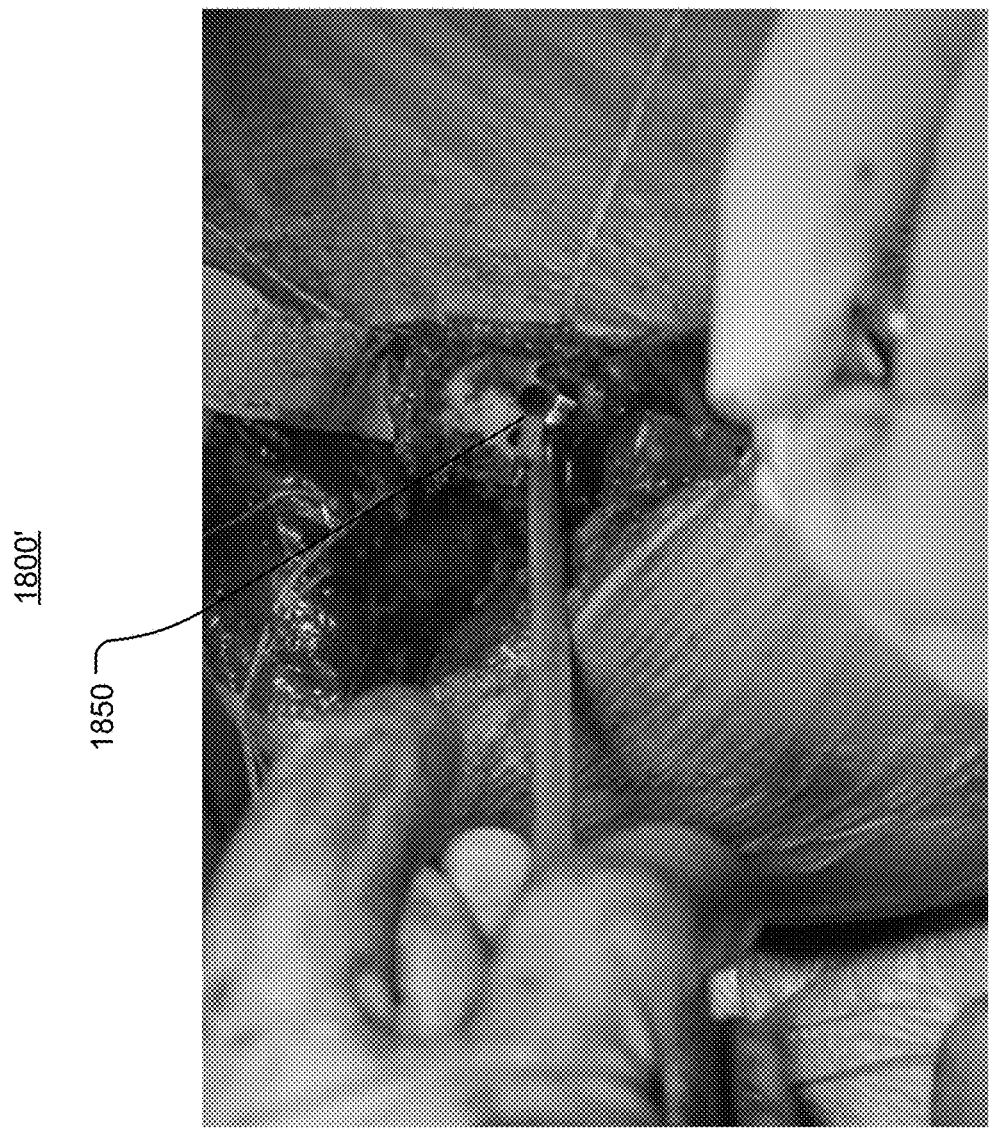
Figure 41T:
Figure 41U:
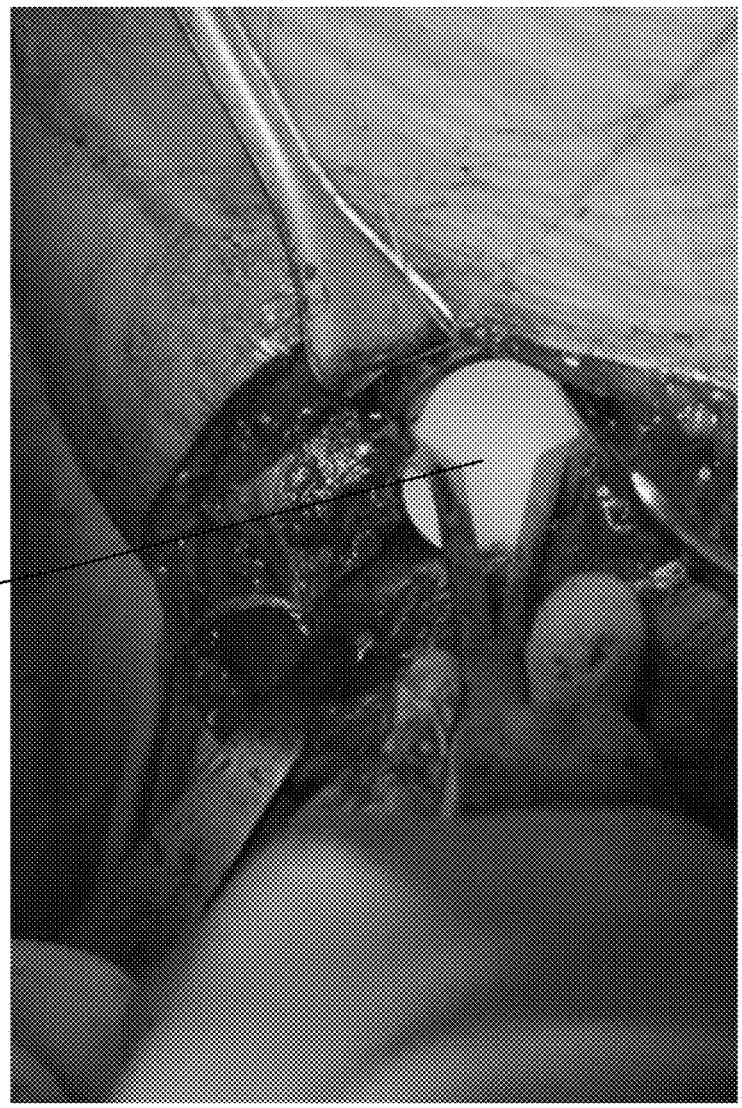
Figure 41V:
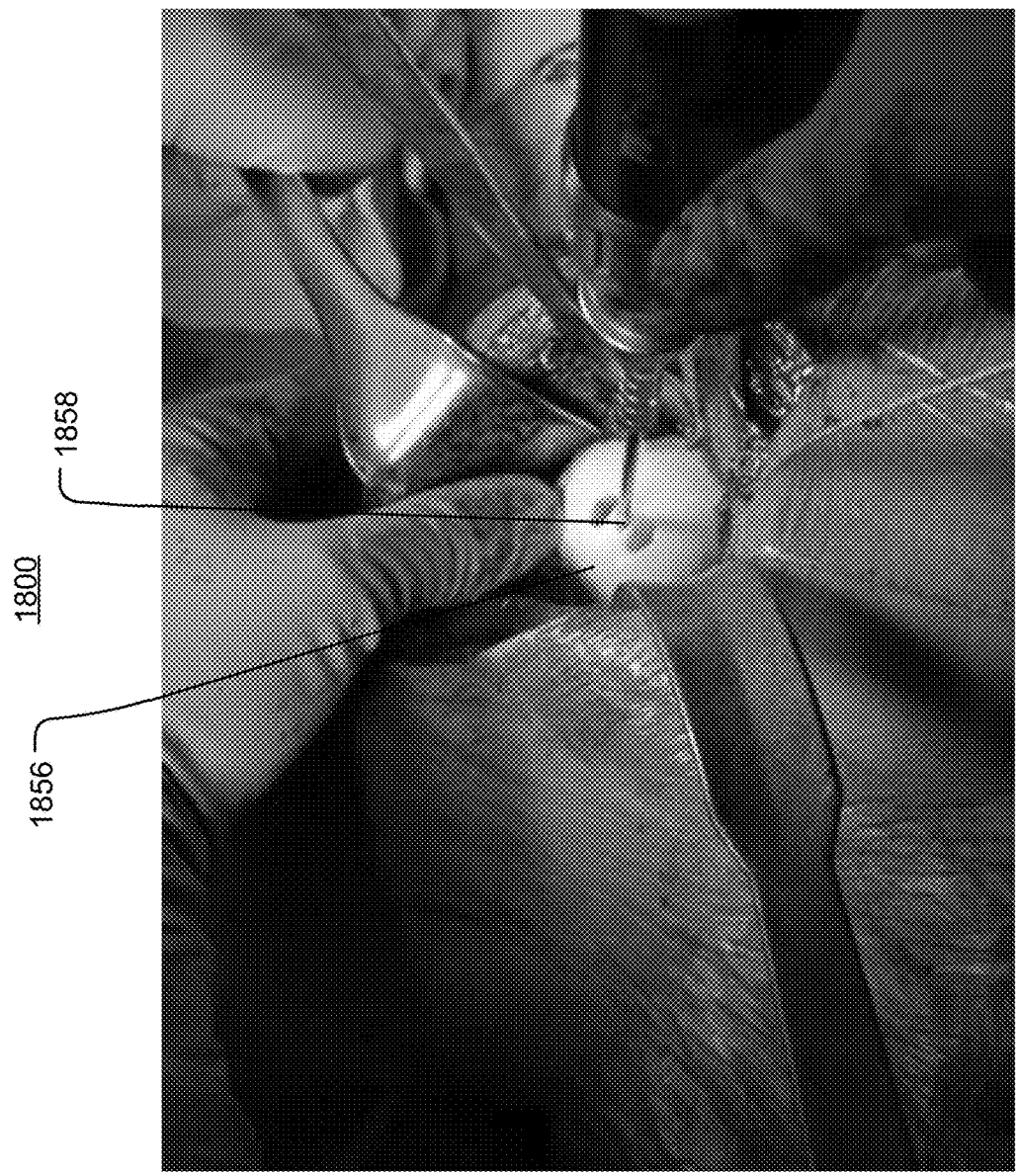
Figure 41W:
Figure 41X:
Figure 41Y:
Figure 41Z:

Referring back to FIGS. 40A-40C, various embodiments of posterior approach total shoulder arthroplasty are illustrated. As shown in FIG. 40A, an implant site 1700 (e.g., similar to the shoulder anatomies described with reference to FIGS. 38A-38B) including a capsule 1701 can be manipulated with a retractor 1702 (e.g., Richardson retractor) to improve exposure of the implant site 1700, while a humeral head implant 1703 can be impacted in position. As shown in FIG. 40B, retractors 1704 (e.g., Hohmann retractors) can be placed proximally and distally to better expose the capsule. As shown in FIG. 40C, an implant 1705 can be placed at the implant site 1700.

What is claimed is:

1. A humeral head implant system, comprising:
a head component including a first convex articulating surface configured to articulate in a shoulder cavity, a second bottom surface extending from a rim of the first convex articulating surface, a first cavity extending into the head component from the second bottom surface, and a second cavity extending into the head component from the first cavity, the second cavity defining a central second cavity axis, the head component defining a head axis extending through a center of the first convex articulating surface, the head axis spaced from and parallel to the second cavity axis;
a monolithic base component defining a central base axis passing through a center of the base component, the base component further defining a base cavity extending into the base component along the central base axis, the base component including a proximal face sized and shaped to be received within the first cavity of the head component so that the proximal face of the base component sits flush with the head component, the base component further including a plurality of legs adapted to anchor the base component into a humerus;

a first insert portion; and a second insert portion, wherein the first insert portion has a proximal end sized to be received within the second cavity of the head component, the second insert portion having a distal end sized to be received within the base cavity of the base component, the second insert portion defining an insert axis configured to be spaced from and parallel to the second cavity axis when the proximal end of the first insert portion is received within the second cavity of the head component and the distal end of the second insert portion is received within the base cavity of the base component.

2. The humeral head implant system of claim 1, wherein the head component is configured to be rotated about the second cavity axis relative to the first insert portion to adjust a position of a center of the head component relative to the first insert portion.

3. The humeral head implant system of claim 1, wherein the first insert portion is configured to form a Morse taper with the second cavity.

4. The humeral head implant system of claim 1, wherein the head component is sized to fit into an implant site targeted for total shoulder arthroplasty.

5. The humeral head implant system of claim 1, wherein the base component includes an extension extending distally away from the proximal face of the base component, the plurality of legs extending radially from the extension.

6. The humeral head implant system of claim 5, wherein the plurality of legs includes a first leg extending a first length from the extension, and two legs extending a second length from the extension.

7. The humeral head implant system of claim 5, wherein a distal end of the extension defines a distal end of the base component.

8. The humeral head implant system of claim 7, wherein the distal end of the extension defines a cylindrical channel.

9. The humeral head implant system of claim 8, wherein the cylindrical channel opens to the distal end of the base component.

10. The humeral head implant system of claim 7, wherein a distal end of the plurality of legs is positioned adjacent the distal end of the base component.

11. The humeral head implant system of claim 5, wherein a spacing between each adjacent pair of the plurality of legs is equal.

12. The humeral head implant system of claim 5, wherein each of the plurality of legs includes a first side edge extending distally, and a bottom edge extending radially inwardly from a distal end of the first side edge toward the extension.

* * * * *